(12) United States Patent
Cover et al.

(10) Patent No.: US 9,730,679 B1
(45) Date of Patent: Aug. 15, 2017

(54) DEVICE FOR STERILE UTERINE SAMPLING AND DRUG DELIVERY

(71) Applicants: Natasha Faith Cover, Lansdale, PA (US); Anna K. Parsons, Tampa, FL (US); Arun Kumar, Newark, DE (US)

(72) Inventors: Natasha Faith Cover, Lansdale, PA (US); Anna K. Parsons, Tampa, FL (US); Arun Kumar, Newark, DE (US)

(73) Assignee: University of South Florida, Tampa, FL (US)

( * ) Notice: Subject to any disclaimer, the term of this patent is extended or adjusted under 35 U.S.C. 154(b) by 197 days.

(21) Appl. No.: 14/136,912

(22) Filed: Dec. 20, 2013

Related U.S. Application Data

(60) Provisional application No. 61/740,677, filed on Dec. 21, 2012.

(51) Int. Cl.
*A61B 10/02* (2006.01)
*A61M 31/00* (2006.01)
*A61K 9/51* (2006.01)

(52) U.S. Cl.
CPC .......... *A61B 10/0291* (2013.01); *A61B 10/02* (2013.01); *A61K 9/5161* (2013.01); *A61M 31/00* (2013.01)

(58) Field of Classification Search
None
See application file for complete search history.

(56) References Cited

U.S. PATENT DOCUMENTS

| | | | | |
|---|---|---|---|---|
| 3,598,108 A | * | 8/1971 | Jamshidi | A61B 10/0233 219/229 |
| 3,777,743 A | * | 12/1973 | Binard | A61B 10/0291 600/562 |

(Continued)

FOREIGN PATENT DOCUMENTS

WO    WO 2011068874 A2 *  6/2011   ............. A61B 17/43

OTHER PUBLICATIONS

Muhammed R, Junise V, Saraswathi P, Krishnan P, Dilip C. Development and characterization of chitosan nanoparticles loaded with isoniazid for the treatment of Tuberculosis. Reseach Journal of Pharmaceutical, Biological and Chemical Sciences. Oct.- Dec. 2010; 1(4); pp. 383-390.

(Continued)

*Primary Examiner* — Devin Henson
*Assistant Examiner* — Matthew Kremer
(74) *Attorney, Agent, or Firm* — Michele L. Lawson; Smith & Hopen, P.A.

(57) ABSTRACT

A device and method for the collection of sterile specimen samples from the uterus is presented. Also presented is a method of delivering nano-encapsulated drugs to the female reproductive tract to treat pelvic inflammatory disease. The device generally is comprised of an outer cannula over which a cover is provided. A sampler may be positioned within the cannula so that when the sampler is advanced through the cannula, the sampler exits an orifice at one end of the cannula and pierces the cover causing it to retract. In use, the device is positioned within the vagina and once correctly positioned, the sampler is advanced thus piercing the cover and allowing an uncontaminated sample to be taken from the uterus or a drug to be delivered directly into the uterus.

4 Claims, 36 Drawing Sheets

(56) References Cited

U.S. PATENT DOCUMENTS

| | | | | |
|---|---|---|---|---|
| 3,857,384 | A * | 12/1974 | Watson | A61B 10/0291 |
| | | | | 600/562 |
| 4,340,066 | A | 7/1982 | Shah | |
| 4,393,879 | A | 7/1983 | Milgrom | |
| 4,396,021 | A * | 8/1983 | Baumgartner | A61B 10/0241 |
| | | | | 600/106 |
| 4,441,509 | A | 4/1984 | Kotsifas et al. | |
| 4,949,718 | A | 8/1990 | Neuwirth et al. | |
| 5,437,643 | A * | 8/1995 | Transue | A61B 17/3496 |
| | | | | 604/164.01 |
| 5,496,272 | A * | 3/1996 | Chung | A61B 17/43 |
| | | | | 604/515 |
| 5,752,970 | A * | 5/1998 | Yoon | A61B 17/3421 |
| | | | | 604/167.03 |
| 5,797,888 | A * | 8/1998 | Yoon | A61B 17/3421 |
| | | | | 604/249 |
| 5,904,927 | A * | 5/1999 | Amiji | A61K 9/205 |
| | | | | 424/422 |
| 6,514,224 | B1 | 2/2003 | Anapliotis | |
| 6,669,643 | B1 * | 12/2003 | Dubinsky | A61B 10/04 |
| | | | | 600/459 |
| 7,879,559 | B2 | 2/2011 | Alderete et al. | |
| 8,048,101 | B2 | 11/2011 | Lee-Sepsick et al. | |
| 8,528,563 | B2 | 9/2013 | Gruber | |
| 2001/0012941 | A1 * | 8/2001 | Beyar | A61B 17/0401 |
| | | | | 606/104 |
| 2001/0051189 | A1 * | 12/2001 | Alonso Fernandez | |
| | | | | A61K 9/5161 |
| | | | | 424/499 |
| 2003/0216610 | A1 * | 11/2003 | Kaneko | A61B 17/43 |
| | | | | 600/35 |
| 2005/0020937 | A1 * | 1/2005 | Reed | A61B 10/0045 |
| | | | | 600/562 |
| 2005/0137448 | A1 * | 6/2005 | Wingler | A61B 17/43 |
| | | | | 600/34 |
| 2005/0288606 | A1 * | 12/2005 | Alter | A61B 10/0291 |
| | | | | 600/572 |
| 2007/0106174 | A1 * | 5/2007 | Sanders | A61B 10/0291 |
| | | | | 600/563 |
| 2007/0173736 | A1 * | 7/2007 | Feuer | A61B 10/0291 |
| | | | | 600/562 |
| 2007/0293792 | A1 * | 12/2007 | Sliwa | A61B 5/11 |
| | | | | 600/587 |
| 2008/0249553 | A1 * | 10/2008 | Gruber | A61B 17/32002 |
| | | | | 606/171 |
| 2009/0304803 | A1 * | 12/2009 | Hasan | A61K 41/0071 |
| | | | | 424/497 |
| 2010/0033188 | A1 * | 2/2010 | Rieth | A61B 5/01 |
| | | | | 324/438 |
| 2010/0086613 | A1 * | 4/2010 | Wu | A61K 47/4823 |
| | | | | 424/499 |
| 2010/0203144 | A1 * | 8/2010 | Laurencin | A61L 27/04 |
| | | | | 424/489 |
| 2010/0221309 | A1 * | 9/2010 | Myers | A61K 8/0208 |
| | | | | 424/443 |
| 2010/0286237 | A1 * | 11/2010 | Birrer | C12N 15/111 |
| | | | | 514/44 A |
| 2011/0064664 | A1 * | 3/2011 | Lopez-Berestein | A61K 9/5115 |
| | | | | 424/9.1 |
| 2011/0064794 | A1 * | 3/2011 | Deng | A61K 9/1075 |
| | | | | 424/450 |
| 2012/0201862 | A1 * | 8/2012 | Cuesta Regueiro | A61K 9/51 |
| | | | | 424/400 |
| 2012/0277158 | A1 * | 11/2012 | Castaigne | A61K 47/48238 |
| | | | | 514/17.5 |
| 2013/0011333 | A1 * | 1/2013 | Yuan | A61K 9/5146 |
| | | | | 424/1.29 |

OTHER PUBLICATIONS

Chambers JT, Chambers SK. Endometrial Sampling: When? Where? Why? With What? Clinical Obstetrics and Gynecology. Mar. 1992; 35(1); pp. 28-39.

Keilani A, Boulieu D, Raudrant D, Carraz M, Quenin P. Role of Chlamydia trachomatis in tubal pathology (acute salpingitis and tubal sterility). Microbiological study of 175 samples of peritoneal fluid. J Gynecol Obstet Biol Reprod (Paris). 1989; 18(2); pp. 167-172.

Punnonen R, Terho P NV, Meurman O. Chlamydial serology in infertile woman by immunofluorescence. Fertil Steril. 1979;31(6):656-659.

Racovita S, Vasiliu S, Popa M, Luca C. Polysaccharides based on micro- and nanoparticles obtained by ionic gelation and their application as drug delivery systems. Revue Roumaine de Chimie. 2009;54(9):709-718.

Rein DB, Kassler WJ, Irwin KL, Rabiee L. Direct Medical Cost of Pelvic Inflammatory Disease and Its Sequelae: Decreasing but Still Substantial Obstetrics and Gynecology. 2000;95(3):397-402.

Ross JD. An Update on Pelvic Inflammatory Disease. Sex Transm Inf. 2002;78:18-19.

Sampathkumar SG, Yarem KJ. Targeting Cancer Cells Dendrimer. Chemistry & Biology. 2005;12:5-13.

Sarmento B, Ribeiro A, Veiga F, Ferreira D. Development and characterization of new insulin containing polysaccharide nanoparticle. Colloids and Surfaces B: Biointerface. 2006;53:193-202.

Shanmuganathan S, Shanumugasundaram N, Adhirajan N, Ramyaa-Lakshmi TS, Babu M. Preparation and characterization of chitosan microsphere for doxycycline delivery. Carbohydrate Polymers. 2008; 73:201-211.

Shepard MK, Jones RB. Recovery of Chlamydia trachomatis from endometrial and fallopian tube biopsies in women with infertility of tubal origin. Fertil Steril. 1989;52(2):232-238.

Shirashi S, Imani T, Ogtagiri M. Controlled release of indomethacin by chitosan-polyelectrolyte complex optization and In vivo/in vitro evaluation. J. Control. Release. 1993;25(3):217-225.

Shu XZ, Zhu KJ. A novel approach to prepare tripolyphospate/chitosan complex beads for controlled release drug delivery. Int. J. Pharm. 2000;201(1):51-58.

Soper DE. Pelvic inflammatory disease. Obstet Gynecol. 2010;116(2):419-428.

Stubbs E, Schamp A. The evidence is in. Why are IUDs still out? Family physicians' perceptions of risk and indications. Can Fam Physician. 2008;54(4):560-566.

Sweet R. Role of Bacterial Vaginosis in Pelvic Inflammatory Disease. Clinical Infectious Diseases. 1995;20(2):271-275.

Tiyaboonchai W. Chitosan Nanoparticles : A Promising System for Drug Delivery. Naresuan University Journal. 2003;11(3):51-66.

Tokumitsu H, Ichikawa H, Fukumori Y. Chitosan-Gadopentetic Acid Complex Nanoparticles for Gadolinium Neutron-Capture Therapy Therapy of Cancer: Preparation by Novel Emulsion-Droplet Coalescence Technique and Characterization. Pharmaceutical Research. 1999;16(12):1830-1835.

Torchillin V. Antibody-modified liposomes for Cancer Chemotherapy. Expert Opin. Drug Deliv. 2008;5(9):1003-1025.

Walker C, Wiesenfeld H. Antibiotic Therapy for Acute Pelvic Inflammatory Disease: The 2006 Centers for Disease Control and Prevention Sexually Transmitted Diseases Treatment Guidelines. Clinical Infectious Diseases. 2007;44 (S111-22).

Wang JJ, Zeng ZW, Xiao RZ, et al. Recent advances of chitosan nanoparticles as drug carriers. International Journal of Nanomedicine. 2011;6:765-774.

Watzke HJ, Dieschbourg C. Novel silica-biopolymer nanocomposites: the silica sol-gel process in biopolymer organogels. Advances in Colloid and Interface Science. 1994;50:1-14.

Wiesenfeld HC, Hillier SL, Krohn MA, et al. Lower Genital Tract Infection and Endometritis: Insight Into Subclinical Pelvic Inflammatory Disease. The American College of Obststricians and Gynecologists. 2002;100(3):456-463.

Wolner-hanssen P. Silent pelvic inflammatory disease: is it overstated? Obstet Gynecol. 1995;86(3):321-325.

Xi-Peng G, Da-Ping Q, Kai-Rong L, Tao W, Peng X, Mai KC. Preparation and Characterization of Cationic Chitosan-modified

(56) References Cited

OTHER PUBLICATIONS

Poly(D,L-lactide-co-glycolide) Copolymer Nanospheres as DNA Carriers. J Biomater Appl. 2008; 22:353-370.
Xu Y, Du Y. Effect of molecular structure of chitosan on protein delvery properties of chitosan nanoparticles. Int. J. Pharm. 2003;250(1):215-226.
Zhang H, Oh M, Allen C, Kumacheva E. Monodisperse Chitosan Nanoparticles for Mucosal Drug Delivery. Biomacromolecules. 2004; 5:2461-2468.
Zhang H, Wu S, Tao Y, Zang L, Su Z. Preparation and Characterization of Water-Soluble Chitosan Nanoparticles as Protein Delivery System. Journal of Nanomaterials. 2010:1-5.
Centers for Disease Control and Prevention. Sexually Transmitted Diseases Treatment Guidelines. MMWR. 2010;59 (No. RR-12):1-109.
Centers for Disease Control and Prevention (CDC). Cephalosporin susceptibility among Neisseria gonorrhoeae isolates—United States, 2000-2010. MMWR Morb Mortal Wkly Rep. 2011;60(26):873-877.
Agnihotri SA, Mallikarjuna NN, Aminabhavi TM. Recent Advances on chitosan-based micro- and nanoparticles in drug delivery. Journal of Controlled Release. 2004;100:5-28.
Alameh M, Jean M, DeJesus D, Buschmann MD, Merzouk A. Chitosanase-based method for RNA isolation from cells transfected with chitosan/siRNA nanocomplexes for real-time RT-PCR in gene silencing. International Journal of Nanomedicine. 2010;5:473-481.
Beigi R, Wiesenfeld H. Pelvic Inflammatory disease: new diagnostic criteria and treatment. Obstetrics and Gynecology Clinics of North America. 2003;30:777-793.
Bell JD,Bergin IL, Schmidt K, Zochowski MK, Aronoff DM, Patton DL. Nonhuman Priamte Models Used to Study Pelvic Inflammatory Disease Cause by Chlamydia tracomatis. Infect Dis Obstet Gynecol. 2011:1-7.
Bodmeier R, Chen H, Paeratakul O. A Novel Approach to the Oral Delivery of Microparticles or Nanoparticles Pharm Res. 1989;6(5):413-417.
Bollinger CC. Bacterial Flora of the Nonpregnat Uterus: A New Culture Technic. Obstetrics and Gynecology. 1964;23(2):251-255.
Boonsongrit Y, Mitrevej A, Mueller BW. Chitosan drug binding by ionic interaction. European Journal of Pharmaceutics and Biopharmaceutics. 266;62:267-274.
Calvo P, Remunan-Lopez C, Vila-Jata JL, Alonson MJ. Novel Hydrophilic Chitosan-polyethylene Oxide Nanoparticles as Protein Carriers J. Appl. Polym. Sci. 1997;63(1):125-132.
Calvo P, Remunan-Lopez C, Vila-Jata JL, Alonso MJ, Chitosan and Chitosan/Ethylene Oxide-Propylene Oxide Block Copolymer Nanoparticles as Novel Carriers for Proteins and Vaccines. Pharm Res. 1997;14(10):1431-1436.
Calvo P, Vila-Jato J, Alonso MJ. Evalution of catonic polymer-coated nanocapsules as ocular drug carriers. Journal of Pharmaceutics. 1997;153:41-50.
Cooper JM, Erickson ML. Endmetrial Sampling Techniques in the Diagnosis of Abnormal of Uterine Bleeding. Obstetrics and Gynecology Clinics of North America. 2000;27(2):235-244.
Cover N, Lai-Yuen S, Parsons A, Kumar A. Syngergetic Effects of doxycycline-load chitosan nanoparticles for improving drug delivery and efficacy. International Journal of Nanomedicine. 2012;7:2411-2419.
Crossman S. The Challenge of Pevic Inflammatory Disease. American Family Physician. 2006;73(5):859-864.
Dayan L. Pelvic Inflammatory Disease. Australian Family Physician. 2006;35(11)858-862.
Duff P, Gibbs R, Blanco J, St. Clair P. Endometrial Culture Techniques in Puerperal Patients. Obstetrics and Gynecology. 1983;61(2):217-222.
Duncan R. The Dawning Era of Polymer Therapeutic. Nature Reviews Drug Discovery. 2003;2:347-360.
Dung TH, Lee SR, Han SD, et al. Chitosan-TPP nanoparticles as a release system of antiense oligonucleotide in the oral environment. J. Nanosci. Nanotechnol. 2007;7(11):3695-3699.

The ESHRE Capri Workshop Group. Intrauterine devices and intrauterine systems. Human Reproduction Update. 2008;14(3):197-208.
Fernandez-Urrusuno R, Clavo P, Remunan-Lopez C, Vila-Jato JL, Alonso MJ. Enchancement of nasal absorption of insulin using chitosan nanoparticles. Pharm. Res. 1999;16(10):1576-1581.
Gan Q, Wang T, Cochrane C, McCarron P. Modulation of surface charge, particle size and morphological properties of chitosan-TPP nanoparticles intended for gene delivery. Colloids and Surfaces B: Biointerfaces. 2005;44:65-73.
Goshen T, Shpigel NY. Evaluation of intrauterine antibiotic treatment of clinical metritis and retained fetal membranes in dairy cows. Theriogenology. 2006;66(9): 2210-2218.
Goycoolea FM, Lollo G, Remunan-Lopez G, Quaglia F, Alonso MJ. Chitosan-Alginate Blended Nanoparticles as Carriers for the Transmucosal Delivery of Macromolecules. Biomacromolecules. 2009;10:1736-1743.
Grenha A, Seijo B, Serra C, Remunan-Lopez C. Chitosan Nanoparticle-Loaded Mannitol Microspheres: Structure and Surface Characterization. Biomacromolecules. 2007; 8: 2072-2079.
Guilbeau JA, Schaub IG. Uterine Cutlture Technique: A simple Method for Avoiding Contamination by the Cervical and Vaginal Flora. American Journal of Obstetrics & Gynecology. Aug. 1949; 58(2): 407-410.
Haggerty C, Ness R. Newest Approaches to Treatment of Pelvic Inflammatory Disease: A Review of Recent Randomized Clinical Trials. Clinical Infectious Diseases. 2007;44:953-960.
Hay PE, Pittrof R. Has the effectiveness of a single chlamydia test in preventing pelvic inflammatory disease over 12 months been overestimated? Women's Health. 2010;6(5):627-630.
Heinberg EM, McCoy TW, Pasic R. The Perforated Intrauterine Device: Endoscopic Retrieval. JSLS. 2008;12 (1):97-100.
Henry-Suchet J. PID: Clinical and Laparoscopic Aspects. Ann N Y Acad Sci. 2000;900:301-308.
Humber N. The occasional D & C. Can J Rural Med. 2009;14(3):115-118.
Jaiyeoba O, Soper DE. A Practical Approach to the Diagnosis of Pelvic Inflammatory Disease. Infect Dis Obstet Gynecol. 2011:1-6.
K.A. Janes, et al., Polysaccharide colloidal particles as delivery systems for macromolecules. Advanced Drug Delivery Reviews, 47 (2001), 83-97.
Knuppel R, Scerbo J, Dzink J, Mitchell G, Cetrulo C, Barlett J. Quantitive Transcervical Uterine Cultures With a New Device. Obstetrics and Gynecology. 1981;57(2):243-248.
Ko JA, Park HJ, Hwang SJ, Park JB, Lee JS. Preparation and Characterization of Chitosan Microparticles intended for Controlled Drug Delivery. International Journal of Pharmaceutics. 2002; 249:165-174.
Lee YS, Jang KA, Cha JD. Synergistic Antibacterial Effect between Silibinin and Antibiotics in Oral Bacteria. Journal of Biomedicine Biotechnology. 2012:1-7.
Liu Z, Jiao Y, Wang Y, Zhou C, Zhang Z. Polysaccharides-based nanoparticles as drug delivery systems. Adv Drug Deliv Rev. 2008;60:1650-1662.
Mehrotra A, Nagarwal RC, Kumar-Pandit J. Lomustine Loaded Chitosan Nanoparticles: Characterization and in-Vitro Cytotoxicity on Human Lung Cancer Cell Line L132. Chem. Pharm. Bull. 2011;59(3):315-320.
Moghimi SM, Hunter AC, Murray JC. Long-circulating and target specific nanoparticles: theory to practice. Pharmacol. Rev. 2001;53(2):283-318.
Mohanraj VJ, Chen Y. Nanoparticle- A Review. Tropical Journal of Pharmaceutical Research. 2006;5(1):561-573.
Moore DE, Spadoni LR, Foy HM. Incresed Frequency of Serum antibodies to Chlamydia Trachomatis in infertility due to distal tubal disease. The Lancet 1982;2(8298):574-577.
Nagpal K, Kumar-Singh S, Nath-Mishr D. Chitosan Nanoparticles: A Promising System in Novel Drug Deliver. Chem. Pharm Bull. 2010;58(11):1423-1430.
Nicol S. Life after death for empty shells. New Sci. 1991;129:46-48.
Ohya Y, Shiratani M, Kobayashi H, Ouchi T. Release Behavior of 5-Fluorouracil from Chitosan-Gel Nanospheres Immobilizing

(56) References Cited

OTHER PUBLICATIONS

5-Fluorouracil Coated with Polysaccharides and Their Cell Specific Cytotoxicity. Journal of Macromolecular Science. 1994;31(5):629-642.
Pan Y, Li Y, Zhao H, et al. Bioadhesive Polysaccharide in Protein Delivery System: Chitosan nanoparticles improve the intestinal absorption of insulin in vivo. Int. J. Pharm. 202;249:139-147.
Patel JK, Jivani NP. Chitosan Based Nanoparticles in Drug Delivery. International Journal of Pharmaceutical Sciences and Nanotechnology. 2009;2(2):517-522.
Patel MP, Patel RR, Patel JK. Chitosan Mediated Drug delivery System: A Review. J Pharm Pharmaceut Sci 2010:13(3)536-557.
Pawan P, Mayur M, Ashwin S. Role of Natural Polymers in Sustained Release Drug Delivery System: Applications and Recent Approaches. International Research Journal of Pharmacy. 2011;2(9):6-11.
Peipert J, Boardman L, Hogan J, Sung J, Mayer K. Laboratory Evaluation of Acute Upper Genital Tract Infection. Obstetrics and Gynecology 1996;87:730-736.
Peterson HB, Galaid EI, Zenilman JM. Pelvic Inflammatory Disease: Review of Treatment Options. Reviews of Infectious Diseases. 1990;12(6):656-664.
Phaechamud T, Charoenteeraboon J. Antibacterial Activity and Drug Release of the Chitosan Sponge Containing Hyclate. AAPS PharmSciTech. 2008;9(3):829-835.
Pinto-Reis C, Neufeld RJ, Ribeiro AJ, Veiga F. Nanoencapsulation I. Methods for preparation of drug-loaded polymeric nanoparticles. Nanomedicine. 2006:8-21.

\* cited by examiner

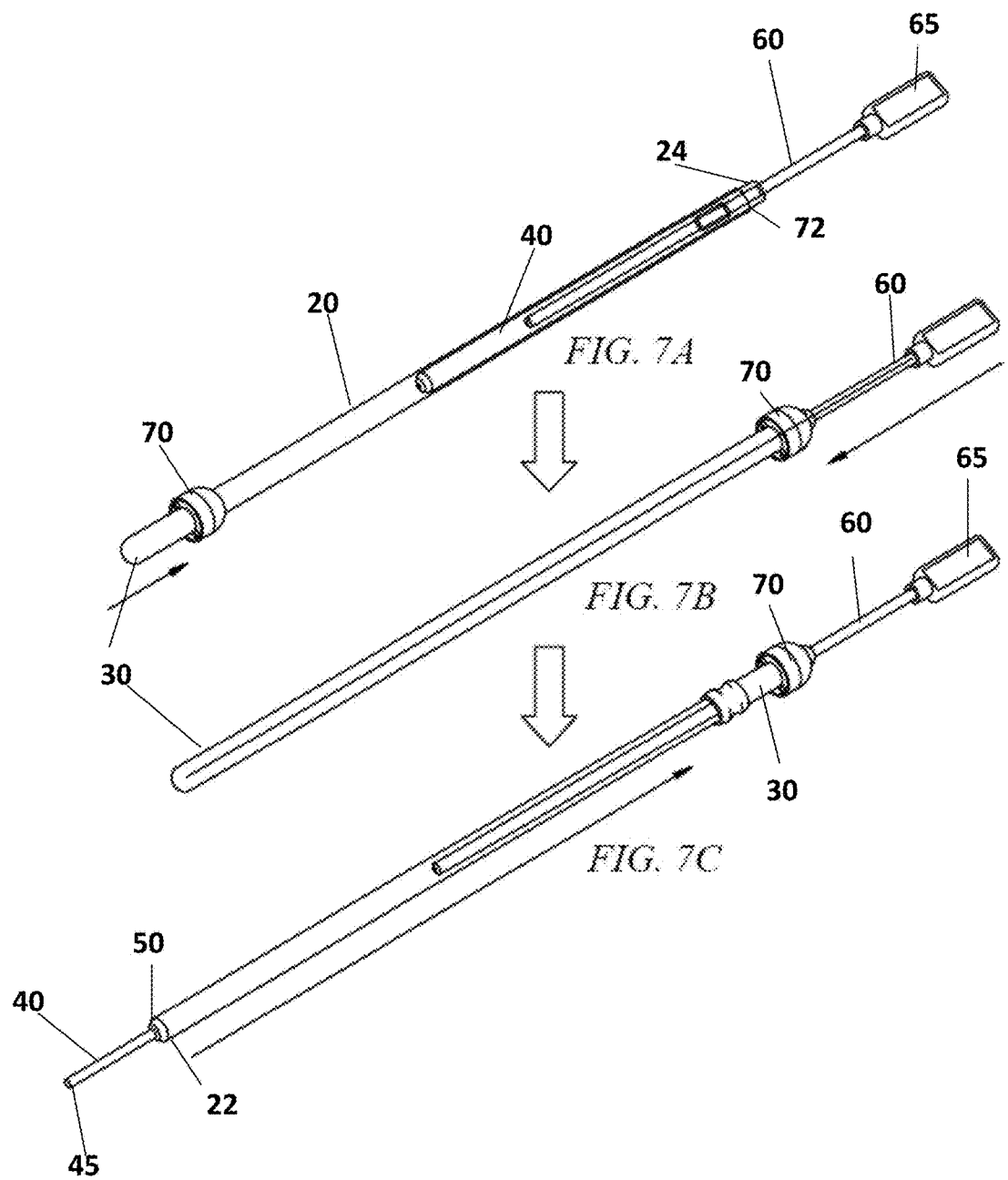

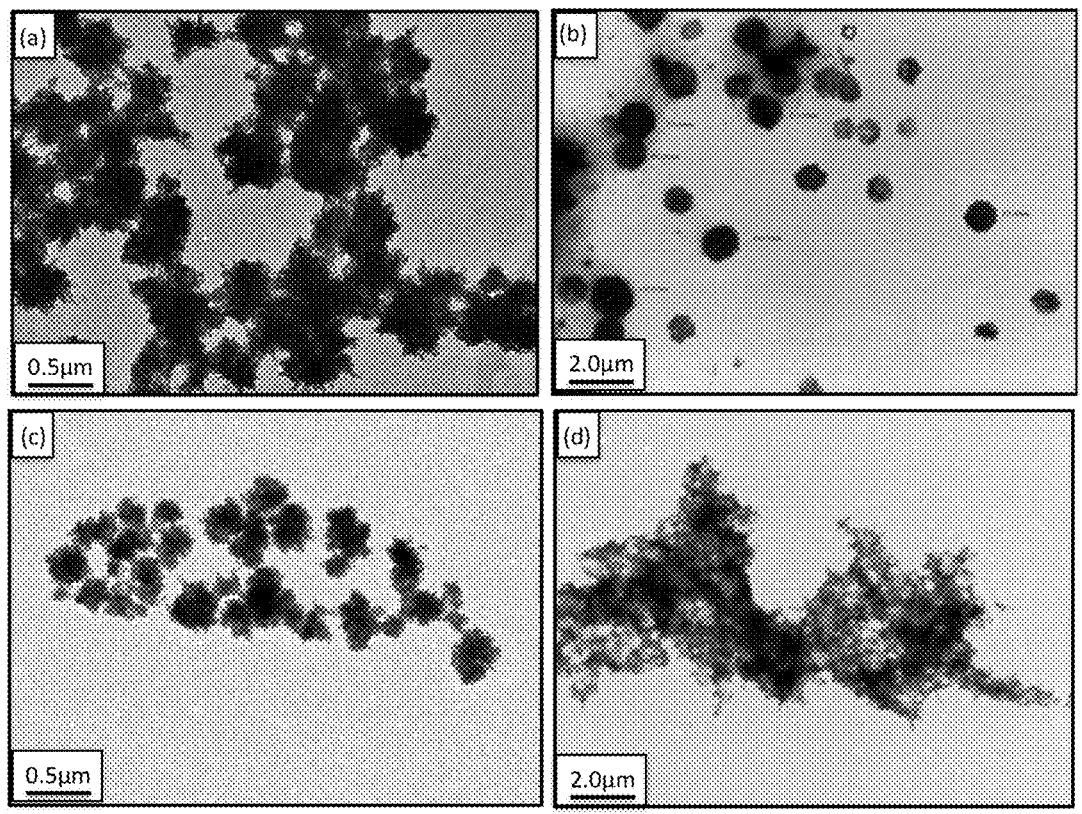
FIG. 14A-D

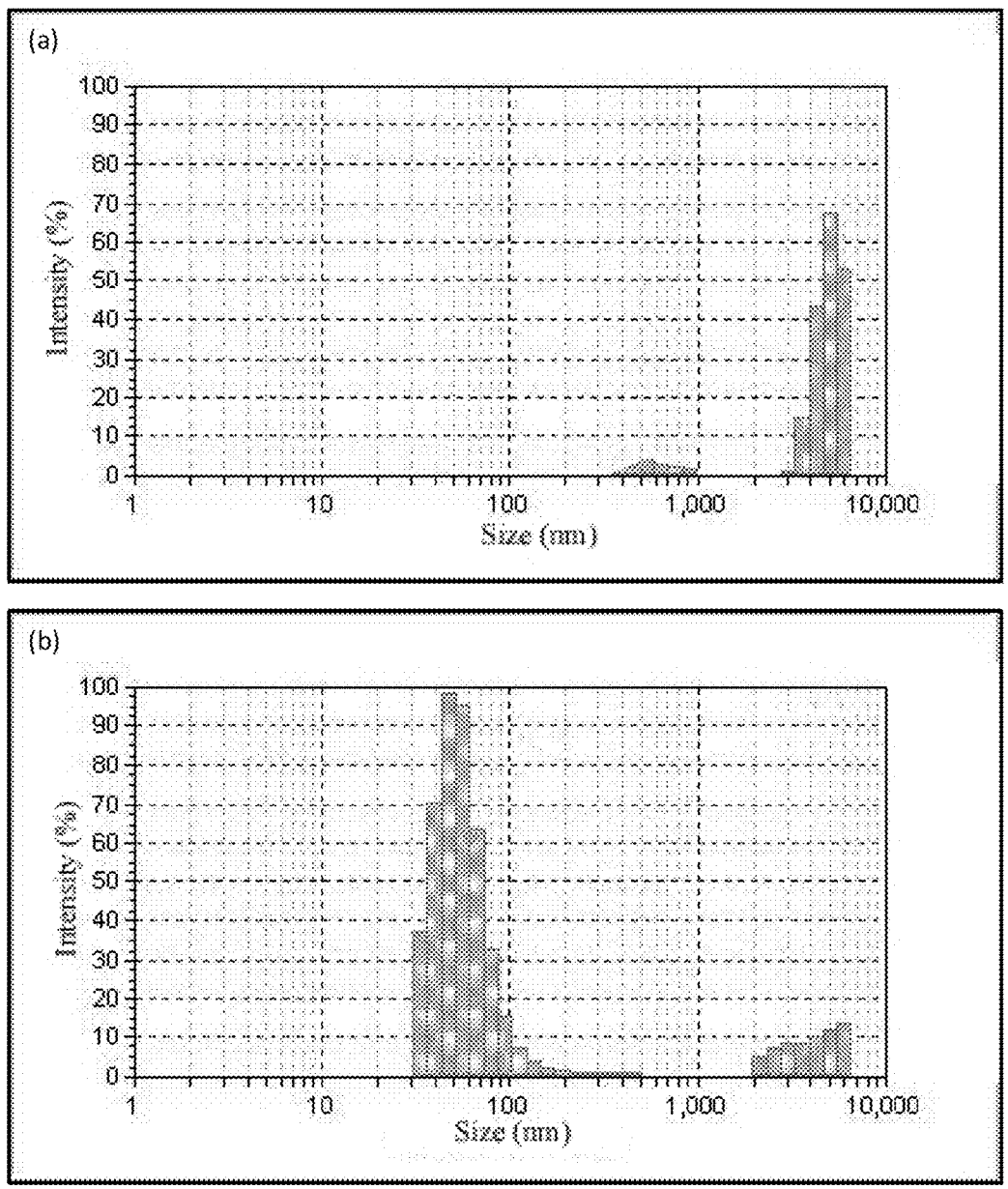
FIG. 15A-B

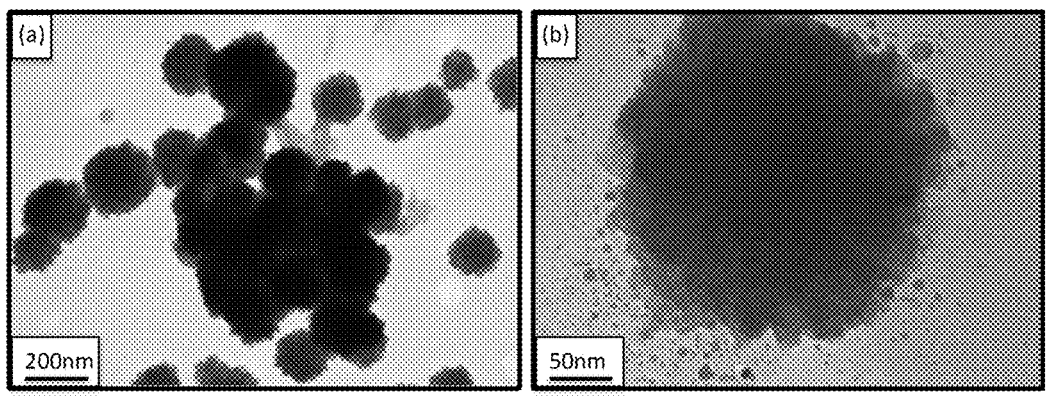
FIG. 16A-B
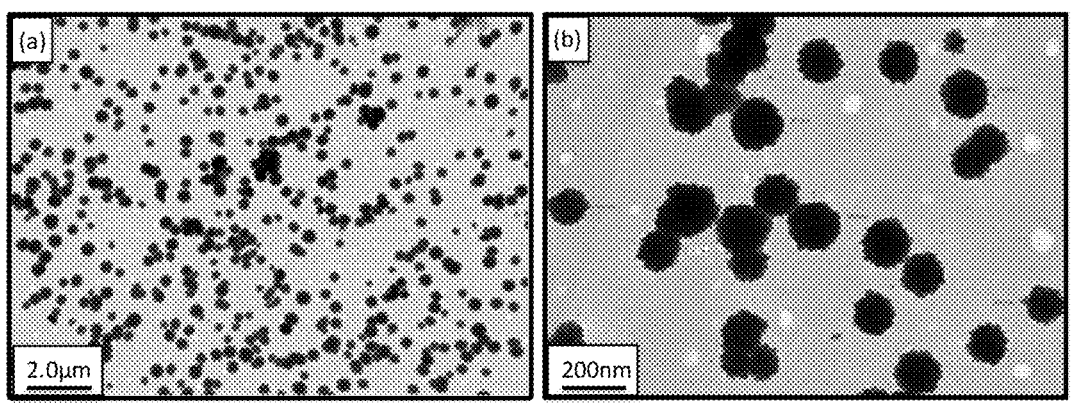
FIG. 17A-B

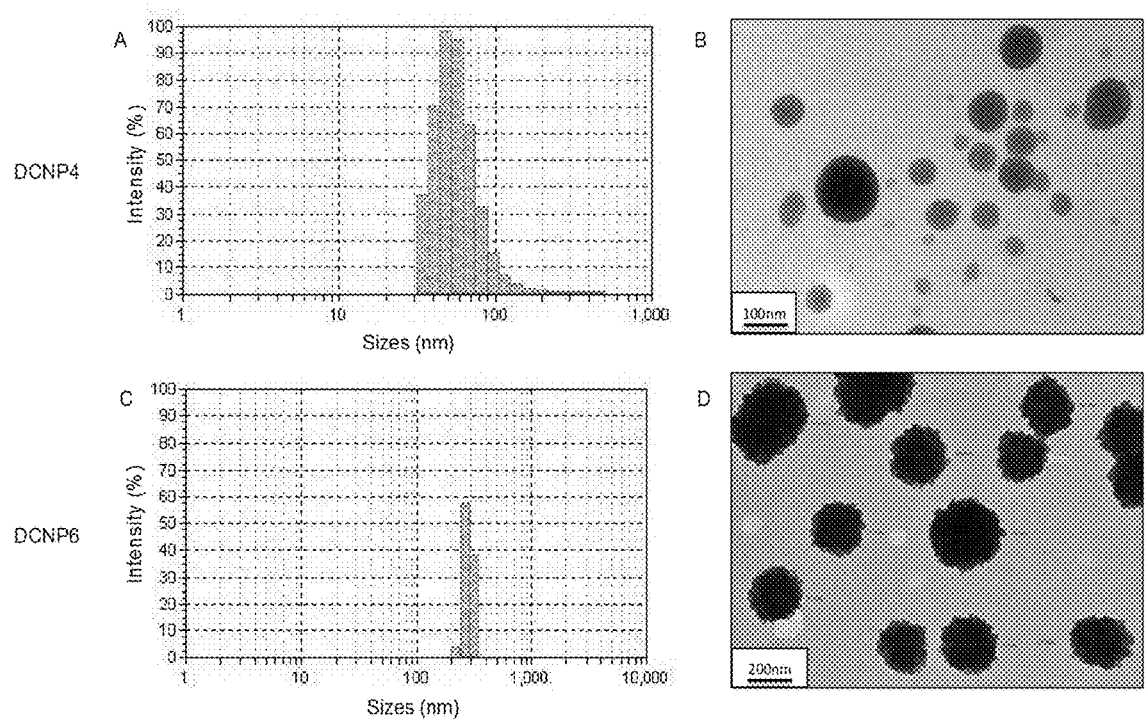
FIG. 18A-D

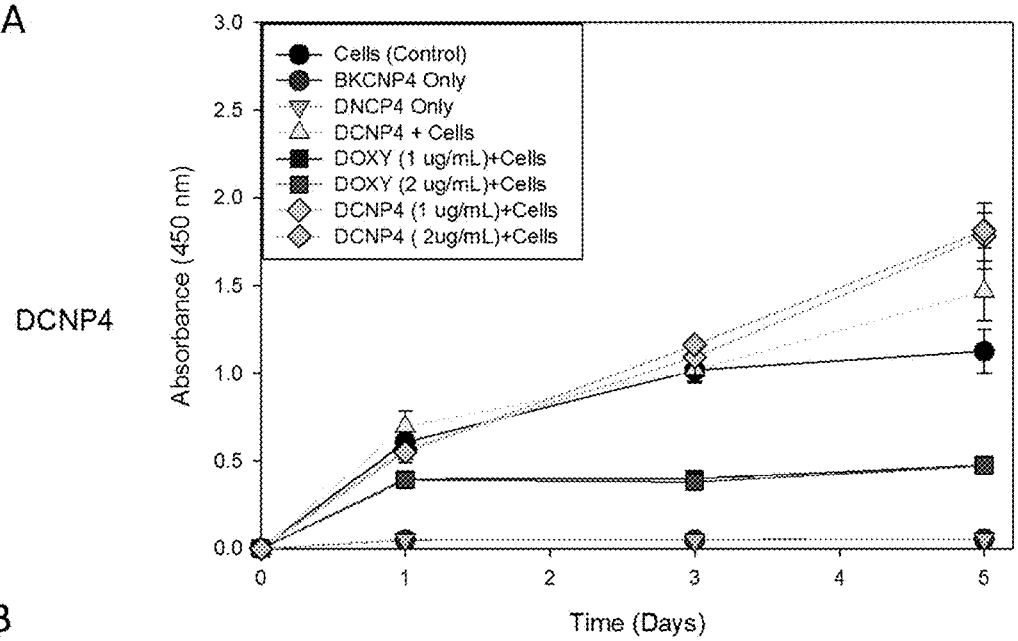
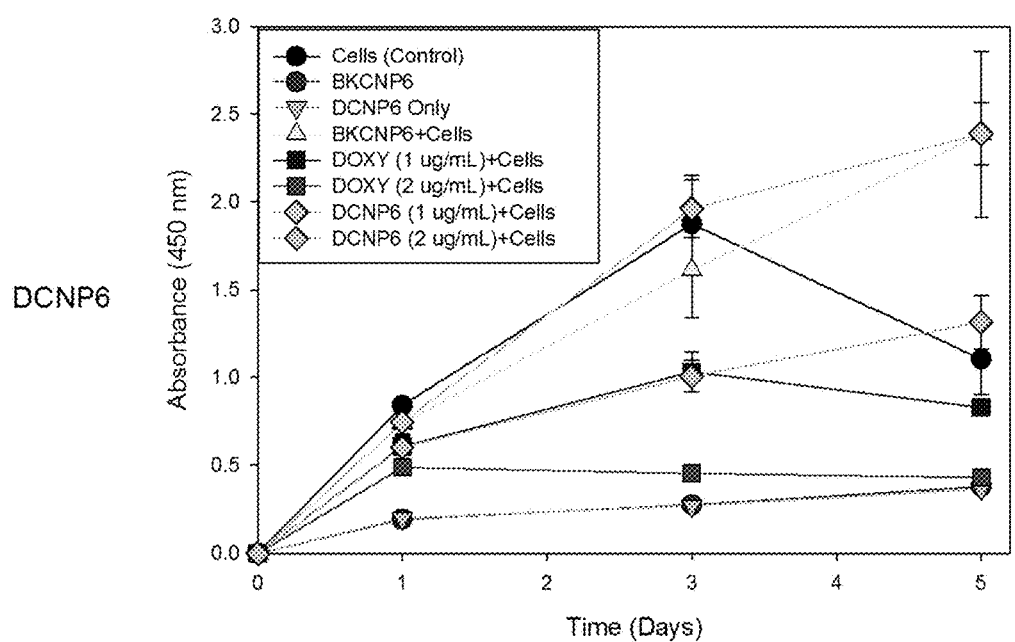
FIG. 21A-B

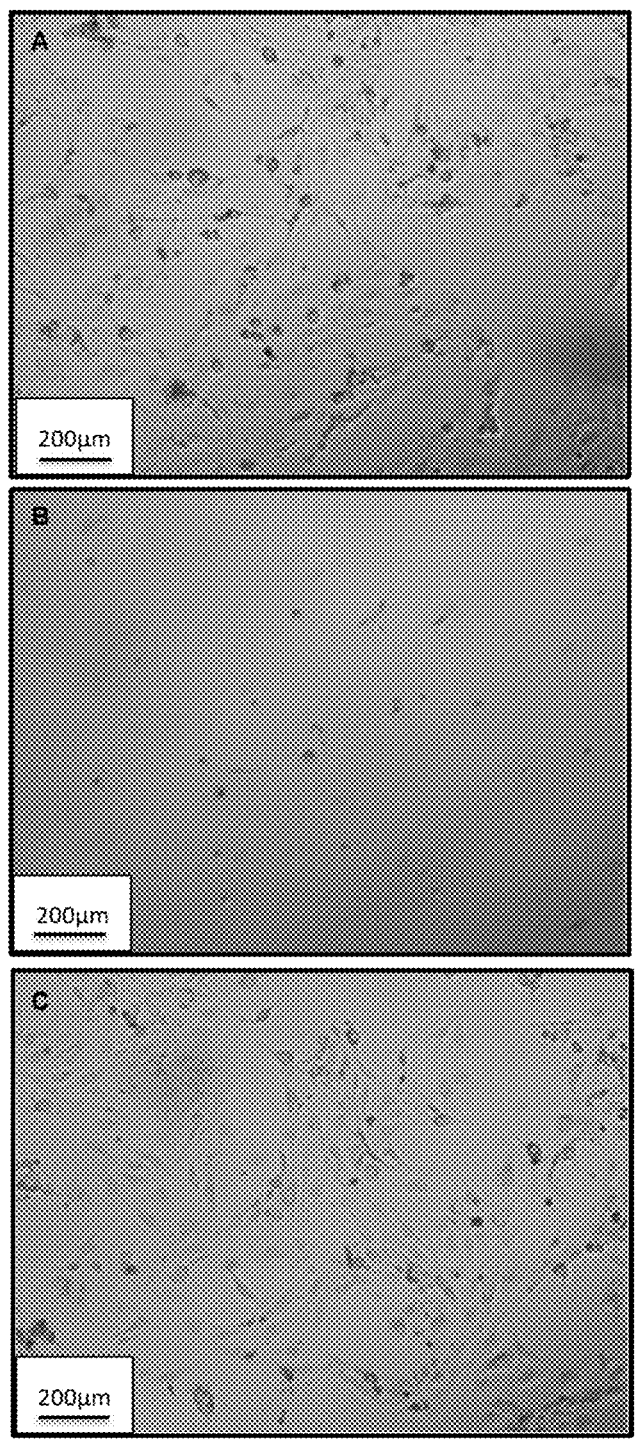
FIG. 22A-C

| F | CS_TYPE | CS_CONC | CS_SOLV | PRO_TIME | TPP_CONC | TPP_SOLV | DRUG | ORDER | RATIO | SYN_TIME | CENTRI | REC_SOLV | AVERAGE PAR_SIZE |
|---|---|---|---|---|---|---|---|---|---|---|---|---|---|
| 1 | 0 | 0.2 | 0 | 60 | 0.84 | 0 | 1 | 0 | 4 | 60 | 1 | 1 | 90 |
| 2 | 0 | 0.2 | 0 | 60 | 0.84 | 0 | 1 | 0 | 4 | 60 | 1 | 1 | 155 |
| 3 | 0 | 0.1 | 0 | 60 | 0.21 | 0 | 0 | 1 | 4 | 60 | 1 | 1 | 33 |
| 4 | 0 | 0.1 | 0 | 60 | 0.42 | 0 | 0 | 1 | 4 | 60 | 1 | 1 | 114 |
| 5 | 0 | 0.1 | 0 | 30 | 0.42 | 0 | 0 | 1 | 4 | 120 | 0 | 1 | 99.5 |
| 6 | 0 | 0.1 | 0 | 30 | 0.42 | 0 | 0 | 1 | 4 | 1440 | 0 | 1 | 415 |
| 7 | 0 | 0.1 | 0 | 30 | 0.42 | 0 | 0 | 1 | 4 | 60 | 0 | 1 | 142 |
| 8 | 0 | 0.2 | 0 | 60 | 0.84 | 0 | 1 | 1 | 4 | 1440 | 1 | 1 | 3486 |
| 9 | 0 | 0.1 | 0 | 60 | 0.42 | 0 | 1 | 1 | 4 | 1440 | 1 | 1 | 4905 |
| 10 | 1 | 0.2 | 1 | 1440 | 0.84 | 1 | 1 | 0 | 2 | 60 | 1 | 0 | 102 |
| 11 | 1 | 0.2 | 1 | 1440 | 0.84 | 1 | 1 | 0 | 2 | 60 | 1 | 0 | 143 |
| 12 | 1 | 0.2 | 1 | 1440 | 0.84 | 1 | 1 | 0 | 2 | 60 | 0 | 0 | 169.5 |
| 13 | 0 | 0.2 | 1 | 1440 | 0.84 | 1 | 1 | 0 | 2 | 60 | 1 | 0 | 427 |
| 14 | 0 | 0.2 | 1 | 1440 | 0.84 | 1 | 1 | 0 | 1 | 60 | 1 | 0 | 320 |
| 15 | 0 | 0.2 | 1 | 1440 | 0.84 | 1 | 1 | 1 | 2 | 60 | 1 | 0 | 620 |
| 16 | 1 | 0.2 | 1 | 1440 | 0.84 | 1 | 1 | 0 | 1 | 60 | 1 | 0 | 600 |
| 17 | 0 | 0.2 | 1 | 1440 | 0.84 | 1 | 1 | 0 | 1 | 60 | 1 | 1 | 4000 |
| 18 | 1 | 0.2 | 1 | 1440 | 0.84 | 1 | 1 | 0 | 1 | 60 | 0 | 1 | 4000 |
| 19 | 0 | 0.2 | 1 | 1440 | 0.84 | 1 | 1 | 0 | 1 | 120 | 0 | 1 | 6000 |
| 20 | 1 | 0.2 | 1 | 1440 | 0.84 | 1 | 1 | 0 | 1 | 120 | 0 | 1 | 3550 |
| 21 | 0 | 0.2 | 1 | 1440 | 0.84 | 1 | 1 | 0 | 1 | 120 | 1 | 1 | 4450 |
| 22 | 1 | 0.2 | 1 | 1440 | 0.84 | 1 | 1 | 0 | 1 | 120 | 1 | 1 | 5700 |
| 23 | 0 | 0.2 | 1 | 1440 | 0.84 | 1 | 1 | 1 | 2 | 120 | 0 | 1 | 575 |
| 24 | 1 | 0.2 | 1 | 1440 | 0.84 | 1 | 1 | 1 | 2 | 120 | 0 | 1 | 2000 |
| 25 | 0 | 0.2 | 1 | 1440 | 0.84 | 1 | 1 | 1 | 2 | 60 | 0 | 0 | 595 |
| 26 | 0 | 0.2 | 1 | 1440 | 0.42 | 1 | 1 | 1 | 2 | 60 | 0 | 0 | 265 |
| 27 | 0 | 0.2 | 1 | 1440 | 0.84 | 1 | 1 | 0 | 2 | 60 | 0 | 0 | 3250 |
| 28 | 0 | 0.2 | 1 | 1440 | 0.42 | 1 | 1 | 0 | 2 | 60 | 0 | 0 | 4000 |
| 29 | 1 | 0.2 | 1 | 1440 | 0.84 | 1 | 1 | 1 | 2 | 60 | 0 | 0 | 3500 |
| 30 | 1 | 0.2 | 1 | 1440 | 0.84 | 1 | 1 | 0 | 2 | 60 | 0 | 0 | 3175 |
| 31 | 1 | 0.2 | 1 | 1440 | 0.42 | 1 | 1 | 1 | 2 | 60 | 1 | 0 | 70 |
| 32 | 1 | 0.2 | 1 | 1440 | 0.42 | 1 | 1 | 0 | 2 | 60 | 0 | 0 | 3750 |
| 33 | 0 | 0.2 | 1 | 1440 | 0.75 | 1 | 1 | 1 | 2 | 60 | 0 | 0 | 685 |
| 34 | 0 | 0.2 | 1 | 1440 | 0.6 | 1 | 1 | 1 | 2 | 60 | 0 | 0 | 255 |
| 35 | 1 | 0.2 | 1 | 1440 | 0.75 | 1 | 1 | 1 | 2 | 60 | 0 | 0 | 1500 |
| 36 | 1 | 0.2 | 1 | 1440 | 0.6 | 1 | 1 | 1 | 2 | 60 | 0 | 0 | 675 |
| 37 | 1 | 0.1 | 1 | 60 | 0.42 | 0 | 0 | 1 | 1 | 60 | 1 | 0 | 5450 |
| 38 | 1 | 0.1 | 1 | 60 | 0.42 | 0 | 0 | 1 | 1 | 60 | 0 | 0 | 3500 |
| 39 | 1 | 0.1 | 1 | 60 | 0.42 | 0 | 1 | 1 | 1 | 60 | 1 | 0 | 4000 |
| 40 | 1 | 0.1 | 1 | 60 | 0.42 | 0 | 1 | 1 | 1 | 60 | 0 | 0 | 4250 |
| 41 | 1 | 0.2 | 1 | 60 | 0.42 | 0 | 0 | 1 | 1 | 60 | 1 | 0 | 5000 |
| 42 | 1 | 0.2 | 1 | 60 | 0.42 | 0 | 0 | 1 | 1 | 60 | 0 | 0 | 4000 |
| 43 | 1 | 0.2 | 1 | 60 | 0.42 | 0 | 1 | 1 | 1 | 60 | 1 | 0 | 3500 |
| 44 | 1 | 0.2 | 1 | 60 | 0.42 | 0 | 1 | 1 | 1 | 60 | 0 | 0 | 2500 |
| 45 | 1 | 0.1 | 0 | 60 | 0.42 | 0 | 0 | 1 | 1 | 60 | 1 | 0 | 4050 |
| 46 | 1 | 0.1 | 0 | 60 | 0.42 | 0 | 0 | 1 | 1 | 60 | 0 | 0 | 4050 |
| 47 | 1 | 0.1 | 0 | 60 | 0.42 | 0 | 1 | 1 | 1 | 60 | 1 | 0 | 3750 |
| 48 | 1 | 0.1 | 0 | 60 | 0.42 | 0 | 1 | 1 | 1 | 60 | 0 | 0 | 2800 |
| 49 | 1 | 0.2 | 0 | 60 | 0.42 | 0 | 0 | 1 | 1 | 60 | 1 | 0 | 2545 |
| 50 | 1 | 0.2 | 0 | 60 | 0.42 | 0 | 0 | 1 | 1 | 60 | 0 | 0 | 2550 |
| 51 | 1 | 0.2 | 0 | 60 | 0.42 | 0 | 1 | 1 | 1 | 60 | 1 | 0 | 3550 |
| 52 | 1 | 0.2 | 0 | 60 | 0.42 | 0 | 1 | 1 | 1 | 60 | 0 | 0 | 1800 |
| 53 | 1 | 0.1 | 1 | 1440 | 0.42 | 0 | 0 | 1 | 1 | 60 | 1 | 1 | 3000 |
| 54 | 1 | 0.1 | 1 | 1440 | 0.42 | 0 | 0 | 1 | 1 | 60 | 0 | 1 | 3950 |
| 55 | 1 | 0.1 | 1 | 1440 | 0.42 | 0 | 1 | 1 | 1 | 60 | 1 | 1 | 5000 |
| 56 | 1 | 0.1 | 1 | 1440 | 0.42 | 0 | 1 | 1 | 1 | 60 | 0 | 1 | 6000 |
| 57 | 1 | 0.2 | 1 | 1440 | 0.42 | 0 | 0 | 1 | 1 | 60 | 1 | 1 | 950 |
| 58 | 1 | 0.2 | 1 | 1440 | 0.42 | 0 | 0 | 1 | 1 | 60 | 0 | 1 | 5500 |
| 59 | 1 | 0.2 | 1 | 1440 | 0.42 | 0 | 1 | 1 | 1 | 60 | 1 | 1 | 5550 |
| 60 | 1 | 0.2 | 1 | 1440 | 0.42 | 0 | 1 | 1 | 1 | 60 | 0 | 1 | 5050 |
| 61 | 1 | 0.1 | 1 | 1440 | 0.42 | 1 | 0 | 1 | 1 | 60 | 1 | 1 | 5000 |
| 62 | 1 | 0.1 | 1 | 1440 | 0.42 | 1 | 0 | 1 | 1 | 60 | 0 | 1 | 4100 |
| 63 | 1 | 0.1 | 1 | 1440 | 0.42 | 1 | 1 | 1 | 1 | 60 | 1 | 1 | 5900 |
| 64 | 1 | 0.1 | 1 | 1440 | 0.42 | 1 | 1 | 1 | 1 | 60 | 0 | 1 | 5300 |

*FIG. 23*

| AIC-based stepwise forward selection (RDA) | | | | | | | |
|---|---|---|---|---|---|---|---|
| Conditional Tests: (each variable separately) | | | | | | | |
| RSS | $R^2$ | $R^2$adj | AIC | Wts | Delta | Ratio | Variables |
| $1.7401e^{+08}$ | 0.3105 | 0.2994 | 952.4053 | 0 | 0.9958 | 1 | Chitosan:TPP Ratio |
| $2.0692e^{+08}$ | 0.1802 | 0.1669 | 963.4904 | 11.0851 | 0.0039 | 255.3269 | Chitosan Type |
| $2.3345e^{+08}$ | 0.0750 | 0.0601 | 971.2121 | 18.8068 | $8.2099e^{-05}$ | $1.2129e^{+04}$ | TPP Concentration |
| $2.3659e^{+08}$ | 0.0626 | 0.0475 | 972.0659 | 19.6606 | $5.3571e^{-05}$ | $1.8589e^{+04}$ | Chitosan Concentration |
| $2.3771e^{+08}$ | 0.0582 | 0.0430 | 972.3683 | 19.9630 | $4.6054e^{-05}$ | $2.1623e^{+04}$ | Wash/Reconstitution Solution |
| $2.3964e^{+08}$ | 0.0505 | 0.0352 | 972.8854 | 20.4801 | $3.5562e^{-05}$ | $2.8002e^{+04}$ | Chitosan Dissolving Solution |
| $2.5239e^{+08}$ | NaN | NaN | 974.0718 | 21.6665 | $1.9650e^{-05}$ | $5.0678e^{+04}$ | None |
| $2.4539e^{+08}$ | 0.0277 | 0.0121 | 974.4036 | 21.9983 | $1.6646e^{-05}$ | $5.9823e^{+04}$ | TPP Dissolving solution |
| $2.4995e^{+08}$ | 0.0097 | -0.0063 | 975.5816 | 23.1763 | $9.2365e^{-06}$ | $1.0781e^{+05}$ | Order |
| $2.5196e^{+08}$ | 0.0017 | -0.0144 | 976.0933 | 23.6880 | $7.1515e^{-06}$ | $1.3925e^{+05}$ | Protonation Time |
| $2.5203e^{+08}$ | 0.0014 | -0.0147 | 976.1125 | 23.7072 | $7.0832e^{-06}$ | $1.4059e^{+05}$ | Drug |
| $2.5222e^{+08}$ | $6.6606e^{-04}$ | -0.0155 | 976.1614 | 23.7561 | $6.9121e^{-06}$ | $1.4407e^{+05}$ | Synthesis Time |
| $2.5239e^{+08}$ | $5.0692e^{-07}$ | -0.0161 | 976.2040 | 23.7987 | $6.7664e^{-06}$ | $1.4717e^{+05}$ | Centrifugation |

FIG. 24

| AIC-based stepwise forward selection (RDA) | | | | | | |
|---|---|---|---|---|---|---|
| Marginal Tests: (sequential variable addition) | | | | | | |
| RSS | $R^2$ | $R^2$adj | AIC | Wts | DeltaN | Variables |
| $1.7401e^{+08}$ | 0.3105 | 0.2994 | 952.4053 | 0.9958 | 21.6665 | Ratio |
| $1.3499e^{+08}$ | 0.4652 | 0.4476 | 938.3569 | 0.8535 | 14.0484 | Wash/Reconstitution Solution |
| $1.1456e^{+08}$ | 0.5461 | 0.5234 | 930.1306 | 0.7613 | 8.2263 | Synthesis Time |
| $1.0698e^{+08}$ | 0.5761 | 0.5474 | 928.1074 | 0.2282 | 2.0232 | TPP Concentration |
| $1.0698e^{+08}$ | NaN | NaN | 928.1074 | 0.2034 | 0 | None |

FIG. 25

| Stepwise REDUNDANCY ANALYSIS | | | |
|---|---|---|---|
| Global Test: (all variables included) | | | |
| F | p | $R^2$ | $R^2$adj |
| 7.7013 | $1.0000e^{-03}$ | 0.6444 | 0.5607 |

FIG. 26

| Stepwise REDUNDANCY ANALYSIS | | | | |
| --- | --- | --- | --- | --- |
| Conditional Tests: (each variable separately) | | | | |
| F | p | $R^2$ | $R^2$adj | Variables |
| 13.6248 | 1.0000e$^{-03}$ | 0.1802 | 0.1669 | Chitosan Type |
| 4.1412 | 0.0540 | 0.0626 | 0.0475 | Chitosan Concentration |
| 3.2997 | 0.0790 | 0.0505 | 0.0352 | Chitosan Dissolving Solution |
| 0.1074 | 0.7450 | 0.0017 | -0.0144 | Protonation Time |
| 5.0296 | 0.0330 | 0.0750 | 0.0601 | TPP Concentration |
| 1.7689 | 0.1870 | 0.0277 | 0.0121 | TPP Dissolving solution |
| 0.0887 | 0.7730 | 0.0014 | -0.0147 | Drug |
| 0.6059 | 0.4250 | 0.0097 | -0.0063 | Order |
| 27.9262 | 1.0000e$^{-03}$ | 0.3105 | 0.2994 | Ratio |
| 0.0413 | 0.8440 | 6.6606e$^{-04}$ | -0.0155 | Synthesis Time |
| 3.1429e$^{-05}$ | 0.9950 | 5.0692e$^{-07}$ | -0.0161 | Centrifugation |
| 3.8295 | 0.0520 | 0.0582 | 0.0430 | Wash/Reconstitution Solution |

*FIG. 27*

| Stepwise REDUNDANCY ANALYSIS | | | | | |
| --- | --- | --- | --- | --- | --- |
| Marginal Tests: (sequential variable addition) | | | | | |
| Partial F | P | Partial $R^2$ | Partial $R^2$adj | Cum $R^2$adj | Variables |
| 27.9262 | 1.0000e$^{-03}$ | 0.3105 | 0.2994 | 0.2994 | Ratio |
| 17.6342 | 1.0000e$^{-03}$ | 0.1546 | 0.1410 | 0.4476 | Wash/Reconstitution Solution |
| 10.7019 | 0.0030 | 0.0810 | 0.0661 | 0.5234 | Synthesis Time |
| 4.1789 | 0.0500 | 0.0300 | 0.0144 | 0.5474 | TPP Concentration |

*FIG. 28*

| Multiple Linear Regression via QR Factorization | | | | |
|---|---|---|---|---|
| $R^2$ | $R^2adj$ | F-stat | Para-p | Perm-p |
| 0.57614 | 0.54740 | 20.04913 | 0.00000 | 0.00100 |

| Multiple Linear Regression via QR Factorization | | | | |
|---|---|---|---|---|
| Variables | b | t-stat | Parametric-p | Permutation-p |
| Intercept | 6820.73439 | 11.24915 | 0.00000 | 0.00200 |
| 1 | -1520.19243 | -7.86486 | 0.00000 | 0.00200 |
| 2 | -1383.24087 | -3.89756 | 0.00024 | 0.00200 |
| 3 | 2.19529 | 3.23940 | 0.00191 | 0.00200 |
| 4 | -1714.64471 | -2.04425 | 0.04511 | 0.02400 |

Table 1 (450 nm):

| | 1 | 2 | 3 | 4 | 5 | 6 | 7 | 8 | 9 | 10 | 11 | 12 |
|---|---|---|---|---|---|---|---|---|---|---|---|---|
| A | 0.278 | 0.287 | 0.261 | 0.58 | 0.626 | 0.621 | 0.976 | 1.009 | 0.914 | 1.703 | 1.766 | 1.814 |
| B | 0.275 | 0.3 | 0.299 | 0.297 | 0.294 | 0.303 | 0.282 | 0.288 | 0.29 | 0.291 | 0.287 | 0.227 |
| C | 0.379 | 0.378 | 0.427 | 0.55 | 0.628 | 0.567 | 0.871 | 0.915 | 0.953 | 0.282 | 0.285 | 0.28 |
| D | 0.405 | 0.384 | 0.384 | 0.485 | 0.524 | 0.65 | 0.719 | 0.792 | 0.158 | 0.799 | 0.654 | 0.64 |
| E | 0.512 | 0.537 | 0.653 | 1.035 | 0.953 | 1.02 | 1.47 | 1.546 | 1.451 | 0.809 | 0.9 | 0.86 |
| F | 0.597 | 0.532 | 0.525 | 0.884 | 0.892 | 0.946 | 1.557 | 1.519 | 1.488 | 1.377 | 1.651 | 1.47 |
| G | 0.048 | 0.05 | 0.047 | 0.047 | 0.047 | 0.05 | 0.047 | 0.048 | 0.047 | 0.047 | 0.047 | 0.046 |
| H | 0.048 | 0.048 | 0.048 | 0.047 | 0.047 | 0.046 | 0.046 | 0.046 | 0.047 | 0.047 | 0.047 | 0.046 |

Table 2 (490 nm):

| | 1 | 2 | 3 | 4 | 5 | 6 | 7 | 8 | 9 | 10 | 11 | 12 |
|---|---|---|---|---|---|---|---|---|---|---|---|---|
| A | 0.184 | 0.19 | 0.173 | 0.293 | 0.312 | 0.309 | 0.442 | 0.462 | 0.448 | 0.763 | 0.752 | 0.785 |
| B | 0.179 | 0.196 | 0.196 | 0.194 | 0.193 | 0.198 | 0.187 | 0.19 | 0.191 | 0.191 | 0.189 | 0.152 |
| C | 0.225 | 0.229 | 0.235 | 0.271 | 0.277 | 0.283 | 0.369 | 0.38 | 0.386 | 0.186 | 0.188 | 0.185 |
| D | 0.237 | 0.232 | 0.226 | 0.266 | 0.271 | 0.303 | 0.333 | 0.346 | 0.106 | 0.411 | 0.328 | 0.339 |
| E | 0.274 | 0.283 | 0.333 | 0.462 | 0.433 | 0.45 | 0.626 | 0.689 | 0.669 | 0.402 | 0.426 | 0.434 |
| F | 0.313 | 0.287 | 0.283 | 0.415 | 0.434 | 0.452 | 0.669 | 0.673 | 0.669 | 0.556 | 0.701 | 0.678 |
| G | 0.046 | 0.047 | 0.044 | 0.044 | 0.044 | 0.048 | 0.044 | 0.045 | 0.044 | 0.044 | 0.045 | 0.045 |
| H | 0.045 | 0.045 | 0.046 | 0.045 | 0.045 | 0.044 | 0.044 | 0.044 | 0.044 | 0.044 | 0.044 | 0.044 |

Table 3 (630 nm):

| | 1 | 2 | 3 | 4 | 5 | 6 | 7 | 8 | 9 | 10 | 11 | 12 |
|---|---|---|---|---|---|---|---|---|---|---|---|---|
| A | 0.051 | 0.051 | 0.047 | 0.049 | 0.05 | 0.05 | 0.051 | 0.053 | 0.052 | 0.054 | 0.055 | 0.053 |
| B | 0.051 | 0.053 | 0.052 | 0.05 | 0.053 | 0.053 | 0.053 | 0.052 | 0.05 | 0.05 | 0.05 | 0.046 |
| C | 0.053 | 0.054 | 0.053 | 0.054 | 0.054 | 0.053 | 0.056 | 0.058 | 0.056 | 0.05 | 0.05 | 0.05 |
| D | 0.055 | 0.054 | 0.053 | 0.055 | 0.052 | 0.056 | 0.056 | 0.057 | 0.042 | 0.068 | 0.052 | 0.053 |
| E | 0.05 | 0.051 | 0.053 | 0.054 | 0.055 | 0.053 | 0.056 | 0.057 | 0.057 | 0.054 | 0.055 | 0.053 |
| F | 0.054 | 0.059 | 0.052 | 0.052 | 0.043 | 0.054 | 0.054 | 0.055 | 0.056 | 0.052 | 0.056 | 0.055 |
| G | 0.043 | 0.045 | 0.041 | 0.041 | 0.044 | 0.045 | 0.042 | 0.042 | 0.041 | 0.042 | 0.043 | 0.043 |
| H | 0.043 | 0.042 | 0.042 | 0.042 | 0.044 | 0.043 | 0.042 | 0.041 | 0.043 | 0.041 | 0.043 | 0.041 |

| | 1 | 2 | 3 | 4 | 5 | 6 | 7 | 8 | 9 | 10 | 11 | 12 |
|---|---|---|---|---|---|---|---|---|---|---|---|---|
| A | 0.292 | 0.304 | 0.313 | 1.078 | 1.02 | 0.956 | 1.473 | 1.398 | 1.22 | 0.522 | 0.535 | 0.53 |
| B | 0.312 | 0.319 | 0.331 | 0.328 | 0.326 | 0.297 | 0.297 | 0.31 | 0.297 | 0.323 | 0.309 | 0.33 |
| C | 0.399 | 0.41 | 0.389 | 0.421 | 0.454 | 0.613 | 0.607 | 0.59 | 0.67 | 0.31 | 0.326 | 0.334 |
| D | 0.372 | 0.393 | 0.37 | 0.399 | 0.371 | 0.373 | 0.447 | 0.463 | 0.47 | 1.062 | 0.938 | 1.057 |
| E | 0.99 | 1.193 | 1.094 | 1.543 | 1.532 | 1.549 | 1.494 | 1.594 | 1.891 | 1.468 | 1.3 | 1.341 |
| F | 1.143 | 1.163 | 1.183 | 1.584 | 1.805 | 1.555 | 1.26 | 1.155 | 1.097 | 1.424 | 0.813 | 1.042 |
| G | 0.056 | 0.049 | 0.047 | 0.047 | 0.047 | 0.059 | 0.047 | 0.047 | 0.051 | 0.047 | 0.047 | 0.047 |
| H | 0.047 | 0.049 | 0.047 | 0.047 | 0.046 | 0.046 | 0.047 | 0.047 | 0.047 | 0.056 | 0.047 | 0.046 |

| | 1 | 2 | 3 | 4 | 5 | 6 | 7 | 8 | 9 | 10 | 11 | 12 |
|---|---|---|---|---|---|---|---|---|---|---|---|---|
| A | 0.183 | 0.19 | 0.192 | 0.497 | 0.494 | 0.481 | 0.675 | 0.658 | 0.591 | 0.271 | 0.275 | 0.275 |
| B | 0.193 | 0.196 | 0.201 | 0.198 | 0.197 | 0.19 | 0.19 | 0.195 | 0.192 | 0.202 | 0.188 | 0.2 |
| C | 0.248 | 0.233 | 0.223 | 0.23 | 0.241 | 0.311 | 0.279 | 0.287 | 0.309 | 0.195 | 0.204 | 0.204 |
| D | 0.222 | 0.225 | 0.219 | 0.226 | 0.217 | 0.221 | 0.238 | 0.252 | 0.251 | 0.444 | 0.419 | 0.511 |
| E | 0.455 | 0.484 | 0.468 | 0.663 | 0.648 | 0.642 | 0.657 | 0.702 | 0.754 | 0.641 | 0.587 | 0.634 |
| F | 0.517 | 0.502 | 0.522 | 0.683 | 0.726 | 0.649 | 0.535 | 0.513 | 0.493 | 0.612 | 0.383 | 0.495 |
| G | 0.054 | 0.047 | 0.044 | 0.044 | 0.044 | 0.057 | 0.045 | 0.045 | 0.048 | 0.045 | 0.045 | 0.045 |
| H | 0.044 | 0.046 | 0.045 | 0.045 | 0.044 | 0.045 | 0.045 | 0.045 | 0.045 | 0.053 | 0.044 | 0.044 |

| | 1 | 2 | 3 | 4 | 5 | 6 | 7 | 8 | 9 | 10 | 11 | 12 |
|---|---|---|---|---|---|---|---|---|---|---|---|---|
| A | 0.048 | 0.05 | 0.046 | 0.051 | 0.051 | 0.05 | 0.056 | 0.057 | 0.055 | 0.055 | 0.053 | 0.054 |
| B | 0.049 | 0.051 | 0.05 | 0.048 | 0.048 | 0.049 | 0.049 | 0.049 | 0.047 | 0.049 | 0.048 | 0.05 |
| C | 0.077 | 0.053 | 0.052 | 0.051 | 0.05 | 0.061 | 0.052 | 0.053 | 0.051 | 0.049 | 0.052 | 0.05 |
| D | 0.054 | 0.052 | 0.052 | 0.052 | 0.053 | 0.052 | 0.049 | 0.053 | 0.053 | 0.051 | 0.051 | 0.054 |
| E | 0.053 | 0.052 | 0.051 | 0.054 | 0.055 | 0.054 | 0.057 | 0.062 | 0.063 | 0.057 | 0.057 | 0.056 |
| F | 0.055 | 0.052 | 0.051 | 0.057 | 0.056 | 0.054 | 0.058 | 0.069 | 0.062 | 0.057 | 0.058 | 0.06 |
| G | 0.049 | 0.044 | 0.041 | 0.041 | 0.043 | 0.054 | 0.043 | 0.042 | 0.044 | 0.043 | 0.043 | 0.043 |
| H | 0.041 | 0.042 | 0.041 | 0.042 | 0.043 | 0.043 | 0.042 | 0.042 | 0.042 | 0.05 | 0.042 | 0.042 |

| | 1 | 2 | 3 | 4 | 5 | 6 | 7 | 8 | 9 | 10 | 11 | 12 | |
|---|---|---|---|---|---|---|---|---|---|---|---|---|---|
| A | 0.458 | 0.464 | 0.438 | 1.268 | 1.065 | 1.044 | 0.631 | 0.564 | 0.609 | 0.869 | 0.935 | 0.842 | 480 |
| B | 0.474 | 0.462 | 0.38 | 0.4 | 0.423 | 0.382 | 0.429 | 0.409 | 0.423 | 0.424 | 0.445 | 0.436 | 480 |
| C | 0.52 | 0.489 | 0.428 | 0.422 | 0.455 | 0.432 | 0.503 | 0.495 | 0.491 | 0.44 | 0.451 | 0.384 | 480 |
| D | 0.527 | 0.46 | 0.441 | 0.442 | 0.433 | 0.445 | 0.429 | 0.484 | 0.461 | 1.649 | 1.311 | 1.448 | 480 |
| E | 1.697 | 1.997 | 1.652 | 1.475 | 1.384 | 1.441 | 1.366 | 1.292 | 1.166 | 1.393 | 0.864 | 1.402 | 480 |
| F | 1.872 | 1.871 | 1.696 | 0.925 | 1.624 | 2.019 | 1.05 | 1.057 | 0.937 | 0.868 | 0.864 | 0.904 | 480 |
| G | 0.047 | 0.047 | 0.049 | 0.048 | 0.047 | 0.047 | 0.047 | 0.047 | 0.047 | 0.049 | 0.048 | 0.046 | 480 |
| H | 0.049 | 0.047 | 0.049 | 0.046 | 0.048 | 0.046 | 0.046 | 0.046 | 0.046 | 0.048 | 0.048 | 0.049 | 480 |

| | 1 | 2 | 3 | 4 | 5 | 6 | 7 | 8 | 9 | 10 | 11 | 12 | |
|---|---|---|---|---|---|---|---|---|---|---|---|---|---|
| A | 0.281 | 0.279 | 0.263 | 0.64 | 0.536 | 0.565 | 0.356 | 0.307 | 0.338 | 0.492 | 0.538 | 0.422 | 490 |
| B | 0.287 | 0.281 | 0.257 | 0.25 | 0.255 | 0.247 | 0.262 | 0.254 | 0.262 | 0.267 | 0.262 | 0.265 | 490 |
| C | 0.31 | 0.289 | 0.281 | 0.251 | 0.281 | 0.281 | 0.295 | 0.281 | 0.287 | 0.27 | 0.274 | 0.229 | 490 |
| D | 0.319 | 0.299 | 0.271 | 0.289 | 0.27 | 0.278 | 0.255 | 0.293 | 0.286 | 0.664 | 0.587 | 0.672 | 490 |
| E | 0.768 | 0.865 | 0.722 | 0.656 | 0.672 | 0.624 | 0.611 | 0.571 | 0.53 | 0.614 | 0.43 | 0.656 | 490 |
| F | 0.841 | 0.815 | 0.757 | 0.459 | 0.712 | 0.862 | 0.481 | 0.505 | 0.467 | 0.441 | 0.441 | 0.445 | 490 |
| G | 0.045 | 0.045 | 0.046 | 0.045 | 0.045 | 0.045 | 0.045 | 0.045 | 0.045 | 0.046 | 0.046 | 0.044 | 490 |
| H | 0.046 | 0.044 | 0.046 | 0.044 | 0.046 | 0.044 | 0.044 | 0.044 | 0.044 | 0.045 | 0.045 | 0.047 | 490 |

| | 1 | 2 | 3 | 4 | 5 | 6 | 7 | 8 | 9 | 10 | 11 | 12 | |
|---|---|---|---|---|---|---|---|---|---|---|---|---|---|
| A | 0.059 | 0.056 | 0.053 | 0.065 | 0.068 | 0.068 | 0.068 | 0.063 | 0.059 | 0.119 | 0.144 | 0.061 | 530 |
| B | 0.059 | 0.059 | 0.055 | 0.053 | 0.055 | 0.054 | 0.056 | 0.057 | 0.055 | 0.055 | 0.056 | 0.055 | 530 |
| C | 0.062 | 0.059 | 0.058 | 0.052 | 0.057 | 0.058 | 0.06 | 0.06 | 0.058 | 0.056 | 0.058 | 0.051 | 530 |
| D | 0.064 | 0.063 | 0.06 | 0.061 | 0.059 | 0.056 | 0.057 | 0.059 | 0.062 | 0.061 | 0.065 | 0.06 | 530 |
| E | 0.065 | 0.067 | 0.066 | 0.072 | 0.07 | 0.071 | 0.083 | 0.059 | 0.082 | 0.072 | 0.07 | 0.068 | 530 |
| F | 0.065 | 0.068 | 0.064 | 0.069 | 0.064 | 0.061 | 0.054 | 0.057 | 0.059 | 0.061 | 0.066 | 0.071 | 530 |
| G | 0.041 | 0.043 | 0.042 | 0.043 | 0.043 | 0.042 | 0.043 | 0.042 | 0.041 | 0.044 | 0.043 | 0.043 | 530 |
| H | 0.044 | 0.04 | 0.043 | 0.041 | 0.044 | 0.043 | 0.042 | 0.041 | 0.041 | 0.041 | 0.043 | 0.043 | 530 |

450

| 1 | 2 | 3 | 4 | 5 | 6 | 7 | 8 | 9 | 10 | 11 | 12 |
|---|---|---|---|---|---|---|---|---|----|----|----|
| 0.148 | 0.179 | 0.191 | 0.835 | 0.851 | 0.83 | 0.838 | 1.006 | 0.796 | 1.613 | 1.668 | 1.58 |
| 0.195 | 0.181 | 0.192 | 0.207 | 0.202 | 0.207 | 0.206 | 0.197 | 0.196 | 0.202 | 0.197 | 0.195 |
| 0.557 | 0.632 | 0.627 | 0.636 | 0.642 | 0.595 | 0.951 | 0.994 | 0.957 | 0.196 | 0.189 | 0.198 |
| 0.497 | 0.473 | 0.491 | 0.492 | 0.524 | 0.5 | 0.828 | 0.739 | 0.648 | 0.83 | 0.72 | 0.663 |
| 0.676 | 0.805 | 0.749 | 0.723 | 0.766 | 0.72 | 1.408 | 1.142 | 1.28 | 0.916 | 0.734 | 0.711 |
| 0.612 | 0.529 | 0.66 | 0.666 | 0.758 | 0.694 | 1.111 | 1.136 | 1.05 | 1.241 | 1.538 | 1.109 |
| 0.047 | 0.047 | 0.047 | 0.047 | 0.047 | 0.047 | 0.047 | 0.047 | 0.053 | 0.047 | 0.047 | 0.047 |
| 0.047 | 0.047 | 0.047 | 0.046 | 0.047 | 0.046 | 0.047 | 0.047 | 0.046 | 0.047 | 0.047 | 0.047 |

490

| 1 | 2 | 3 | 4 | 5 | 6 | 7 | 8 | 9 | 10 | 11 | 12 |
|---|---|---|---|---|---|---|---|---|----|----|----|
| 0.106 | 0.126 | 0.134 | 0.392 | 0.393 | 0.385 | 0.409 | 0.457 | 0.375 | 0.666 | 0.712 | 0.668 |
| 0.134 | 0.127 | 0.136 | 0.143 | 0.14 | 0.142 | 0.149 | 0.141 | 0.14 | 0.142 | 0.14 | 0.143 |
| 0.263 | 0.288 | 0.301 | 0.312 | 0.304 | 0.292 | 0.412 | 0.416 | 0.442 | 0.14 | 0.136 | 0.142 |
| 0.258 | 0.248 | 0.252 | 0.264 | 0.265 | 0.253 | 0.373 | 0.347 | 0.312 | 0.388 | 0.337 | 0.326 |
| 0.311 | 0.354 | 0.341 | 0.326 | 0.35 | 0.327 | 0.589 | 0.517 | 0.557 | 0.426 | 0.345 | 0.351 |
| 0.296 | 0.249 | 0.325 | 0.325 | 0.358 | 0.336 | 0.47 | 0.525 | 0.465 | 0.538 | 0.649 | 0.478 |
| 0.045 | 0.045 | 0.044 | 0.044 | 0.044 | 0.045 | 0.044 | 0.044 | 0.051 | 0.045 | 0.045 | 0.044 |
| 0.044 | 0.045 | 0.044 | 0.044 | 0.044 | 0.044 | 0.045 | 0.044 | 0.044 | 0.044 | 0.044 | 0.044 |

630

| 1 | 2 | 3 | 4 | 5 | 6 | 7 | 8 | 9 | 10 | 11 | 12 |
|---|---|---|---|---|---|---|---|---|----|----|----|
| 0.039 | 0.039 | 0.038 | 0.042 | 0.041 | 0.041 | 0.045 | 0.046 | 0.041 | 0.043 | 0.045 | 0.045 |
| 0.04 | 0.04 | 0.04 | 0.039 | 0.04 | 0.041 | 0.048 | 0.04 | 0.04 | 0.039 | 0.039 | 0.041 |
| 0.042 | 0.042 | 0.042 | 0.042 | 0.042 | 0.041 | 0.044 | 0.043 | 0.044 | 0.04 | 0.039 | 0.041 |
| 0.043 | 0.042 | 0.042 | 0.044 | 0.044 | 0.042 | 0.043 | 0.043 | 0.045 | 0.044 | 0.042 | 0.041 |
| 0.041 | 0.042 | 0.042 | 0.043 | 0.041 | 0.043 | 0.043 | 0.044 | 0.045 | 0.043 | 0.042 | 0.042 |
| 0.041 | 0.043 | 0.044 | 0.042 | 0.046 | 0.042 | 0.043 | 0.054 | 0.044 | 0.044 | 0.044 | 0.045 |
| 0.043 | 0.042 | 0.041 | 0.042 | 0.043 | 0.042 | 0.042 | 0.041 | 0.048 | 0.043 | 0.042 | 0.043 |
| 0.042 | 0.04 | 0.041 | 0.041 | 0.042 | 0.042 | 0.042 | 0.041 | 0.041 | 0.042 | 0.042 | 0.042 |

|   | 1 | 2 | 3 | 4 | 5 | 6 | 7 | 8 | 9 | 10 | 11 | 12 |
|---|---|---|---|---|---|---|---|---|---|----|----|----|
| A | 0.186 | 0.189 | 0.191 | 1.621 | 1.837 | 2.17 | 1.789 | 2.469 | 2.908 | 2.321 | 2.086 | 2.275 |
| B | 0.259 | 0.278 | 0.274 | 0.292 | 0.28 | 0.286 | 0.275 | 0.272 | 0.265 | 0.273 | 0.281 | 0.265 |
| C | 1.161 | 0.965 | 0.962 | 0.944 | 1.28 | 1.154 | 1.708 | 1.616 | 1.348 | 0.277 | 0.271 | 0.28 |
| D | 0.404 | 0.461 | 0.495 | 0.471 | 0.578 | 0.57 | 0.747 | 0.833 | 0.886 | 1.488 | 1.93 | 1.425 |
| E | 1.941 | 1.812 | 2.135 | 1.526 | 1.658 | 1.68 | 2.705 | 2.63 | 2.916 | 1.626 | 1.878 | 1.437 |
| F | 0.907 | 1.081 | 1.025 | 0.89 | 0.965 | 0.922 | 1.735 | 1.408 | 1.537 | 2.07 | 1.815 | 2.013 |
| G | 0.048 | 0.047 | 0.061 | 0.048 | 0.047 | 0.047 | 0.047 | 0.05 | 0.049 | 0.052 | 0.047 | 0.048 |
| H | 0.047 | 0.046 | 0.047 | 0.049 | 0.047 | 0.05 | 0.046 | 0.047 | 0.047 | 0.048 | 0.047 | 0.047 |

480 nm:

|   | 1 | 2 | 3 | 4 | 5 | 6 | 7 | 8 | 9 | 10 | 11 | 12 |
|---|---|---|---|---|---|---|---|---|---|----|----|----|
| A | 0.132 | 0.134 | 0.135 | 0.765 | 0.775 | 0.847 | 0.831 | 0.938 | 0.939 | 0.902 | 0.854 | 0.955 |
| B | 0.171 | 0.187 | 0.183 | 0.194 | 0.184 | 0.19 | 0.19 | 0.186 | 0.182 | 0.187 | 0.192 | 0.181 |
| C | 0.515 | 0.425 | 0.472 | 0.381 | 0.5 | 0.436 | 0.607 | 0.555 | 0.562 | 0.189 | 0.183 | 0.194 |
| D | 0.227 | 0.245 | 0.24 | 0.244 | 0.262 | 0.284 | 0.339 | 0.329 | 0.359 | 0.591 | 0.796 | 0.628 |
| E | 0.764 | 0.742 | 0.808 | 0.597 | 0.656 | 0.755 | 1.041 | 1.079 | 1.192 | 0.714 | 0.788 | 0.641 |
| F | 0.399 | 0.444 | 0.419 | 0.331 | 0.42 | 0.393 | 0.759 | 0.601 | 0.847 | 0.88 | 0.792 | 0.874 |
| G | 0.045 | 0.045 | 0.057 | 0.045 | 0.045 | 0.045 | 0.045 | 0.047 | 0.046 | 0.05 | 0.046 | 0.046 |
| H | 0.044 | 0.044 | 0.044 | 0.046 | 0.044 | 0.047 | 0.044 | 0.044 | 0.046 | 0.045 | 0.045 | 0.045 |

630 nm:

|   | 1 | 2 | 3 | 4 | 5 | 6 | 7 | 8 | 9 | 10 | 11 | 12 |
|---|---|---|---|---|---|---|---|---|---|----|----|----|
| A | 0.04 | 0.04 | 0.039 | 0.045 | 0.044 | 0.048 | 0.049 | 0.047 | 0.047 | 0.051 | 0.054 | 0.053 |
| B | 0.042 | 0.043 | 0.042 | 0.041 | 0.042 | 0.042 | 0.044 | 0.043 | 0.042 | 0.042 | 0.042 | 0.042 |
| C | 0.046 | 0.045 | 0.047 | 0.046 | 0.047 | 0.044 | 0.05 | 0.05 | 0.048 | 0.042 | 0.043 | 0.043 |
| D | 0.043 | 0.045 | 0.044 | 0.044 | 0.044 | 0.042 | 0.045 | 0.044 | 0.055 | 0.058 | 0.048 | 0.046 |
| E | 0.047 | 0.046 | 0.047 | 0.045 | 0.044 | 0.047 | 0.052 | 0.057 | 0.052 | 0.056 | 0.047 | 0.046 |
| F | 0.046 | 0.048 | 0.05 | 0.046 | 0.045 | 0.045 | 0.05 | 0.051 | 0.053 | 0.055 | 0.054 | 0.046 |
| G | 0.043 | 0.042 | 0.051 | 0.043 | 0.043 | 0.042 | 0.043 | 0.044 | 0.043 | 0.046 | 0.043 | 0.044 |
| H | 0.043 | 0.04 | 0.04 | 0.044 | 0.043 | 0.045 | 0.041 | 0.041 | 0.041 | 0.043 | 0.042 | 0.043 |

Plate 1 (450)

|   | 1 | 2 | 3 | 4 | 5 | 6 | 7 | 8 | 9 | 10 | 11 | 12 |
|---|---|---|---|---|---|---|---|---|---|----|----|----|
| A | 0.401 | 0.395 | 0.389 | 1.246 | 0.87 | 1.186 | 0.921 | 0.85 | 0.812 | 1.202 | 1.04 | 0.927 |
| B | 0.389 | 0.393 | 0.376 | 0.38 | 0.382 | 0.38 | 0.362 | 0.372 | 0.361 | 0.363 | 0.373 | 0.353 |
| C | 0.825 | 0.834 | 0.82 | 0.785 | 0.815 | 0.962 | 1.085 | 0.989 | 0.842 | 0.375 | 0.379 | 0.381 |
| D | 0.423 | 0.435 | 0.431 | 0.44 | 0.43 | 0.448 | 0.587 | 0.461 | 0.467 | 1.271 | 3.073 | 2.811 |
| E | 2.572 | 2.343 | 2.432 | 2.172 | 2.324 | 2.223 | 2.326 | 0.815 | 0.965 | 1.169 | 1.25 | 1.088 |
| F | 1.358 | 1.442 | 1.141 | 1.474 | 1.525 | 1.29 | 1.282 | 0.874 | 1.198 | 1.173 | 0.868 | 1.012 |
| G | 0.047 | 0.048 | 0.048 | 0.047 | 0.05 | 0.048 | 0.057 | 0.049 | 0.062 | 0.048 | 0.048 | 0.048 |
| H | 0.047 | 0.048 | 0.047 | 0.048 | 0.047 | 0.047 | 0.051 | 0.047 | 0.047 | 0.047 | 0.047 | 0.048 |

Plate 2 (490)

|   | 1 | 2 | 3 | 4 | 5 | 6 | 7 | 8 | 9 | 10 | 11 | 12 |
|---|---|---|---|---|---|---|---|---|---|----|----|----|
| A | 0.273 | 0.269 | 0.267 | 0.54 | 0.402 | 0.482 | 0.456 | 0.449 | 0.43 | 0.598 | 0.551 | 0.477 |
| B | 0.274 | 0.274 | 0.259 | 0.26 | 0.263 | 0.261 | 0.255 | 0.262 | 0.254 | 0.256 | 0.262 | 0.242 |
| C | 0.401 | 0.419 | 0.409 | 0.441 | 0.405 | 0.438 | 0.503 | 0.618 | 0.464 | 0.266 | 0.268 | 0.27 |
| D | 0.288 | 0.284 | 0.304 | 0.299 | 0.299 | 0.294 | 0.33 | 0.304 | 0.305 | 0.609 | 1.401 | 1.23 |
| E | 0.989 | 1.913 | 1.953 | 1.904 | 2.059 | 2.047 | 1.114 | 0.515 | 0.53 | 0.518 | 0.663 | 0.541 |
| F | 0.652 | 0.696 | 0.571 | 0.571 | 0.684 | 0.503 | 0.757 | 0.503 | 0.844 | 0.603 | 0.498 | 0.522 |
| G | 0.044 | 0.045 | 0.045 | 0.045 | 0.044 | 0.045 | 0.053 | 0.046 | 0.058 | 0.045 | 0.046 | 0.045 |
| H | 0.044 | 0.045 | 0.045 | 0.045 | 0.044 | 0.045 | 0.048 | 0.045 | 0.045 | 0.044 | 0.044 | 0.045 |

Plate 3 (630)

|   | 1 | 2 | 3 | 4 | 5 | 6 | 7 | 8 | 9 | 10 | 11 | 12 |
|---|---|---|---|---|---|---|---|---|---|----|----|----|
| A | 0.044 | 0.045 | 0.044 | 0.05 | 0.049 | 0.051 | 0.054 | 0.055 | 0.05 | 0.059 | 0.061 | 0.059 |
| B | 0.046 | 0.047 | 0.045 | 0.044 | 0.045 | 0.047 | 0.047 | 0.047 | 0.045 | 0.045 | 0.044 | 0.044 |
| C | 0.049 | 0.049 | 0.049 | 0.048 | 0.049 | 0.049 | 0.052 | 0.051 | 0.052 | 0.047 | 0.046 | 0.046 |
| D | 0.048 | 0.049 | 0.049 | 0.05 | 0.05 | 0.047 | 0.048 | 0.051 | 0.052 | 0.052 | 0.05 | 0.052 |
| E | 0.053 | 0.076 | 0.057 | 0.058 | 0.084 | 0.086 | 0.066 | 0.061 | 0.061 | 0.056 | 0.056 | 0.055 |
| F | 0.049 | 0.046 | 0.049 | 0.055 | 0.052 | 0.05 | 0.058 | 0.064 | 0.059 | 0.059 | 0.059 | 0.053 |
| G | 0.042 | 0.042 | 0.041 | 0.042 | 0.042 | 0.042 | 0.049 | 0.044 | 0.053 | 0.043 | 0.043 | 0.044 |
| H | 0.043 | 0.041 | 0.041 | 0.043 | 0.042 | 0.043 | 0.044 | 0.042 | 0.04 | 0.043 | 0.042 | 0.043 |

*FIG. 37*

DEVICE FOR STERILE UTERINE SAMPLING AND DRUG DELIVERY

CROSS REFERENCE TO RELATED APPLICATIONS

This application is a nonprovisional of and claims priority to U.S. Provisional Patent Application No. 61/740,677, entitled "Sterile Uterine Sample Cover", filed Dec. 21, 2012, the entire contents of which is herein incorporated into this disclosure.

FIELD OF INVENTION

This invention relates to sampling devices for use in the female reproductive system. Specifically, the invention provides a sterile uterine sampler cover that is used to collect uncontaminated samples from the uterus and deliver treatment drugs to the uterus.

BACKGROUND OF THE INVENTION

Uterus Sampling Devices

Devices that can be inserted into the uterus have been developed for endometrial sampling, pregnancy prevention, and other gynecological procedures. Examples include the select cell, transcervical devices, intrauterine devices (IUDs), and curettes. IUDs are small devices implanted into the uterus for a certain period of time to prevent pregnancy by disrupting the uterine wall or slowly releasing hormones. (Stubbs E, Schamp A. The evidence is in. Why are IUDs still out? Family physicians' perceptions of risk and indications. *Can Fam Physician.* 2008; 54(4):560-566; Heinberg E M, McCoy T W, Pasic R. The Perforated Intrauterine Device: Endoscopic Retrieval. *JSLS.* 2008; 12(1):97-100; The ESHRE Capri Workshop Group. Intrauterine devices and intrauterine systems. *Human Reproduction Update.* 2008; 14(3):197-200). The curette is a metal rod with a handle at one end and a loop on the other end that is used to scrape the lining of the uterus during a gynecological procedure called "dilation and curettage". (Humber N. The occasional D & C. *Can J Rural Med.* 2009; 14(3):115-118). This procedure was considered the gold standard for sampling the endometrium for more than a century. (Chambers J T, Chambers S K. Endometrial Sampling: When? Where? Why? With What? *Clinical Obstetrics and Gynecology.* 1992; 35(1):28-39; Cooper J M, Erickson M L. Endmetrial Sampling Techniques in the Diagnosis of Abnormal Uterine Bleeding. *Obstetrics and Gynecology Clinics of North America.* 2000; 27(2):235-244)

In 1949, Guilbeau et al. proposed a uterine culture technique for sampling the endometrium of postpartum women while avoiding the contaminated cervical and vaginal areas. (Guilbeau J A, Schaub I G. Uterine Culture Technique: A simple Method for Avoiding Contamination by the Cervical and Vaginal Flora. *American Journal of Obstetrics & Gynecology.* 1949:407-410; Knuppel R, Scerbo J, Dzink J, Mitchell G, Cetrulo C, Barlett J. Quantitive Transcervical Uterine Cultures With a New Device. *Obstetrics and Gynecology.* 1981; 57:243-247; Duff P, Gibbs R, Blanco J, St. Clair P. Endometrial Culture Techniques in Puerperal Patients. *Obstetrics and Gynecology.* 1983; 61(2):217-222). They suggested using a metal tube with a tightly drawn finger cot (which required chemical sterilization for 48 hours) to occlude the distal end of the cervix and prevent contamination during insertion. Once inserted with a stylet beyond the internal os of the cervix, the finger cot was pierced, thus allowing the inner wire loop to collect the sample. However, this technique was merely described; no data were presented to document its efficacy.

In 1981, Knuppel et al. presented a transcervical device for sampling the uterus. (Knuppel R, Scerbo J, Dzink J, Mitchell G, Cetrulo C, Barlett J. Quantitive Transcervical Uterine Cultures With a New Device. *Obstetrics and Gynecology.* 1981; 57:243-247). This specimen collection device consisted of a telescoping Teflon catheter that housed a nylon bristle brush attached to a retractable wire in the inner cannula. At the tip of the outer catheter was a plug made of either gelfoam or polyethylene glycol. Upon insertion of the device, the brush was used to push the plug into the uterus to allow the brush to collect the specimen. Leaving the plug in the uterus was a major drawback. A plug made of polyethylene glycol would take a couple of days to dissolve; a plug made of gelfoam could cause a nidus of infection. This device was designed to pass through the contaminated vaginal and cervical area to the uterus for specimen collection. This device does not protect the uterine sample from the contaminated vagina and cervix, and it leaves the plug portion of the device inside the uterus.

Another technique for culturing the uterus was described by Bollinger. (Duff P, Gibbs R, Blanco J, St. Clair P. Endometrial Culture Techniques in Puerperal Patients. *Obstetrics and Gynecology.* 1983; 61(2):217-222; Bollinger C C. Bacterial Flora of the Nonpregnant Uterus: A New Culture Technic. *Obstetrics and Gynecology.* 1964; 23(2): 251-255). In this technique, a Teflon sheath with a Teflon plug was used to reach the uterus. Once inside the uterus, the plug was dislodged by an inner cannula to which a syringe was attached for suction of the specimen sample. The accuracy of this approach was not clearly defined due to the fact that the device used for sampling passes through the contaminated areas of the cervix and vagina.

Between 1981 and 1982, Patrick Duff and his team investigated four different endometrial specimen techniques: (1) transfundal aspiration, (2) transcervical brush biopsy through a double-lumen catheter, (3) transcervical lavage through a double-lumen catheter, and (4) aspiration of secretions from the lower uterine segment through a single-lumen catheter. (Duff P, Gibbs R, Blanco J, St. Clair P. Endometrial Culture Techniques in Puerperal Patients. *Obstetrics and Gynecology.* 1983; 61(2):217-222). For the transfundal aspiration, an 18-gauge spinal needle preloaded with sterile polyionic solution is used. Once in the endometrium cavity, the solution was injected through the needle and then immediately aspirated back into the needle. Knuppel et al described the transcervical double-lumen catheter technique. (Knuppel R, Scerbo J, Dzink J, Mitchell G, Cetrulo C, Barlett J. Quantitive Transcervical Uterine Cultures With a New Device. *Obstetrics and Gynecology.* 1981; 57:243-247; Duff P, Gibbs R, Blanco J, St. Clair P. Endometrial Culture Techniques in Puerperal Patients. *Obstetrics and Gynecology.* 1983; 61(2):217-222). For the transcervical lavage, a sterile polyionic solution was injected in the endometrium cavity through an inner catheter passing through an outer catheter. This injection was followed by immediate re-aspiration. For the fourth technique, aspiration of lower-uterine secretions, a catheter was placed 4 cm above the external os of the cervix and a polyionic solution was then injected and immediately re-aspirated. These techniques were all conducted on uninfected women in the Trendelenburg position. It was observed that the brush biopsy and lavage through double-lumen catheter were the most satisfactory techniques for reducing but not preventing cervical and vaginal contamination.

The select cell, a newer and smaller version of the Pipelle, is another device used to collect endometrial specimens. (Chambers J T, Chambers S K. Endometrial Sampling: When? Where? Why? With What? *Clinical Obstetrics and Gynecology.* 1992; 35(1):28-39). The select cell, which removes specimens through suction, is made of a clear, long, and flexible polypropylene sheath with an acetyl copolymer rod to which a piston is molded. As with the transcervical devices, the specimen collected by the select cell is not protected from the contaminated vaginal and cervical areas during sampling.

Several other endometrium samplers and/or techniques have been patented including those described in U.S. Pat. No. 3,777,743 to Binard et al.; U.S. Pat. No. 4,340,066 to Shah; U.S. Pat. No. 4,393,879 to Milgrom; U.S. Pat. No. 4,441,509 to Kotsifas et al.; U.S. Pat. No. 4,949,718 to Neuwirth et al.; U.S. Pat. No. 6,514,224 to Anapliotis; U.S. Pat. No. 8,528,563 to Gruber; U.S. Pat. No. 7,879,559 to Alderete et al.; and U.S. Pat. No. 8,048,101 to Lee-Sepsick et al. However, none of the currently available or patented devices and/or techniques can procure truly uncontaminated specimen samples from the endometrium and surrounding areas. Sterile samples are necessary for a better understanding of not only normal flora in asymptomatic women but also improved understanding and diagnosis of upper genital tract infection in symptomatic women.

The inventors have developed a novel sterile uterine sampler cover (SUSC) device to collect sterile specimen samples from the fallopian tubes, uterus, and surrounding areas to improve the accuracy of diagnosis of pelvic inflammatory disease (PID). Once the disease-causing organism(s) are identified, the proper drug treatment can be recognized. To improve the treatment drug's efficacy, the drug can be encapsulated into nanoparticles for targeted drug delivery. This device can also be used to deliver drug-loaded particles via a transcervical route for more localized drug treatment of PID.

Targeted Drug Delivery

Targeted drug delivery is a unique method for delivering a drug to one particular site of the body in an effort to increase the dosage to that specific location and to reduce adverse side effects. There are three main constituents in a targeted drug delivery system: a drug, a targeted site, and a delivery vehicle. (Patel M P, Patel R R, Patel J K. Chitosan Mediated Drug delivery System: A Review. *J Pharm Pharmaceut Sci* 2010; 13(3):536-557). The drug can be either chemically conjugated or passively absorbed into the delivery vehicle. The targeted site is dictated by the nature and origin of the disease being treated. The delivery vehicle (the carrier) is of utmost importance, as it must preserve the pharmacodynamic and pharmacokinetic properties of the drug being carried. (Patel M P, Patel R R, Patel J K. Chitosan Mediated Drug delivery System: A Review. *J Pharm Pharmaceut Sci* 2010; 13(3):536-557).

To deliver a drug across cell membranes, several vehicle materials can be used—e.g., natural or synthetic polymers, dendrimers, surfactants, or lipids. (Sampathkumar S G, Yarem K J. Targeting Cancer Cells Dendrimer. *Chemistry & Biology.* 2005; 12:5-13; Duncan R. The Dawning Era of Polymer Therapeutic. *Nature Reviews Drug Discovery.* 2003; 2:347-360; Torchilin V. Antibody-modified liposomes for Cancer Chemotherapy. *Expert Opin. Drug Deliv.* 2008; 5(9):1003-1025). Among the natural polymers, chitosan is widely used in drug delivery applications because it is biocompatible, biodegradable, and possesses a muco-adhesive property that enables its transport across mucosal membranes. These properties make chitosan highly desirable for encapsulating drugs to improve their efficiency, delivery, and controlled release, and thereby reduce their toxicity. (Zhang H, Oh M, Allen C, Kumacheva E. Monodisperse Chitosan Nanoparticles for Mucosal Drug Delivery. *Biomacromolecules.* 2004:2461-2468; Xi-Peng G, Da-Ping Q, Kai-Rong L, Tao W, Peng X, Mai K C. Preparation and Characterization of Cationic Chitosan-modified Poly(D,L-lactide-co-glycolide) Copolymer Nanospheres as DNA Carriers. *J Biomater Appl.* 2007:353-370; Goycoolea F M, Lollo G, Remunan-Lopez G, Quaglia F, Alonso M J. Chitosan-Alginate Blended Nanoparticles as Carriers for the Transmucosal Delivery of Macromolecules. *Biomacromolecules.* 2009; 10:1736-1743; Zhang H, Wu S, Tao Y, Zang L, Su Z. Preparation and Characterization of Water-Soluble Chitosan Nanoparticles as Protein Delivery System. *Journal of Nanomaterials.* 2009; 2010:1-5; Racovita S, Vasiliu S, Popa M, Luca C. Polysaccharides based on micro- and nanoparticles obtained by ionic gelation and their application as drug delivery systems. *Revue Roumaine de Chimie.* 2009; 54(9): 709-718; Janes K A, Clavo P, Alonso M J. Polysaccharide colloidal particles as delivery systems for macromolecule. *Adv Drug Deliv Rev.* 2001; 47:83-97; Patel J K, Jivani N P. Chitosan Based Nanoparticles in Drug Delivery. *International Journal of Pharmaceutical Sciences and Nanotechnology.* 2009; 2(2):517-522; Muhammed R, Junise V, Saraswathi P, Krishnan P, Dilip C. Development and characterization of chitosan nanoparticles loaded with isoniazid for the treatment of Tuberculosis. *Research Journal of Pharmaceutical, Biological and Chemical Sciences.* 2010: 383-390; Phaechamud T, Charoenteeraboon J. Antibacterial Activity and Drug Release of the Chitosan Sponge Containing Hyclate. AAPS Pharm Sci Tech. 2008; 9(3):829-835; Ko J A, Park H J, Hwang S J, Park J B, Lee J S. Preparation and Characterization of Chitosan Microparticles intended for Controlled Drug Delivery. *International Journal of Pharmaceutics.* 2002:165-174)

Chitosan is a cationic linear amino-polysaccharide biopolymer derived from the deacetylation of chitin (FIG. 1), which is naturally found in the exoskeleton of crustaceans. (Zhang H, Oh M, Allen C, Kumacheva E. Monodisperse Chitosan Nanoparticles for Mucosal Drug Delivery. *Biomacromolecules.* 2004:2461-2468; Racovita S, Vasiliu S, Popa M, Luca C. Polysaccharides based on micro- and nanoparticles obtained by ionic gelation and their application as drug delivery systems. *Revue Roumaine de Chimie.* 2009; 54(9):709-718; Patel J K, Jivani N P. Chitosan Based Nanoparticles in Drug Delivery. *International Journal of Pharmaceutical Sciences and Nanotechnology.* 2009; 2(2): 517-522; Sarmento B, Ribeiro A, Veiga F, Ferreira D. Development and characterization of new insulin containing polysaccharide nanoparticle. *Colloids and Surfaces B: Biointerface.* 2006; 53:193-202; Tokumitsu H, Ichikawa H, Fukumori Y. Chitosan-Gadopentetic Acid Complex Nanoparticles for Gadolinium Neutron-Capture Therapy Therapy of Cancer: Preparation by Novel Emulsion-Droplet Coalescence Technique and Characterization. *Pharmaceutical Research.* 1999; 16(12):1830-1835; Pawan P, Mayur M, Ashwin S. Role of Natural Polymers in Sustained Release Drug Delivery System: Application and Recent Approaches. *International Research Journal of Pharmacy.* 2011; 2(9):6-11; Liu Z, Jiao Y, Wang Y, Zhou C, Zhang Z. Polysaccharides-based nanoparticles as drug delivery systems. *Adv Drug Deliv Rev.* 2008; 60:1650-1662). When chitosan particles are used to deliver a drug, the patient's body is capable of breaking down the chitosan into non-toxic amino sugars. (Mohanraj V J, Chen Y. Nanoparticle—A Review. *Tropical Journal of Pharmaceutical Research.* 2006; 5(1):561-573;

Nicol S. Life after death for empty shells. *New Sci.* 1991; 129:46-48). In addition, chitosan particles can be manipulated to achieve both passive and active drug targeting. (Lee-Sepsick K., Azevedo M. S., Currie D. S., Inventors. Methods and Devices for Conduit Occlusion 2009; Agnihotri S A, Mallikarjuna N N, Aminabhavi T M. Recent Advances on chitosan-based micro- and nanoparticles in drug delivery. *Journal of Controlled Release.* 2004; 100:5-28).

Preparation Methodologies for Chitosan Nanoparticles

Encapsulation methods are chosen in part based on polymer properties, drug hydrophobicity, and desired final particle size. The molecular weight of the chitosan plays a vital role in particle size and formation, as a higher molecular weight produces larger particles. (Tokumitsu H, Ichikawa H, Fukumori Y. Chitosan-Gadopentetic Acid Complex Nanoparticles for Gadolinium Neutron-Capture Therapy Therapy of Cancer: Preparation by Novel Emulsion-Droplet Coalescence Technique and Characterization. *Pharmaceutical Research.* 1999; 16(12):1830-1835; Moghimi S M, Hunter A C, Murray J C. Long-circulating and target specific nanoparticles: theory to practice. *Pharmacol. Rev.* 2001; 53(2):283-318). Another vital component of preparing drug-loaded nanoparticles is the hydrophobicity of the drug. (Wang J J, Zeng Z W, Xiao R Z, et al. Recent advances of chitosan nanoparticles as drug carriers. *International Journal of Nanomedicine.* 2011; 6:765-774). Therefore, the selection of the encapsulation method depends on the desired particle size, drug hydrophobicity, and polymer surface properties to ensure drug encapsulation while minimizing drug loss and maintaining pharmacological activity.

Commonly used methods for preparing chitosan-based drug delivery systems include emulsion cross-linking, emulsion-droplet coalescence, spray drying, sieving, coacervation/precipitation, and ionic gelation. (Muhammed R, Junise V, Saraswathi P, Krishnan P, Dilip C. Development and characterization of chitosan nanoparticles loaded with isoniazid for the treatment of Tuberculosis. *Research Journal of Pharmaceutical, Biological and Chemical Sciences.* 2010: 383-390; Nicol S. Life after death for empty shells. *New Sci.* 1991; 129:46-48; Wang J J, Zeng Z W, Xiao R Z, et al. Recent advances of chitosan nanoparticles as drug carriers. *International Journal of Nanomedicine.* 2011; 6:765-774; Tiyaboonchai W. Chitosan Nanoparticles: A Promising System for Drug Deliver. *Naresuan University Journal.* 2003; 11(3):51-66; Nagpal K, Kumar-Singh S, Nath-Mishr D. Chitosan Nanoparticles: A Promising System in Novel Drug Deliver. *Chem. Pharm. Bull.* 2010; 58(11):1423-1430; Grenha A, Seijo B, Serra C, Remunan-Lopez C. Chitosan Nanoparticle-Loaded Mannitol Microspheres: Structure and Surface Characterization. *Biomacromolecules.* 2007; 8:2072-2079; Shanmuganathan S, Shanumugasundaram N, Adhirajan N, Ramyaa-Lakshmi T S, Babu M. Preparation and characterization of chitosan microsphere for doxycycline delivery. *Carbohydrate Polymers.* 2007:201-211; Pinto-Reis C, Neufeld R J, Ribeiro A J, Veiga F. Nanoencapsulation I. Methods for preparation of drug-loaded polymeric nanoparticles. *Nanomedicine.* 2006:8-21). Methods such as emulsion cross-linking and emulsion-droplet coalescence involve the use of a harsh crosslinking agent that may induce an unnecessary chemical reaction with the active agents. Spray-drying and sieving produce relatively large microparticles, with diameters of approximately 1-10 μm and 543-698 μm, respectively.

Watzke and Dieschbourg conducted some of the earliest work on preparation of nanoparticles by covalent crosslinking (Clavo P, Vila-Jato J, Alonso M J. Evaluation of catonic polymer coated nanocapsules as ocular drug carriers. *Journal of Pharmaceutics.* 1997; 153:41-50). They prepared chitosan/silica nano-composites by simply reacting tetramethoxysilane with the hydroxyl on the chitosan polymer. At that point, nanoparticle delivery systems were not yet used to encapsulate pharmaceutically active agents (i.e., drugs). Ohya et al. were the first to present data using chitosan nanospheres for drug delivery applications. (Pawan P, Mayur M, Ashwin S. Role of Natural Polymers in Sustained Release Drug Delivery System: Application and Recent Approaches. *International Research Journal of Pharmacy.* 2011; 2(9):6-11). They used a water-in-oil emulsion method by crosslinking the amino groups of the chitosan with glutaraldehyde to produce nanospheres loaded with 5-fluorouracil, an anticancer drug. Both of these studies demonstrated the preparation of nano-sized particles that can entrap and deliver drugs. The later discovery of glutaraldehyde's negative impact on cell viability and the integrity of the entrapped drug led to interest in less harsh preparation methods. Ionic gelation is an example of a more benign preparatory method for preparing chitosan nanoparticles.

When chitosan, which is cationic, comes into contact with an anionic compound, it exhibits a unique feature, transitioning from liquid to gel in a process known as ionotropic gelation. The first reported case of using ionic gelation for drug encapsulation using TPP as the crosslinker was that of Bodmeier et al. (Pawan P, Mayur M, Ashwin S. Role of Natural Polymers in Sustained Release Drug Delivery System: Application and Recent Approaches. *International Research Journal of Pharmacy.* 2011; 2(9):6-11; Watzke H J, Dieschbourg C. Novel silica-biopolymer nanocomposites: the silica sol-gel process in biopolymer organogels. *Advances in Colloid and Interface Science.* 1994; 50:1-14). This liquid-to-gel process (i.e., gelation) is due to inter- and intramolecular crosslinkages between tripolyphosphate (TPP) phosphates and chitosan amino groups. Their aim was to produce chitosan-TPP beads; however, the results were nanoparticles.

After the Bodmeier findings, other groups used ionic gelation with TPP as the crosslinker for preparing particles. Shirashi et al. encapsulated indomethacin, an acidic drug, into chitosan gel beads. (Ohya Y, Shiratani M, Kobayashi H, Ouchi T. Release Behavior of 5-Fluorouracil from Chitosan-Gel Nanospheres Immobilizing 5-Fluorouracil Coated with Polysaccharides and Their Cell Specific Cytotoxicity. *Journal of Macromolecular Science.* 1994; 31(5):629-642). Calvo et al. looked at encapsulating protein into chitosan nanoparticles. (Bodmeier R, Chen H, Paeratakul O. A Novel Approach to the Delivery of Microparticles or Nanoparticles *Pharm Res.* 1989; 6:413-417). Gan et al evaluated the potential of chitosan nanoparticles for delivering gene or protein macromolecules. (Shirashi S, Imani T, Ogtagiri M. Controlled release of indomethacin by chitosan-polyelectrolyte complex optimization and in vivo: in vitro evaluation. *J. Control. Release.* 1993; 25(3):217-225). Dung et al examined the potential for encapsulating oligonucleotides. (Clavo P, Remunan-Lopez C, Vila-Jata J L, Alonso M J. Chitosan and Chitosan/Ethylene Oxide-Propylene Oxide Block Copolymer Nanoparticles as Novel Carrier for Protein and Vaccines. *Pharm Res.* 1997; 14(10):1431-1436). Other groups have used ionic gelation to prepare insulin-loaded chitosan nanoparticles. (Gan Q, Wang T, Cochrane C, McCarron P. Modulation of surface charge, particle size and morphological properties of chitosan-TPP nanoparticles intended for gene delivery. *Colloids Surf. B Biointerfaces.* 2005; 44:65-73; Dung T H, Lee S R, Han S D, et al. Chitosan-TPP nanoparticles as a release system of antiense oligonucleotide in the oral environment. *J. Nanosci. Nanotechnol.* 2007; 7(11):3695-3699).

The ionic gelation method has been explored to encapsulate many different biomolecules and drugs, but the linkages between the chitosan and TPP are somewhat weak. To asses this weak linkage, Shu et al explored a novel approach to improving the mechanical strength of chitosan beads. (Fernandez-Urrusuno R, Clavo P, Remunan-Lopez C, Vila-Jato J L, Alonso M J. Enhancement of nasal absorption of insulin using chitosan nanoparticles. *Pharm. Res.* 1999; 16:1576-1581). Xu et al later examined different formulations of chitosan nanoparticles prepared by ionic gelation, assessing the effects of the molecular weight and deacetylation degree of chitosan, the concentration of chitosan, and the initial protein concentration. (Pan Y, Li Y, Zhao H, et al. Chitosan nanoparticles improve the intestinal absorption of insulin in vivo. *Int. J. Pharm.* 2002; 249:139-147).

Ionic gelation is a novel method for preparing chitosan particles, and it offers clear advantages over other methods. Some of those advantages are its simplicity, fast production process, and freedom from a requirement for complicated equipment. In addition, ionic gelation relies not on chemical crosslinking but on reversible physical crosslinking by electrostatic interaction, which reduces the likelihood of the particles' introducing toxins or causing other undesirable effects. The ionic gelation method also offers the flexibility of producing either microparticles or nanoparticles. (Shu X Z, Zhu K J. A novel approach to prepare tripolyphospate/chitosan complex beads for controlled release drug delivery. *Int. J. Pharm.* 2000; 201(1):51-58; Xu Y, Du Y. Effect of molecular structure of chitosan on protein delivery properties of chitosan nanoparticles. *Int. J. Pharm.* 2003; 250(1): 215-226).

Despite the significant advantages of the ionic gelation method and the importance of particle size in determining drug-delivery characteristics, definite formulation parameters for producing particles of a specific size range have yet to be defined. In previous work, researchers looked at only one preparatory variable at a time and did not undertake a systematic look at all the preparatory variables simultaneously. The inventors used doxycycline as the model drug for encapsulation, which is a commonly prescribed, inexpensive, broad-spectrum antibiotic. (Boonsongrit Y, Mitrevej A, Mueller B W. Chitosan drug binding by ionic interaction. *European Journal of Pharmaceutics and Biopharmaceutics.* 2006; 62:267-274).

The inventors have previously demonstrated that encapsulation of doxycycline into chitosan particles can improve drug delivery and the efficacy of the antibiotic while minimizing adverse effects. (Calvo P, Remunan-Lopez C, Vila-Jato J L, Alonso M J. Novel Hydrophilic Chitosanpolyethylene Oxide Nanoparticles as Protein Carriers *J. Appl. Polym. Sci.* 1997; 63(1):125-132). The inventors examined ionic-gelation preparatory variables and their influence on particle size and morphology. Sixty-four different combinations of chemical constituents and procedural steps were used to generate chitosan nanoparticles of wide-ranging morphology and size. A series of multivariate linear models was constructed to determine the optimum (i.e., most influential) variables for determining particle size.

Doxycycline

Doxycycline is an inexpensive, semi-synthetic antibiotic commonly used as a broad-spectrum drug to treat both intracellular and extracellular bacterial infections. Commonly targeted pathogens include both aerobic and anaerobic gram-positive and gram-negative bacteria and also other microorganisms such as protozoa, mycoplasma, mycobacteria, and spirochetes. (Boonsongrit Y, Mitrevej A, Mueller B W. Chitosan drug binding by ionic interaction. *European Journal of Pharmaceutics and Biopharmaceutics.* 2006; 62:267-274; Joshi N, Miller D. Doxycycline Revisited. *Arch Intern Med.* 1997; 157; Cover N, Lai-Yuen S, Parsons A, Kumar A. Synergetic effects of doxycycline-load chitosan nanoparticles for improving drug delivery and efficacy. *International Journal of Nanomedicine.* 2011; Accepted). Due to doxycycline's antibacterial effects on a wide range of pathogens, it is currently one of the most commonly prescribed antibiotics worldwide for treating infectious diseases such as pelvic inflammatory disease (PID), a polymicrobial infection. (Boonsongrit Y, Mitrevej A, Mueller B W. Chitosan drug binding by ionic interaction. *European Journal of Pharmaceutics and Biopharmaceutics.* 2006; 62:267-274; Riond J, Riviere J. Pharmacology and Toxicology of Doxycycline. *Vet Hum Toxicol.* 1988; 30(5):431-443).

For the treatment of diseases such as PID, the CDC recommends 200 mg of doxycycline to be administrated orally or intravenously every 12 hours. (Centers for Disease Control and Prevention. Sexually Transmitted Diseases Treatment Guidelines. *MMWR.* 2010; 59(No. RR-12):1-109). When administered orally or intravenously, however, doxycycline may cause esophageal ulcers, gastrointestinal irritation, and local inflammation, which may in turn lead to premature cessation of treatment. (Cunha B A, Sibley C M, Ristuccia A M. Doxycycline. *Therapeutic Drug Monitoring.* 1982:115-135; Cunha B A, Domenico P, Cunha C B. Pharmacodymanics of doxycycline. *Clinical Microbiology and Infection.* 2001; 6(270-273); Gencosmanoglu R, Kurtkaya-Yapicier O, Tiftikci A, Avsar E, Tozun N, Oran E S. Mid-esophageal ulceration and candidiasis-associated distal esophagitis as two distinct clinical patterns of tetracycline or doxycycline-induced esophageal injury. *J Clin Gastroenterol.* 2004; 38(6):484-489; Morris T J, Davis T P. Doxycycline-induced esophageal ulceration in the U.S. Military service. *Mil Med.* 2000; 165(4):316-319). Furthermore, the use of doxycycline may result in mechanical scarring of tissues and cavities in the body, as well as blood vessels. (Tahan V, Sayrak H, Bayar N, Erer B, Tahan G, Dane F. Doxycycline-induced ulceration mimicking esophageal cancer. *Cases J.* 2008; 1(1):144; Smith K, Leyden J J. Safety of Doxycycline and Minocycline: A Systematic Review. *Clinical Therapeutics.* 2005; 27(9):1329-1342; Heffner J E, Standerfer R J, Torstveit J, Unruh L. Clinical efficacy of Doxycycline for Pleurodesis. *Chest.* 1994; 105(6):1743-1747; Mansson T. Treatment of malignant pleural effusion with doxycycline. *Scand J Infect Dis Suppl.* 1988; 53:29-34; Robinson L A, Fleming W H, Galgraith T A. Intrapleural doxycycline control of malignant pleural effusions. *Ann Thorac Surg.* 1993; 55:1115-1122).

In recent years, drug encapsulation and delivery via small particles has garnered increasing interest. Encapsulation can help prevent adverse effects by protecting sensitive tissues from fast drug exposure while also improving drug efficacy by achieving slow, sustained release directly at the infection site. Having patients complete the entire treatment cycle would also increase the likelihood of complete pathogen elimination. Encapsulation of doxycycline into biodegradable nanoparticles may be used to improve treatment of PID via direct transcervical drug delivery.

The inventors investigated chitosan nanoparticles as a potential carrier of doxycycline. The inventors assessed particle properties relevant to encapsulated drug delivery through a localized (i.e., transuterine) route. Introducing doxycycline-chitosan nanoparticles to the reproductive lumen produces sustained drug levels in the reproductive tract by adhesion of the particles to the mucosa as well as absorption of the particles into the tissue, thus increasing the likelihood of complete pathogen elimination. The inventors created and then characterized doxycycline-loaded chitosan nanoparticles (DCNPs) in terms of their morphology (size and shape), drug encapsulation efficiency and release rates, in vitro antibacterial activity, and in vitro cytotoxicity.

The inventors have also developed a novel sterile uterine sampler cover (SUSC) device to collect sterile cell samples from the fallopian tubes, uterus and surrounding areas. This device improves the accuracy of diagnosis of pelvic inflammatory disease (PID). The device is designed to collect sterile samples from the uterus that can then be analyzed to identify the specific pathogens causing PID as well as other uterine infections. The device can also be used to deliver nanoencapsulated drugs at the site of infection for targeted drug delivery.

SUMMARY OF INVENTION

Pelvic Inflammatory Disease (PID) is one of the most common causes of morbidity in women. PID is a polymicrobial infection of the female reproductive tract, and is associated with pelvic pain, abnormal uterine bleeding, and tubal damage that can lead to ectopic pregnancies and infertility. It is curable but the effects of PID can be permanent if not properly diagnosed and treated. PID presents as a spectrum of disease and is often missed at early stages; even acute PID can be difficult to diagnose, as there is no single conclusive diagnostic test. Currently, PID is identified and treated syndromically because pelvic pain is the only consistent clinical finding. The Center for Disease Control and Prevention (CDC) recommends doxycycline, a broad-spectrum antibiotic, for treatment but doxycycline can cause gastrointestinal irritation and local inflammation leading to an incomplete treatment.

Most cases of PID are polymicrobial infections of the tubes and endometrium, which are not accessible to culture due to the difficulty of procuring samples above the naturally contaminated vagina and distal cervix. Given the difficulty of properly diagnosing PID and the limitations and side effects of the current treatments, there is an urgent need for new approaches for improving the accuracy for diagnosis and treatment of PID.

The inventors have developed a new and practical approach to collect sterile specimen samples from the endometrium for more accurate PID diagnosis, and to treat the reproductive tract locally using doxycycline-loaded nanoparticles. A novel sterile uterine sampler cover (SUSC) device is presented herein that safely and effectively collects uncontaminated specimen samples from the uterus, and also delivers nano-encapsulated drugs directly to the site of infection.

The sterile uterine sampler cover (SUSC) device can be used to collect uncontaminated samples from the uterus. The SUSC device may be comprised of 2 main components assembled as one unit. The first component is a cannula having a first and a second end. The cannula may be between about 100 mm to about 300 mm in length and have an outer diameter of between about 2 mm to about 10 mm. In an embodiment, the cannula has dimensions of about 200 mm in length and an about 5 mm diameter. The cannula may be slightly tapered at the first end and have at least one locking flange at the second end. In some embodiments, there are two locking flanges at the second end. In addition, the first end of the cannula may contain an orifice having a diameter of between about 2 mm to about 10 mm.

The second component is a cover having a first and second end. The first end of the cover may be closed while the second end is open. The open end may have hard plastic ring containing a locking mechanism (lock). The lock may be adapted with at least one slot that is capable of engaging with the at least one flange located at the second end of the cannula. When engaged, the lock secures the cover in place encasing the cannula.

The cover may be manufactured from an elastomeric material, such as silicone. In addition, the cover should be sterile and lubricated before use. The cover is proportional in length to the cannula and may be between about 100 mm to about 300 mm in length.

The device may also have a sampler in the shape of a sterile tube having a first and a second end. The first end of the sampler may have an orifice through which a sample may be collected or a drug may be administered. The sampler is disposed within the lumen of the cannula. A plunger may be disposed within the lumen of the sampler.

In use, the cover fits over the cannula at the tapered end and is stretched to lock the ring at the other end. The operator uses sterile gloves and a speculum to expose the uterine cervix which is cleansed at the external os with sterile solution on a swab until all visible mucus and debris are removed. The sterile cover is packaged with the cannula inserted. When the ring is pulled the cover is stretched taunt over the cannula and is locked by twisting to catch the flanges. Sterile lubricant is applied to the cover at its tip and the device is gently inserted into the cervix to the point of resistance at the internal os (at least 2.5 cm deep). The outer cannula will not go further than the internal os and this location will be clearly felt by the user.

Once the outer cannula is positioned at the internal os, a standard endometrial sampler device is inserted into the cannula thus breaking the cover which snaps back to the ring outside of the vagina. This admits the sampler into the uterine cavity without allowing it to contact any vaginal or cervical surfaces. The endometrial sample is collected as usual and the sampler is carefully removed from the cannula which is still uncontaminated. The sample is deposited into sterile media for bacteriology examination and the device is removed from the cervix and disposed of in a contamination waste container.

The analysis of uncontaminated endometrium samples provides an understanding of uterine flora in symptomatic and asymptomatic women that leads to the identification of infective microbes in symptomatic women for pathogen-specific treatment.

The use of nano-encapsulated doxycycline enables localized drug delivery to lower drug dosage and minimize side effects for the patient. The doxycycline-loaded nanoparticles are characterized and evaluated based on their drug release properties, size distribution, and tissue response in vitro. The inventors have developed a more effective approach for the diagnosis and treatment of PID while freeing women from prolonged systemic treatments and their adverse effects while increasing our understanding of the uterine biome under various hormonal and pathologic conditions, in symptomatic and asymptomatic women.

BRIEF DESCRIPTION OF THE DRAWINGS

For a fuller understanding of the invention, reference should be made to the following detailed description, taken in connection with the accompanying drawings, in which:

FIGS. 7A-C is a series of images depicting three different phases of the device. (a) Assembling of the SUSC device (b) the sterile cover stretched and locked in position on the outer cannula and (c) the cover in its retracted position after piercing with the sampler.

FIGS. 14A-D are a series of TEM images of blank (drug-free) chitosan particles prepared in (a) nanopure water, (b) 0.25M acetic acid solution, (c) 0.50M acetic acid solution, and (d) 0.75M acetic acid solution.

FIGS. 15A-B are a series of graphs depicting the particle size distributions of samples of drug-loaded particles (a) passively precipitated and (b) centrifuged, washed and resuspended in water.

FIGS. 16A-B is a series of TEM images of doxycycline-loaded nanoparticles that were washed, centrifuged, and then resuspended in nanopure water. (a) Several individual particles clumping together, 80k× magnification; (b) an agglomeration of smaller particles, 400k× magnification.

FIGS. 17A-B is a series of TEM images of doxycycline-loaded nanoparticles that were washed, centrifuged, and then resuspended in PBS. Particle diameters range from approximately 160 to 400 nm: (a) 6k× magnification; (b) 60k× magnification.

FIG. 18A-D is a series of images depicting particle size distribution and TEM images for DCNP4 (top) and DCNP6 (bottom).

FIG. 21A-B is a series of graphs depicting five-day cell viability for human ovarian surface epithelial cells exposed to blank nanoparticles, drug-loaded nanoparticles, and unencapsulated doxycycline. A higher formazan absorbance indicates greater cell viability. Data shown are the mean±standard deviation (n=3).

FIGS. 22A-C is a series of bright field images of human ovarian surface epithelial cells after being exposed to the different treatments. (a) No treatment (control), (b) doxycycline at 2 µg/mL, and (c) DCNP4 at 2 µg/mL. Magnification 10×.

FIG. 23 is a list of the 64 formulations of chitosan nanoparticles. Each formulation was done in triple and then all three trials were averaged. The average particle size is represented in the last column.

FIG. 24 is a table depicting AIC-Based Stepwise Selection Conditional Tests.

FIG. 25 is a table depicting AIC-Based Stepwise Selection Marginal Tests.

FIG. 26 is a table depicting Stepwise Redundancy Analysis Global Test.

FIG. 27 is a table depicting Stepwise Redundancy Analysis Conditional Tests.

FIG. 28 is a table depicting Stepwise Redundancy Analysis Marginal Tests.

FIG. 29 is a series of tables depicting Multiple Linear Regression via QR Factorization.

FIG. 32 is a table depicting Day 1 WST-1 Raw Data for Formulation 1.

FIG. 33 is a table depicting Day 3 WST-1 Raw Data for Formulation 1.

FIG. 34 is a table depicting Day 5 WST-1 Raw Data for Formulation 1.

FIG. 35 is a table depicting Day 1 WST-1 Raw Data for Formulation 2.

FIG. 36 is a table depicting Day 3 WST-1 Raw Data for Formulation 2.

FIG. 37 is a table depicting Day 5 WST-1 Raw Data for Formulation 2.

DETAILED DESCRIPTION OF THE PREFERRED EMBODIMENT

Figure 1:
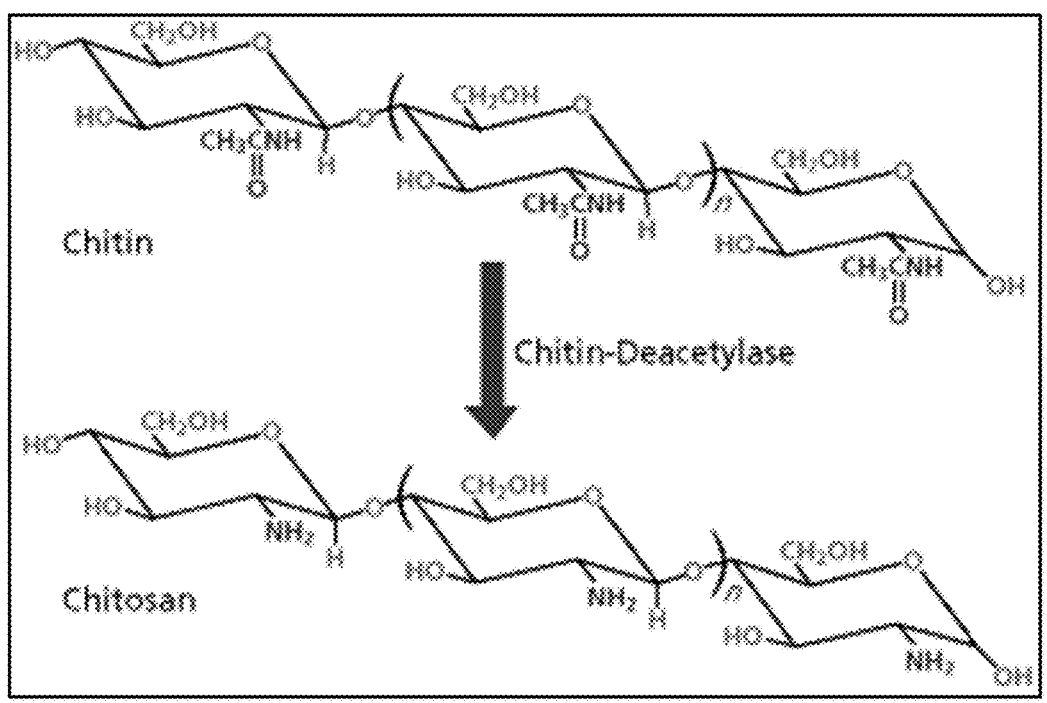
FIG. 1 is an image depicting the chemical structure of chitin and chitosan.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

As used in the specification and claims, the singular form "a", "an" and "the" include plural references unless the context clearly dictates otherwise. For example, the term "a nanoparticle" includes a plurality of nanoparticles, including mixtures thereof.

The terms "external orifice" or "external os" as used herein refers to the opening of the cervix which is located adjacent the vagina.

The terms "internal orifice" or "internal os" as used herein refers to the opening of the cervix which is located adjacent to the uterus. The endocervial canal connects the external os to the internal os.

The term "elastomeric" as used herein refers to a material made of polymers having viscoelasticity. These polymers generally have a low Young's modulus and a high failure strain as compared to other materials. Elastomeric polymers are capable of being stretched to great extents by a deforming force and resuming their natural shape once the deforming force is removed. One of ordinary skill in the art would readily recognize elastomeric polymers and all such polymers are contemplated for use in the invention contained herein. Examples of elastomeric polymers include, but are not limited to, natural and synthetic rubbers, silicone, latex, etc.

According to the Centers for Disease Control and Prevention (CDC), an estimated 1.0 million women in the United States experience acute pelvic inflammatory disease (PID), and 1-2 billion dollars are spent for PID and its sequelae treatment each year. (Crossman S. The Challenge of Pelvic Inflammatory Disease. *American Family Physician.* 2006; 73(5):859-864; Haggerty C, Ness R. Newest Approaches to Treatment of Pelvic Inflammatory Disease: A Review of Recent Randomized Clinical Trials. *Clinical Infectious Diseases.* 2007; 44:953-960; Walker C, Wiesenfeld H. Antibiotic Therapy for Acute Pelvic Inflammatory Disease: The 2006 Centers for Disease Control and Prevention Sexually Transmitted Diseases Treatment Guidelines. *Clinical Infectious Diseases.* 2007; 44(S111-22); Sweet R. Role of Bacterial Vaginosis in Pelvic Inflammatory Disease. *Clinical Infectious Diseases.* 1995; 20(2):271-275; Peterson H B, Galaid E I, Zenilman J M. Pelvic Inflammatory Disease: Review of Treatment Options. *Reviews of Infectious Diseases.* 1990; 12(6):656-664; Rein D B, Kassler W J, Irwin K L, Rabiee L. Direct Cost of Pelvic Inflammatory Disease and Its Sequelae: Decreasing but Still Substantial *Obstetrics and Gynecology.* 2000; 95(3):397-402). PID is an infection of the upper genital tract, which includes the uterus (endometrium), fallopian tubes, and surrounding organs. It is hypothesized that microorganisms such as *Chlamydia trachomatis, Neisseria gonorrhoeae*, and microorganisms of the vagina's normal flora cause PID. (Bell J D, Bergin I L, Schmidt K, Zochowski M K, Aronoff D M, Patton D L. Nonhuman Primate Models Used to Study Pelvic Inflammatory Disease Caused by *Chlamydia trachomatis*. *Infect Dis Obstet Gynecol.* 2011:1-7; Soper D E. Pelvic inflammatory disease. *Obstet Gynecol.* 2010; 116(2):419-428; Centers for Disease Control and Prevention (CDC). Cephalosporin susceptibility among *Neisseria gonorrhoeae* isolates—United States, 2000-2010. *MMWR Morb Mortal Wkly Rep.* 2011; 60(26):873-877). Symptoms associated with PID include pelvic pain, abnormal uterine bleeding, and vaginal discharge. The reproductive infection can also result in tubal damage, which can lead to ectopic pregnancies and infertility. (Crossman S. The Challenge of Pelvic Inflammatory Disease. *American Family Physician.* 2006; 73(5):859-864; Sweet R. Role of Bacterial Vaginosis in Pelvic Inflammatory Disease. *Clinical Infectious Diseases.* 1995; 20(2):271-275; Soper D E. Pelvic inflammatory disease. *Obstet Gynecol.* 2010; 116(2):419-428; Beigi R, Wiesenfeld H. Pelvic Inflammatory disease: new diagnostic criteria and treatment. *Obstetrics and Gynecology Clinics of North America.* 2003; 30:777-793; Hay P E, Pittrof R. Has the effectiveness of a single chlamydia test in preventing pelvic inflammatory disease over 12 months been overestimated? *Women's Health*. 2010; 6(5):627-630). Unrecognized (dormant) infection is thought to be associated with preterm labor, and neonatal mortality. Approximately 33% of severe PID cases are reportedly incorrectly diagnosed,—a lack of reliable and conclusive diagnostic testing can make detection of acute PID very difficult. In its early stages, PID often goes undiagnosed as symptoms can be subtle. (Walker C, Wiesenfeld H. Antibiotic Therapy for Acute Pelvic Inflammatory Disease: The 2006 Centers for Disease Control and Prevention Sexually Transmitted Diseases Treatment Guidelines. *Clinical Infectious Diseases.* 2007; 44(S111-22); Dayan L. Pelvic Inflammatory Disease. *American Family Physician.* 2006; 36(11):858-862; Jaiyeoba O, Soper D E. A Practical Approach to the Diagnosis of Pelvic Inflammatory Diseas. *Infect Dis Obstet Gynecol.* 2011:1-6; Wiesenfeld H C, Hillier S L, Krohn M A, et al. Lower Genital Tract Infection and Endometritis: Insight Into Subclinical Pelvic Inflammatory Disease. *The American College of Obstetricians and Gynecologists.* 2002; 100(3): 456-463).

Current PID diagnosis is based on CDC recommended minimal diagnostic criteria: pelvic pain as cervical motion tenderness, uterine tenderness and/or adnexal tenderness. Evidence of lower genital tract inflammation—leukocytes in vaginal secretions, cervical exudates or bleeding on contact—increases the likelihood of PID as a cause for pelvic pain. Other supportive but not necessary findings include: temperature above 38.3° C., an elevated erythrocyte sedimentation rate, elevated serum levels of C-reactive protein, prior or current *N. gonorrhoeae* or *C. trachomatis* infections, or an inflamed mass on pelvic sonography. (Beigi R, Wiesenfeld H. Pelvic Inflammatory disease: new diagnostic criteria and treatment. *Obstetrics and Gynecology Clinics of North America.* 2003; 30:777-793; Jaiyeoba O, Soper D E. A Practical Approach to the Diagnosis of Pelvic Inflammatory Diseas. *Infect Dis Obstet Gynecol.* 2011:1-6). Along with the CDC criteria, medical history especially risk factors, physical examination, and a few laboratory tests, including C reactive protein, peripheral white cell count, and erythrocyte sedimentation rate, and cervical testing for *C. trachomatis* and *N. gonorrhea* constitute the usual methods for diagnosing PID. The sensitivity and specificity of these laboratory test approaches ranges from for poor to fair when it comes to diagnosing PID. (Soper D E. Pelvic inflammatory disease. *Obstet Gynecol.* 2010; 116(2):419-428; Beigi R, Wiesenfeld H. Pelvic Inflammatory disease: new diagnostic criteria and treatment. *Obstetrics and Gynecology Clinics of North America.* 2003; 30:777-793). It has long been observed that women with no history of recognized PID often present with tubal factor infertility. (Moore D E, Spadoni L R, Foy H M. Increased frequency of serum antibodies to *Chlamydia trachomatis* in infertility due to distal tubal disease. *Comparative Study* 1982; 2(8298):547-547; Punnonen R, Terho P N V, Meurman O. Chlamydial serology in infertile woman by immunofluorescence. *Fertil Steril.* 1979; 31(6):656-659; Wolner-Hanssen P. Silent pelvic inflammatory disease: is it overstated? *Obstet Gynecol.* 1995; 86(3):321-325)). Persistent chlamydia in the upper reproductive tract was identified in 15% of 52 women undergoing tubal surgery for infertility. (Shepard M K, Jones R B. Recovery of *Chlamydia trachomatis* from endometrial and fallopian tube biopsies in women with infertility of tubal origin. *Fertil Steril.* 1989; 52(2):232). *Chlamydia* was found in the peritoneal fluid in 44% of women laparoscoped for pelvic pain with signs of salpingitis, and in 37% of women undergoing surgery for tubal sterility. (Keilani A, Boulieu D, Raudrant D, Carraz M, Quenin P. Role of *Chlamydia trachomatis* in tubal pathology (acute salpingitis and tubal sterility). Microbiological study of 175 samples of peritoneal fluid. *J Gynecol Obstet Biol Reprod (Paris).* 1989; 18(2):167-172). Recent data have broadened recognition of subclinical PID (15) as identified by the presence of leukocytes and plasma cells in an endometrial biopsy. (Wiesenfeld H C, Hillier S L, Krohn M A, et al. Lower Genital Tract Infection and Endometritis: Insight Into Subclinical Pelvic Inflammatory Disease. *The American College of Obstetricians and Gynecologists.* 2002; 100(3):456-463). However, use of endometrial tissue for microbial identification has not been adequately tested using modern genetic identification techniques. Neither have the normal flora of the healthy uterine cavity been characterized.

Ultrasound is useful for detecting overt inflammatory changes in pelvic organs, but has poor sensitivity when these are minimal. (Crossman S. The Challenge of Pelvic Inflammatory Disease. *American Family Physician.* 2006; 73(5): 859-864; Beigi R, Wiesenfeld H. Pelvic Inflammatory disease: new diagnostic criteria and treatment. *Obstetrics and Gynecology Clinics of North America.* 2003; 30:777-793; Ross J D. An Update on Pelvic Inflammatory Disease. *Sex Transm Inf* 2002; 78:18-19). The current gold standard for diagnosing PID is laparoscopy, a minimally invasive surgery, to provide physical evidence and allow upper tract sampling. However, this is a resource intensive procedure requiring general anesthesia with significant risk. (Beigi R, Wiesenfeld H. Pelvic Inflammatory disease: new diagnostic criteria and treatment. *Obstetrics and Gynecology Clinics of North America.* 2003; 30:777-793; Peipert J, Boardman L, Hogan J, Sung J, Mayer K. Labortory Evaluation of Acute Upper Genital Tract Infection. *Obstetrics and Gynecology* 1996; 87:730-736; Henry-Suchet J. PID: Clinical and Laparoscopic Aspects. *Ann N Y Acad Sci.* 2000; 900:301-308) Empirical antibiotic therapy that covers both *Chlamydia trachomatis* and *Neisseria gonorrhoeae* is the first line of treatment. The patient is then monitored to determine if or when symptoms subside, while awaiting test results for cervical evidence of *chlamydia* or gonorrhea.

The CDC recommends doxycycline, an inexpensive, widely available broad-spectrum antibiotic, which obtains very high drug levels in the pelvic area, as a key component of treatment. However, this drug can cause gastrointestinal irritation when taken orally, and requires a two-week treatment course. Doxycycline may also cause local inflammation when given intravenously. These side effects often result in incomplete treatment. Current gynecological devices for collecting endometrium cannot provide sterile samples, hence the reliance on evidence of inflammation in endometrial biopsies as sole evidence of 'subclinical' upper tract infection in women with minimal pain.

Analysis of uncontaminated endometrial tissue is expected to provide an accurate diagnosis of local inflammation and identify the specific organisms causing it, guiding the selection of the best treatment. As is currently done with urinary tract infections, drugs can be started using current assumptions, and corrected as needed after data is available. Equally importantly, uncontaminated endometrial sampling will allow a better understanding of the natural microbial ecology of the uterus under a variety of spontaneous and manipulated hormonal conditions. It is highly likely that biofilms of sessile pathogens exist in the endometrial cavity as they do in the inner ear, bladder, and prostate, and this has enormous implications for fertility and complications of pregnancy.

Sterile Uterine Sampler Cover (SUSC) Device

The lack of accurate diagnostic methods and/or devices has severely limited understanding of PID, particularly those episodes of inflammation which are associated with bowel commensals rather than chlamydia and gonorrhea, or produce recurrent symptoms, or occur in apparently low risk women. The inventors hope to avoid delayed treatment in atypical cases, and overtreatment when there is no infection. Once pathogens are identified, the inventors believe that local treatment may be more effective than systemic treatment, as is done in dairy cows. (Goshen T, Shpigel N Y. Evaluation of intrauterine antibiotic treatment of clinical metritis and retained fetal membranes in dairy cows. *Theriogenology*. 2006; 66(9):2210-2218). Development of a new topical treatment approach requires reformulation of currently used drugs for minimal toxicity and effective application—ideally transvaginally by the patient herself.

As described previously, endometrial sampling devices and/or techniques are currently available but none of these devices and/or techniques can procure sterile specimen samples from the endometrium and surrounding areas. Procuring sterile specimen samples is expected to provide an accurate diagnostic of PID and to increase understanding of the normal flora in asymptomatic women.

The inventors have developed an SUSC device to enable the collection of uncontaminated endometrium samples through the vagina to increase understanding of the natural microbial ecology of the uterus. The collected samples can be later analyzed to identify the specific pathogens causing PID and to determine adequate treatment methods. The SUSC device has several other uses for addressing other gynecological disorders/problems including, but not limited to, removal of obstructions in the fallopian tubes; targeting sperm delivery; delivering MEMs technology containing diagnostic agents for sensitive imaging of neoplastic cells in the fallopian tubes; and monitoring the normal flora of the fallopian tubes and the uterus.

A thorough literature review was conducted in combination with a clinician survey to gather user requirements for a device to collect sterile samples from the uterus. The survey consisted of five short questions that focused on identifying the needs and their importance to determine the specifications of the device. These end-user requirements included: ease of handling; comfortable (to the patient); prevents sample contamination; device durability; and dimensions of the device. The device is preferably easy to handle; causes little to no pain during the sampling process; prevents vaginal and cervical contamination from entering the uterus; is manufactured to be stiff enough that it does not bend easily but soft enough that the patient is not harmed during use; and has dimensions such that it may be used in different sizes of cervices. The importance of each end-user requirement was ranked based on the information gathered from the survey.

The SUSC device is designed to enter through the distal end of the vaginal canal and enter the uterus through the narrow cervical opening. Therefore, the inventors analyzed the female reproductive system to collect the dimensions and constraints for device specifications. These dimensions vary from woman to woman depending on age and hormonal state, thus the device must accommodate the range of female measurements.

Figure 2:
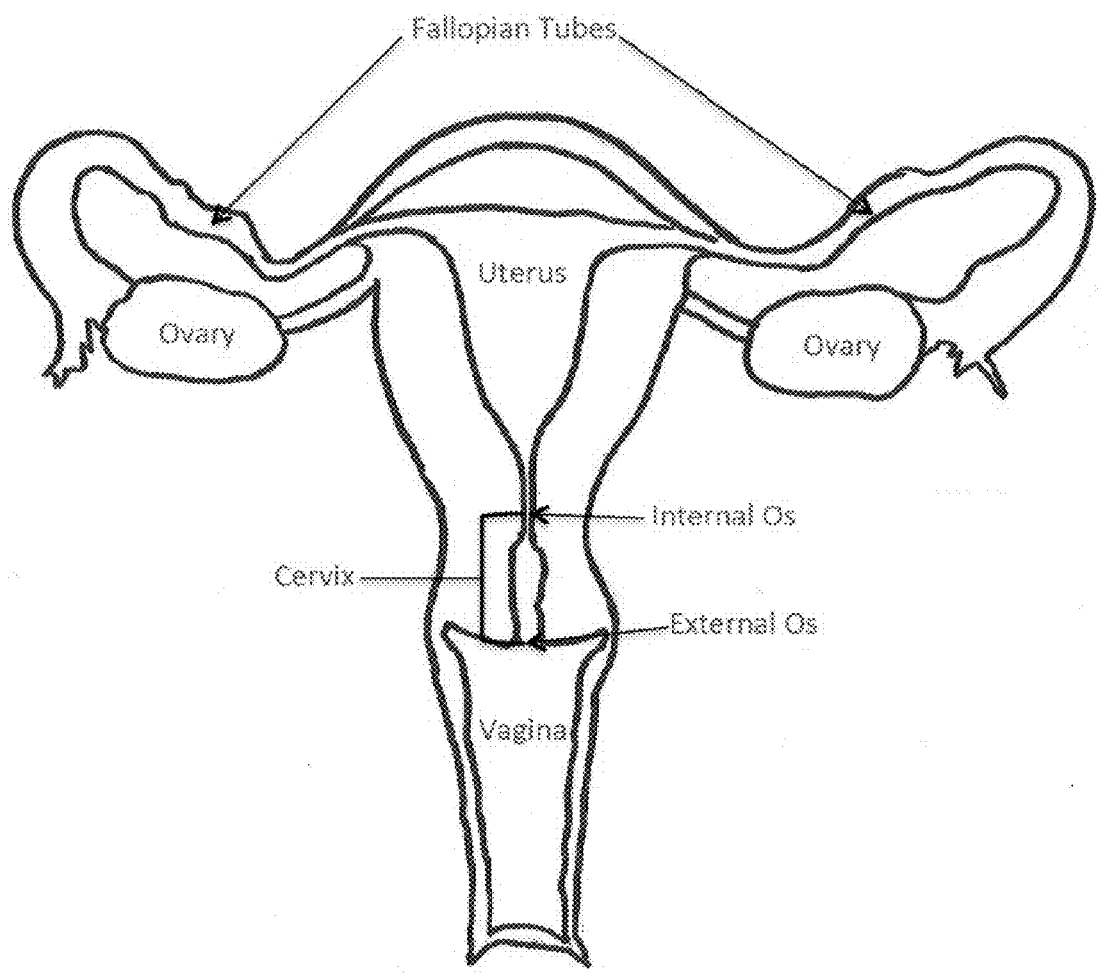
FIG. 2 is an image depicting a schematic representation of the female reproductive system.

The vagina, where the device enters the body, is connected to the cervix of the uterus (womb). Extending from either side of the uterus are the fallopian tubes, and at the ends of the fallopian tubes are the ovaries, two small almond-shaped organs (FIG. 2). The fallopian tubes are two thin tubes about 80 to 120 mm in length on either side of the uterus that serve as the pathway during ovulation for the egg leaving the ovary to reach the uterus for fertilization. The human vagina is a long, collapsible fibromuscular tubal organ with a length of about 60 to 120 mm measured posteriorly. This length varies depending on the age of the female as well as her state of sexual arousal.

At the top end of the vaginal tube is the cylindrically shaped cervix, and at the center of the cervix is an opening known as the external orifice (commonly referred to the as "external os"). The portion of the cervix projecting into the vagina is known as the ectocervix and is approximately 30 mm long and 25 mm wide; the dimensions vary depending on age and hormonal state. The spindle-shaped endocervical canal, in the cavity of the cervix, is the passageway between the external os and the uterine cavity; it also varies in width and length. Women of reproductive age have the widest endocervical canals (about 7-8 mm). The endocervical canal terminates at the internal orifice ("internal os") to the uterine cavity.

Figure 3:
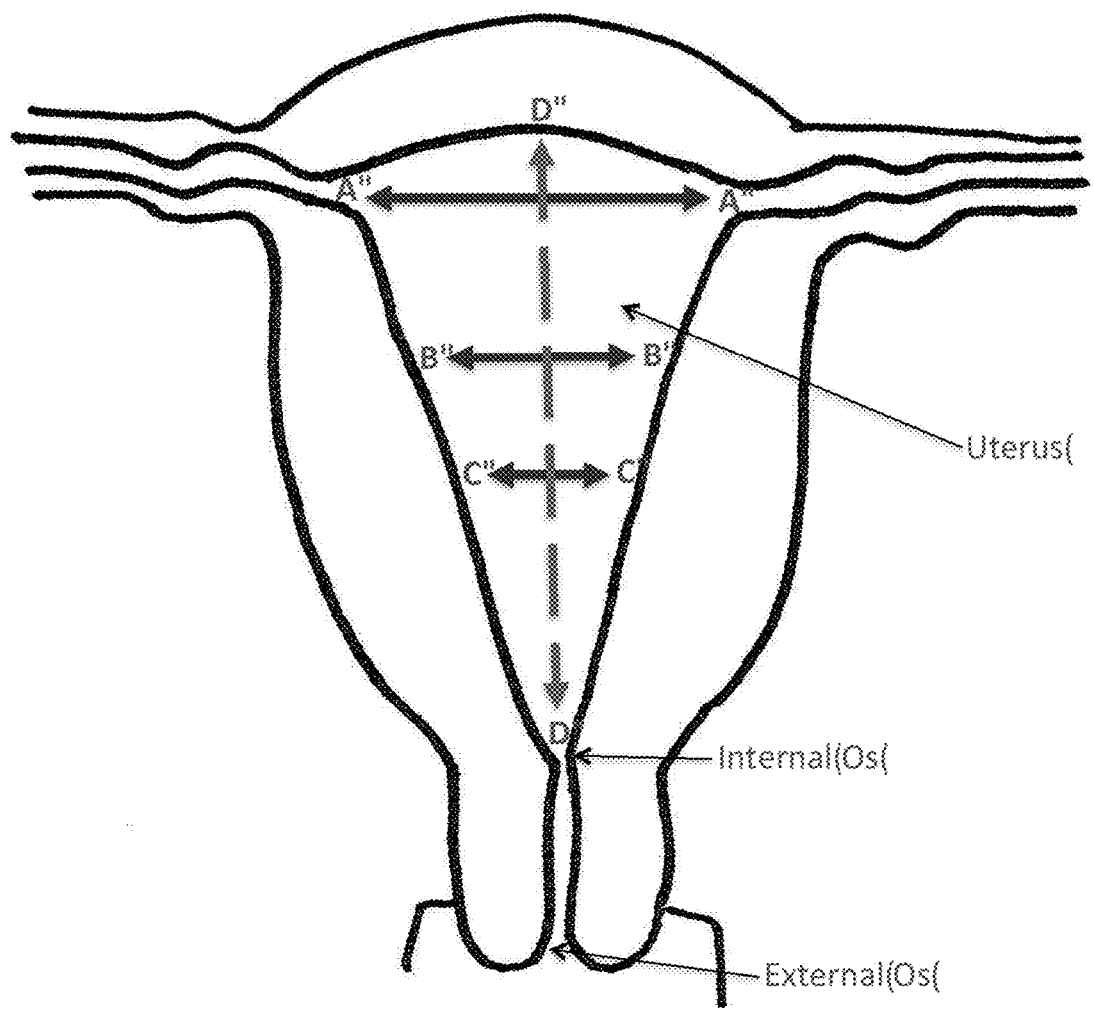
FIG. 3 is an image depicting a transverse view and dimensions of the endometrium (uterus).

If the uterus is cut transversely (FIG. 3) from the entrance of the left fallopian tube to the right one (A-A') it measures from about 26 to about 34.6 mm. From the top of the uterine cavity to the internal os (D-D') is about 33.2 to about 43.8 mm. Going down one-third from the superior portion of the uterine cavity (B-B') is about 17.3 to about 27.5 mm and then going down another one-third (C-C') it is about 10 to about 18.6 mm.

Figure 4:
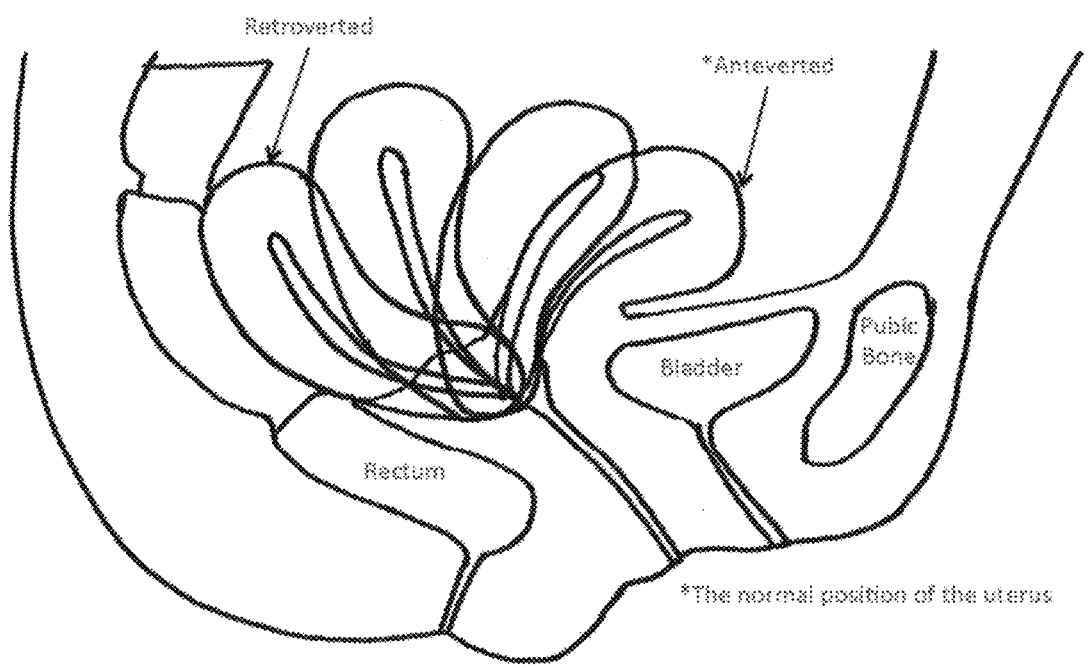
FIG. 4 is an image depicting the different positions of the uterus.

In addition to the above listed dimensional constraints, the positioning of the uterus imposes another constraint. The uterus is normally found in the anteverted position so it is tipped forwards. In a few cases, it is retroverted in the position so it is tipped backwards. The different possible positions of the uterus are illustrated in FIG. 4.

Figure 5:
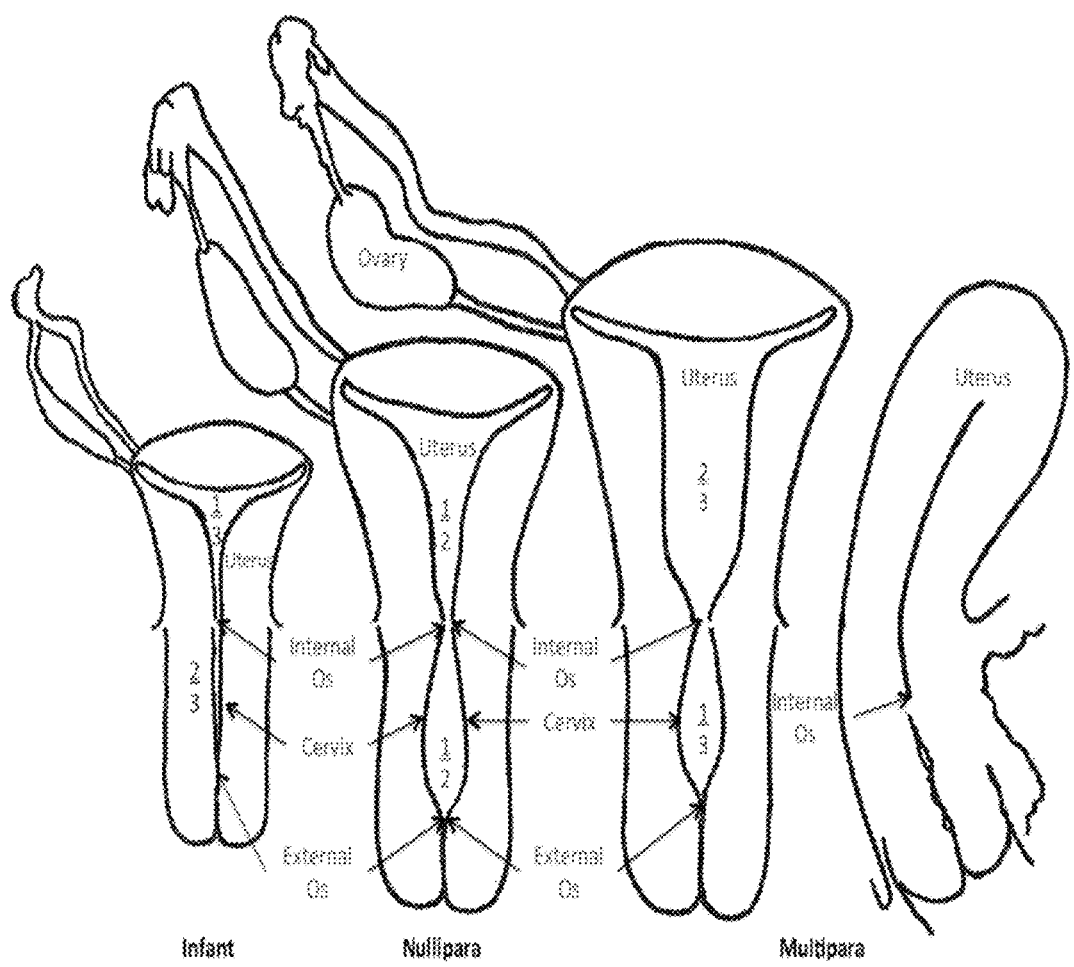
FIG. 5 is an image depicting the sizes of the uterus in different women at different hormonal stages.

The SUSC device was designed to enter through the vagina, which varies in length from about 60 to about 120 mm. At the distal end of the vaginal canal, the SUSC device enters the uterus through an about 2-3 mm cervical opening. These dimensions vary from woman to woman depending on age and hormonal state. Therefore, the device must accommodate the range of female measurements. FIG. 5 illustrates the different sizes of the uteruses in different woman at different hormonal stages.

One function of the device is to collect sterile specimen samples from the uterus while preventing vaginal and cervical contamination. Another function is to deliver nanoencapsulated drugs directly to the uterus. Various design concepts were developed and the top three concepts were evaluated in detail and weighted values were assigned to each end-user requirement and/or function (Table 1). The weighted percentage was determined by a survey administered to a group of physicians.

TABLE 1

| Selection Criteria/ (Weight) | A-Straight One-Sided Sampler | | B- Rounded Two-Sided Sampler | | C- One-Sided Sampler with Cover | |
|---|---|---|---|---|---|---|
| | Rating | Weighted Score | Rating | Weighted Score | Rating | Weighted Score |
| Prevent Contamination (40%) | 1 | 0.08 | 2 | 0.16 | 5 | 0.4 |
| Patient Comfort (26%) | 3 | 0.156 | 2 | 0.104 | 4 | 0.208 |
| Ease of Handling (18%) | 4 | 0.144 | 2 | 0.072 | 4 | 0.144 |
| Device Durability (10%) | 3 | 0.06 | 4 | 0.08 | 3 | 0.06 |
| Dimension of Device (6%) | 4 | 0.048 | 1 | 0.012 | 4 | 0.048 |
| Total Score | | 0.488 | | 0.428 | | 0.86 |
| Rank | | 2 | | 3 | | 1 |
| Continue? | | No | | No | | Yes |

For the straight single cannula sampler (concept A in Table 1), the entire design was a single and straight sampler with an exit hole in the tip of the cannula. The major drawback of this concept was the lack of proper prevention of vaginal and cervical contamination during sampling. In addition, the straightness of this design concept posed another problem. Because the uterus is normally positioned anteverted, insertion of a straight device would have a strong possibility of causing tissue damage. Furthermore, having the exit hole at the tip of the sampler may result in blockage by tissue thus obstructing the sample collection.

The concept of a rounded two-sided sampler (concept B in Table 1) was also explored. In this design concept, there were two tubes in one barrel. The barrel has two exit holes that are in opposite direction to allow the inner tubes to emerge for sample collection. The two inner tubes provide dual functionality: suctioning uterine tissue specimens and delivering therapeutic drugs directly to the uterus. The tip of the barrel is rounded to diminish the likelihood of potential tissue damage during insertion. Putting the holes on the side of the device addressed the problem with tissue blockage (as in concept A) upon insertion. Because of the complexity of the internal design, the outer diameter of the barrel would be larger than the single cannula design (concept A). Therefore, this design has a greater potential for causing patient discomfort. In addition, the device does not completely address the prevention of contamination during uterine specimen sampling.

The concept of an outer cannula with a protective cover (concept C in Table 1) was also explored. This approach addresses the major problem of contamination, which the other two concepts did not address satisfactorily. The protective cover serves as an outer covering to help prevent the spread of contamination from the vagina and uterus. The outer cannula would provide additional protection from contamination. This design concept has about a 20° angle at the distal end of both cannulas, designed to allow the device to follow the normal curvature of the uterus. This overall concept allows for easier insertion and higher prevention of cross contamination.

After evaluation of the designs, concept C was selected for development. Based on the dimensional constraints of the female reproductive system and the proposed function of the device, the device should consist of three components: a sterile cover, an outer cannula, and a sampler. These three components were selected for the final design placing a high priority in preventing contamination while minimizing the outer diameter of the device to reduce any form of pain during insertion. When all three components are assembled, the device's maximum length and diameter should be at least 420 mm and at most 5 mm, respectively. This length ensures its ease of use and maximum distance from the patient's vaginal area to the external working area. An outer diameter of about 5 mm or smaller is desired to ensure little to no patient pain, though slightly larger devices may be used. The diameter of the sampler is optimally about 2.5 mm, though smaller samplers may be used. Table 2 summarizes example engineering specifications based on the dimensional constraints imposed by the female anatomy.

TABLE 2

Engineering specifications for each component of the SUSC device

| Part(s) | Function | Dimensions |
|---|---|---|
| Outer Cannula | Housing for the sampler | Length = 100-300 mm, 200 mm optimal<br>Outer diameter = 2-10 mm, 5 mm optimal<br>Diameter of hole = 2-10 mm, 3 mm optimal |
| Sampler | Collect tissue sample and/or to deliver drugs | Length = 100-300 mm, 240 mm optimal<br>Diameter = 2-10 mm, 2.5 mm optimal |
| Sterile Cover | Protective covering of the device | Length = 100-300 mm, 180 mm optimal |

Figure 6A:
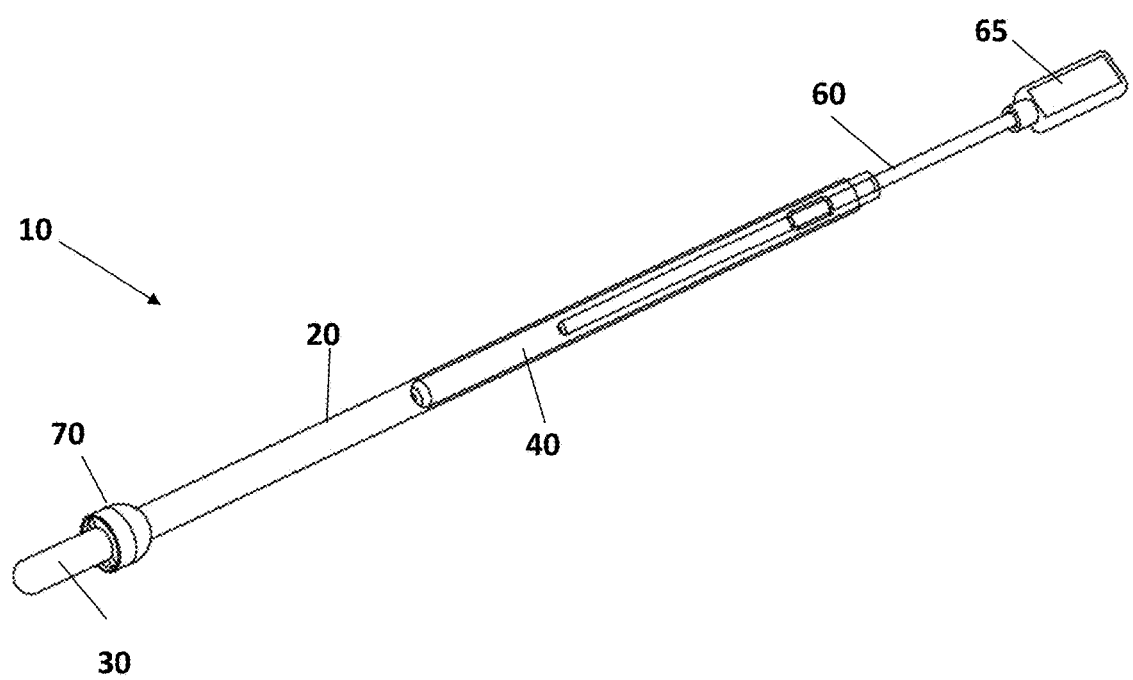
FIGS. 6A-C is a series of images of the SUSC device.

One embodiment of the device is depicted in FIG. 6A. As depicted in FIG. 6A, device 10 may include cannula 20, cover 30 and sampler 40. Outer cannula 20 has is an elongated tube and consists of first end 22 and second end 24. Cannula 20 may have a length of about 200 mm with a diameter of about 5 mm. Cannula 20 may be slightly tapered at first end 22. Second end 24 may have at least one locking flange 72.

Cover 30 is preferably manufactured of an elastomeric material such as silicone and is also preferably lubricated prior to use. Cover 30 may have a diameter of about 6 mm and a length of about 100 mm. Cover 30 is positioned over first end 22 of outer cannula 20. Cover 30 may have a first end which is closed and a second end which is open. Cover 30 may have a hard plastic ring containing lock 70 positioned at its second end to lock cover 30 in place over cannula 20 when cover 30 is stretched over cannula 20. Sampler 40 has a diameter that is smaller than the diameter of outer cannula so that sampler 40 may be inserted into second end 24 of outer cannula 20 when in use. Sampler 40 is an elongated tube having first and second ends with plunger 60 being positioned within second end of sampler 40. Plunger 60 also is elongated with first and second ends with a widened portion constituting hand grip 65 located at second end. Hand grip 65 of plunger 60 has a diameter larger than the diameter of outer cannula 20 so that when sampler 40 is inserted into outer cannula 20 and plunger 60 is moved to advance sampler 40 through outer cannula 20, plunger 60 is stopped at second end of outer cannula 20.

In use, cover 30 fits over cannula 20 at tapered first end 22 and is stretched to secure lock 70 at second end 24. The operator uses sterile gloves and a speculum to expose the uterine cervix which is cleansed at the external os with sterile solution on a swab until all visible mucus and debris are removed. Sterile cover 30 is packaged with cannula 20 inserted. When the ring containing lock 70 is pulled, cover 30 is stretched taunt over cannula 20 and is locked by twisting to catch flanges 72 in slots 74. (FIGS. 7 and 8) Sterile lubricant is applied to cover 30 at its tip and the device is gently inserted into the cervix to the point of resistance at the internal os (at least 2.5 cm deep). Outer cannula 20 will not go further than the internal os and this location will be clearly felt by the user.

Once outer cannula 20 is positioned at the internal os, a standard endometrial sampler 40 is inserted into cannula 20 thus breaking cover 30 which snaps back to ring lock 70 outside of the vagina. This admits sampler 40 into the uterine cavity without allowing it to contact any vaginal or cervical surfaces. The endometrial sample is collected as usual and sampler 40 is carefully removed from cannula 20 which is still uncontaminated. The sample is deposited into sterile media for bacteriology examination and the device is removed from the cervix and disposed of in a contamination waste container.

Figure 6B:
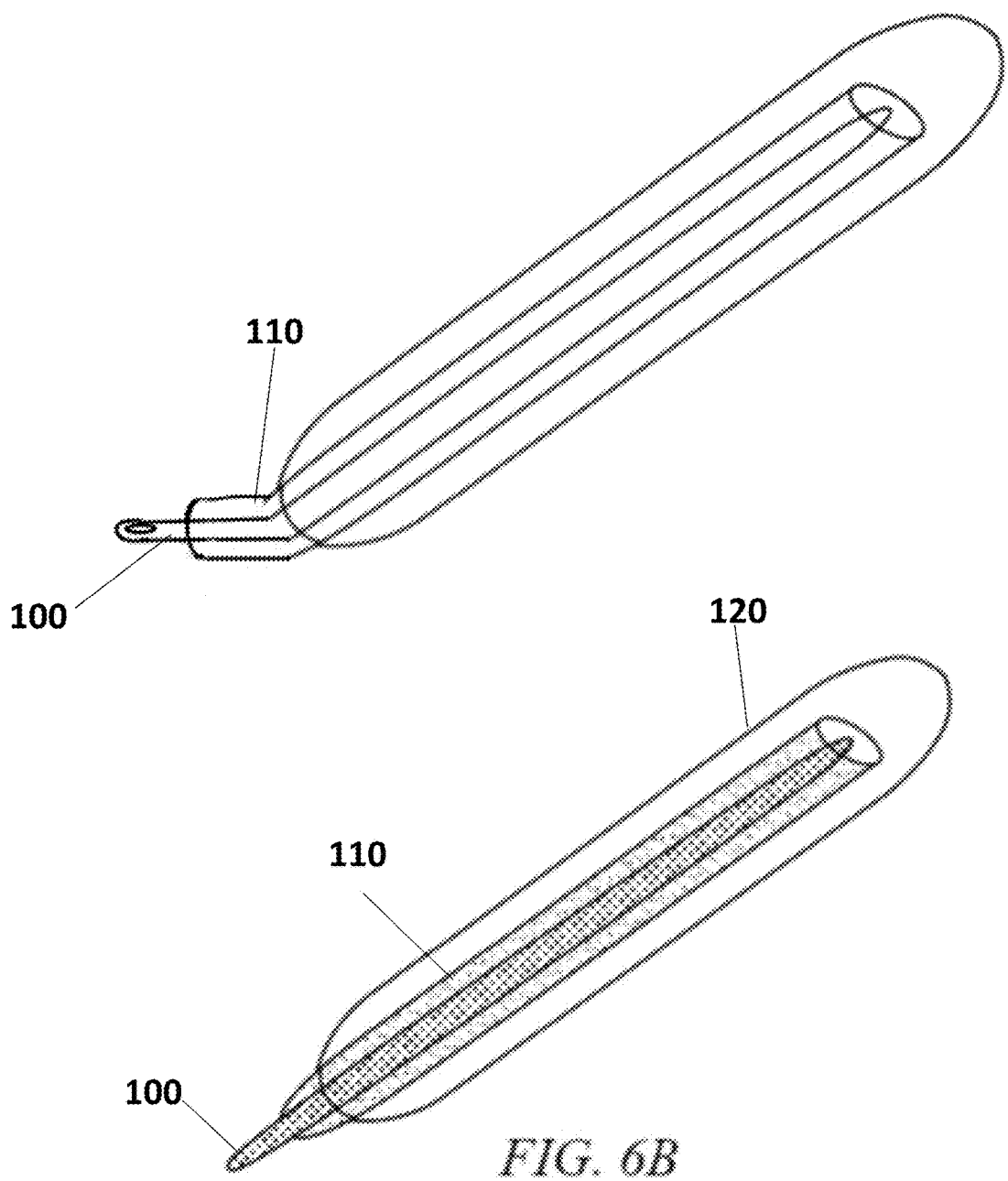

The most basic concept of the SUSC device is a dual layer of protection for sampler 100 against contamination (FIG. 6B). The SUSC device may consist of 2 main components assembled as one unit. The first component consists of cannula 110 comprising an about 200 mm long sterile tube having an about 5 mm diameter. Cannula 110 may be slightly tapered at one end and may have 2 locking flanges at the opposite end.

The second component is cover 120 comprised of a sterile lubricated elastomeric cover having an about 6 mm diameter and a length of about 10 cm. Cover 120 may have a closed end and an open end with the open end finished with an about 20 mm diameter hard plastic ring containing a locking mechanism.

In use, sterile sampler 100 is inserted into cannula 110. Outer cover 120 may be either rigid or flexible and manufactured of various materials including, but not limited to, metal, plastics, latex, and silicone. The purpose of outer cover 120 is to protect both cannula 110 and sampler 100 from the flora of the vagina and cervix. Cover 120 completely encloses the second end of cannula 110 as it is inserted into the vagina, cervix, and/or uterus. Once in place, cannula 110 is advanced through cover 120. Thus cover 120 might be made of thin material, such that cannula 110, or sampler 100 housed within cannula 110, can break though the first end of cover 120, by simply pushing cannula 110 or sampler 100 through cover 120.

Figure 6C:
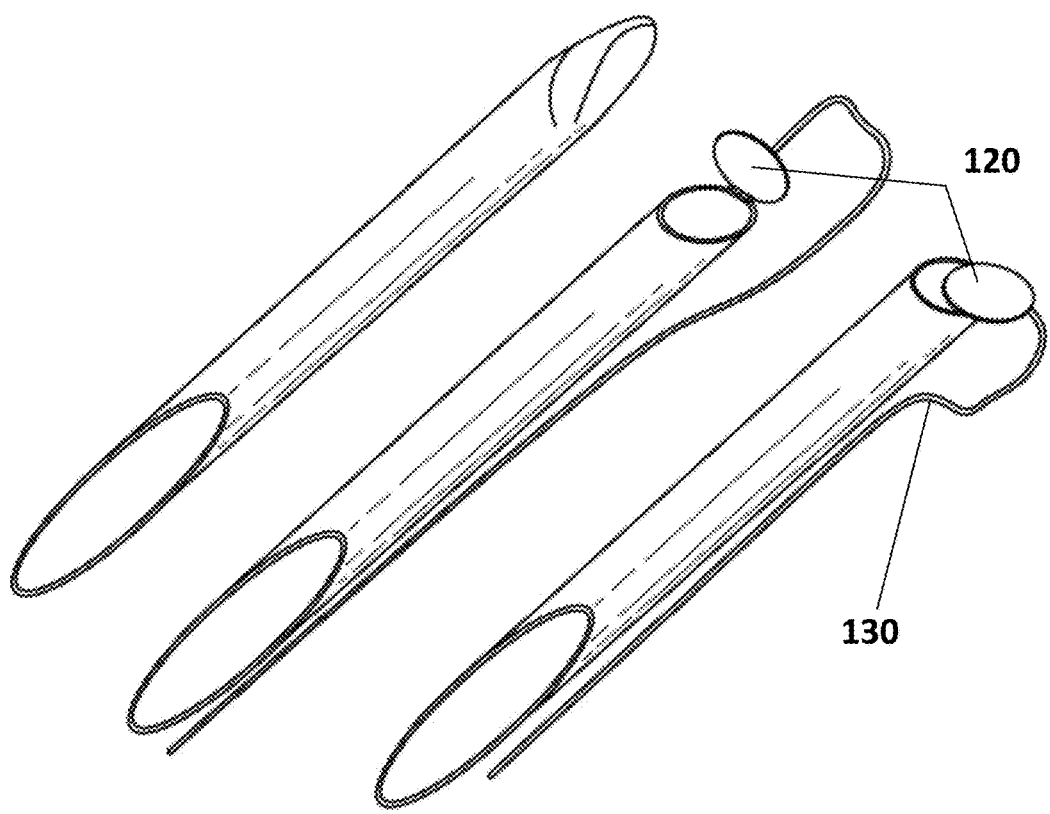

Alternatively, in another embodiment, the first end of cover 120 may be pulled open to reveal cannula 110 (FIG. 6C). In this embodiment, cover removal means 130 are provided which attach to first end of cover 120 to remove cover 120. The cover removal means 130 may be any means known by those of ordinary skill in the art as being capable of removing a cover.

In either case cover 120 may naturally retract due to elastic forces, or may be retracted mechanically, to reveal the tip and shaft of cannula 110. Cannula 110 may be open-ended on both first and second ends or alternatively may be closed on one end. Additionally cannula 110 may be rigid or flexible and manufactured of various materials including, but not limited to, metal, plastics, latex, or silicone.

Figure 8:
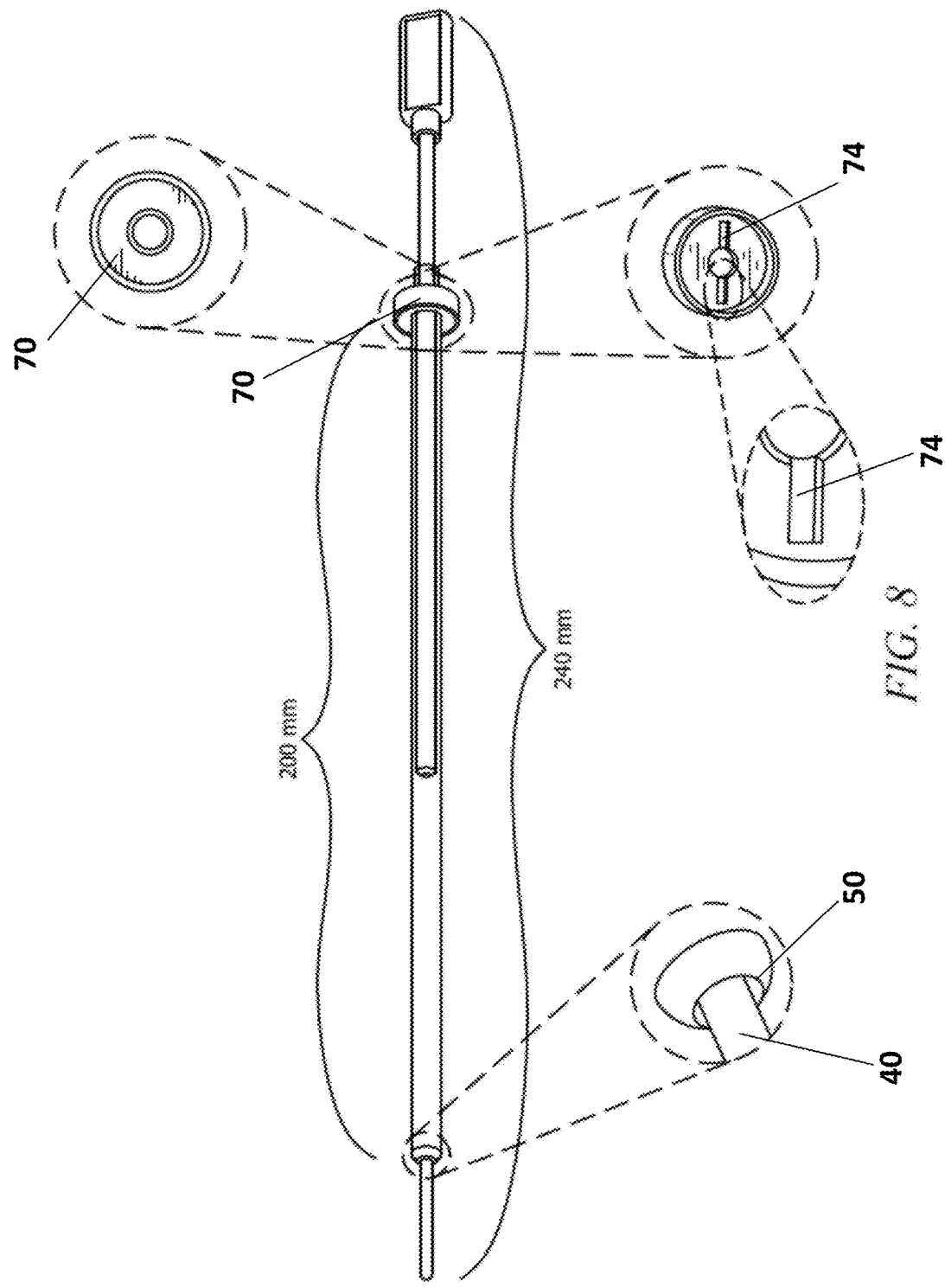
FIG. 8 is an image depicting the dimensions of the SUSC device.

The SUSC device of FIG. 6A was designed and analyzed based on the outer cannula with a protective cover (concept C, table 2) design. As stated above, device 10 has three main components: outermost protective cover 30, outer cannula 20, and sampler 40 (FIGS. 6A, 7, and 8). In an embodiment, outermost protective cover 30 may be made of an elastomeric material, such as latex, which can be stretched to a maximum length of 180 mm to give maximum elastic stretch at first end 22 of outer cannula 20. The use of an elastomeric material in cover 30 allows cover 30 to be easily broken when penetrated by sampler 40 once device 10 is positioned correctly and just prior to sampling. Outer cannula 20, which houses sampler 40, may have an outer diameter of about 5 mm, an inner diameter of about 3 mm, and a wall thickness of about 2 mm. First end 22 of outer cannula 20 contains an orifice that may be about 3-mm in diameter for sampler 40 to pass through to collect the samples. Sampler 40 may be about 240 mm in length, about 2.5 mm in diameter, and may have a wall thickness of about 1 mm. Orifice 45 is positioned on the side of first tip of sampler 40. Tissue samples are drawn through orifice 45 and into sampler 40 by using plunger 60 to create a vacuum. Each component of SUSC device 10, with the exception of outer protective cover 30, may have an about 20° angle at each end to facilitate insertion through the vagina.

Device 10 is shown in use in FIGS. 7A-C. As shown in FIG. 7A, plunger 60 is positioned within sampler 40 and sampler 40 is inserted into inner lumen of outer cannula 20. Cover 30 is placed around first end 22 of outer cannula 20 so that lock 70 is positioned distally. Cover 30 is then stretched distally down cannula 20 until lock 70 is positioned on second end 24 of cannula 20. Lock 70 is used to secure cover 30 in place over cannula 20 for insertion of device 10 into the vagina/uterus. Once device 10 is positioned correctly within the female reproductive tract, sampler 40 is advanced proximally up the shaft of cannula 20 until first end of sampler 40 pierces cover 30 (FIG. 7B). As shown in FIG. 7C, once sampler 40 pierces through cover 30, cover 30 retracts distally down cannula 20. Plunger 60 is then advanced and a sample is taken. Once the sample is taken, sampler 40 is retracted back into cannula 20 and device 10 is removed from the vagina.

FIG. 8 depicts exemplary measurements for device 10 as well as exploded views of lock 70. Lock 70 may have slots 74 for locking flanges 72 positioned on outer cannula 20 which assist in securing cover 30 over cannula 20. This locking mechanism is exemplary and many types of locking mechanisms may be used and are herein contemplated.

In an embodiment, the SUSC device may be fabricated using polyethylene tubing for outer cannula 20, a current endometrium sampler 40, and latex finger cot for protective cover 30. The prototype device was tested using a Luria-Bertani (LB) agar test. In a test tube, there were two layers of LB agar, the bottom layer was sterile and the top layer was enriched with *Escherichia coli* (ATCC 25922). Then, 8 mL of LB agar media was placed in four 15 mL BD Falcon tubes (BD Biosciences), and then allowed to solidify at room temperature. Next, each tube was inoculated with $1.0\times10^5$ colony-forming units (CFUs)/mL of Escherichia coli cells before one hour of incubation at 37° C.

The fabricated prototype device was then used to collect an agar sample from the sterile bottom layer within the test tube. The collected sample was released into another tube containing 4 mL of sterile LB broth. This tube was then incubated at 37° C. under light agitation for an hour. After the incubation period, 500 µL of the liquid culture was analyzed at $OD_{600}$ and the number of bacterial cells was calculated. Then, a 100-µL sample of the liquid culture was plated in triplicate on LB-agar plates incubated at 37° C. overnight. The controls were as follows: (1) a swab of bacteria from the contaminated layer, (2) sampling with only the sampler and (3) sampling with the sampler passing through the outer cannula without the finger cot. This test was used to ensure that the SUSC device could collect a sample of the sterile bottom-layer agar despite passing through the highly contaminated environment of the upper agar layer. The test found that the device was capable of collecting an uncontaminated sample.

Figure 9:
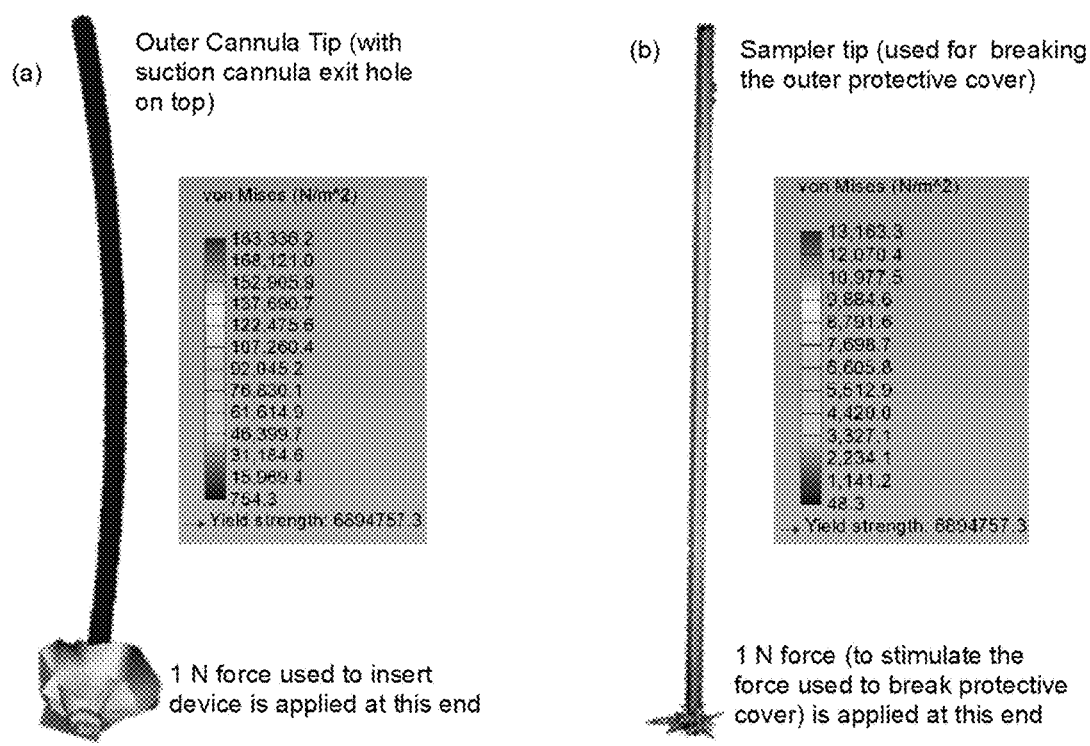
FIGS. 9A-B is a series of images depicting the stress distribution in FEA images. A 1-N force was applied to (a) outer cannula and (b) sampler with low-density PPE as the test material.

To simulate insertion of the device into the vagina, a 1N force was applied to the device components, and the resulting bending and deformation was measured. The first simulation was for testing the potential bending of the outer cannula during insertion in the vagina. The second simulation was for testing the ability of the sampler to break the stretched protective cover on the outer cannula before sampling. FIG. 9(a) shows the stress distribution after applying a 1-N force to the external end (the end not being inserted into the vagina) of the outer cannula made of a low-density polyethylene (PPE). This simulates the force applied on the outer cannula by the stretching of the protective cover. FIG. 9(b) shows the results for a 1-N force applied to the sampler to simulate the force associated with breaking the protective cover.

For this particular simulation, the outer cannula experienced no areas of critical stress. On the other hand, the tip sampler, which is used to break the protective cover, was found to be under critical stress however, the component was not deformed. Therefore, both the outer cannula and sampler are expected to withstand the forces caused by stretching the protective cover and breaking the protective cover. In both cases, the yield strength (the stress which the material deformed plastically) of the low-density polyethylene was 6,894,757.3 $N/m^2$. Based on the applied force, the maximum stress for the outer cannula was 404,763.1 $N/m^2$; for the sampler, 13,163.3 $N/m^2$.

Figure 10A:
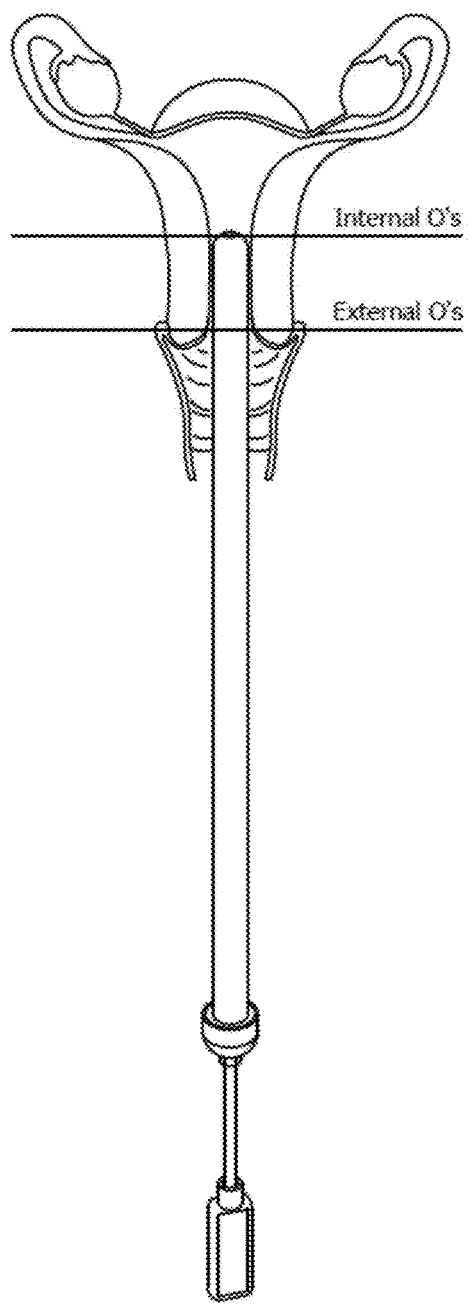
FIGS. 10A-B is images depicting an illustration of the operation of the SUSC device. (a) SUSC insertion with protective cover in the lock position on the outer cannula, and (b) sampler deployment and protective cover retraction.
Figure 10B:
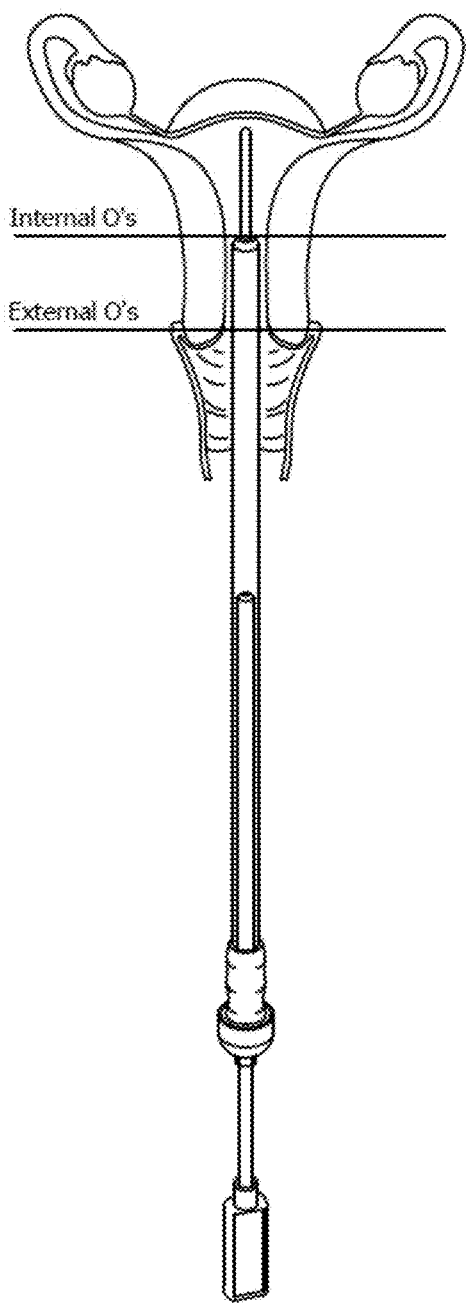

The SUSC device should be used only by licensed gynecological healthcare providers in a sterile clinical setting. Following are the proposed steps for operating the SUSC (FIG. 10): Lubricated sterile protective cover 40 is pulled toward the operator and locked so that it covers cannula 20 completely. SUSC device 10 is then inserted through the vagina through the previously cleansed cervix until it reaches the internal os. Given the diameter of cannula 20, there will be resistance at the internal os and this location will be clearly felt by the user. Once cannula 20 is positioned at the internal os, the protective cover 30 is stretched on the body of outer cannula 20 and sampler 40 is advanced until protective cover 30 breaks and retracts to lock 70, outside the vagina. Sampler 40 can then be advanced into the uterus for endometrial collection. Once the sample is collected, sampler 40 is retracted back into cannula 20 and device 10 is removed from the uterus and the sample is deposited into sterile media for culture or genetic analysis.

Figure 11:
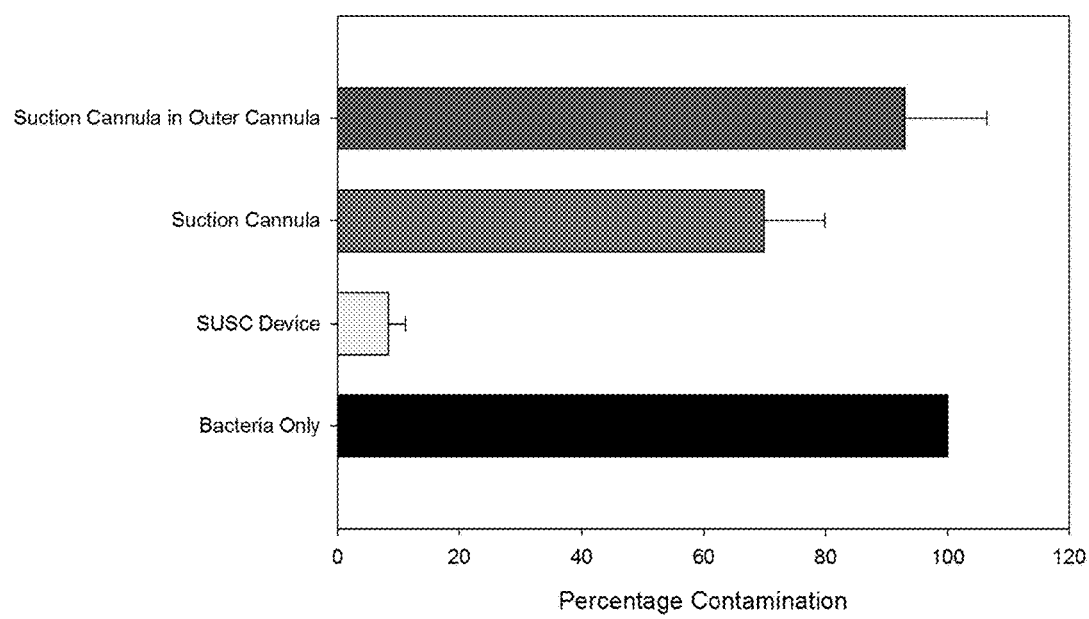
FIG. 11 is a graph depicting Specimen contamination resulting from various techniques used to sample a sterile agar layer confined beneath a contaminated upper layer.
Figure 12:
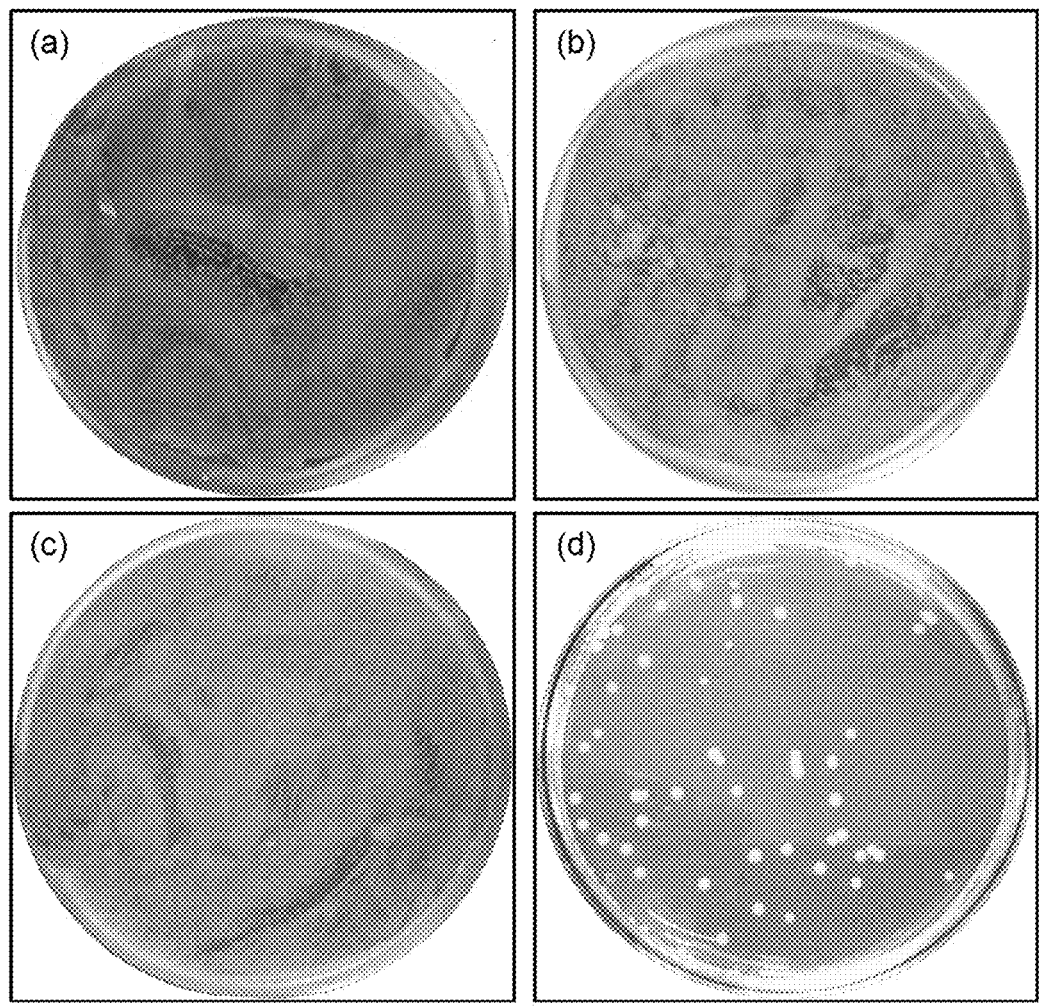
FIGS. 12A-D are a series of images depicting LB-agar culture plates for samples collected from a sterile agar layer confined beneath a contaminated upper layer. Collection techniques: (a) no technique; swab from the E. coli-contaminated upper layer, (b) sampler only, (c) sampler in outer cannula (no protective covering), and (d) the proposed SUSC device.

The SUSC device and three different sampling methods were tested to analyze the effectiveness of the device. These three sampling methods were: use of a swab, use of a sampler only, and use of a sampler inside an outer cannula. When using the different approaches to sample a sterile agar layer confined beneath an upper contaminated layer, the SUSC device resulted in much lower sample contamination as shown in FIG. 11. Compared to a swab from the contaminated layer (100% contamination), using a bare sampler to penetrate the upper layer and sample the lower sterile layer resulted in a 27% reduction in contamination. Using a sampling device in an outer cannula (no protective cover) resulted in only a 7% reduction in contamination. In contrast, sampling with the SUSC device resulted in 92% reduction in contamination. These percentages were obtained by analyzing liquid cultures using optical density at 600 ($OD_{600}$). It is believed that the level of contamination on the sample, although minimal, could be the result of human error during sampling and that further practice in using the device would help to decrease this contamination. Compared to the plate streaked with a sample of the contaminated layer (FIG. 12(a)), the plates streaked with samples from the sampler only (FIG. 12(b)) and the suction device in the outer cannula with no protective covering (FIG. 12(c)) show similar confluent bacterial overgrowth. On the other hand, only a few isolated colonies were observed on the plates streaked with samples from the SUSC device as shown in FIG. 12(d).

A single-use sterile uterine sampler cover (SUSC) device for collection of uncontaminated uterine specimen samples for a more accurate diagnosis of PID and other endometrial infections was presented. The SUSC device consists of three components: an outermost protective cover, an outer cannula, and a sampler. The protective cover of the SUSC device aims to protect the device during insertion through the naturally contaminated vagina and cervix for the collection of uterine specimens. The main advantage of the present device is that its protective cover and sterile technique can be used with any currently available endometrial sampler with an outer diameter of up to 3 mm, such as the Pipelle, Explora curette or Select Cell. Once the SUSC device is in place, a delivery cannula, as opposed to a sampler, could be inserted into the uterus for delivery of nano-encapsulated drugs to the uterine cavity for treatment of infection.

Chitosan Particle Formation by Ionic Gelation

The inventors have conducted a systematic study of the preparatory variables of the ionic gelation method and their effect on the chitosan particles characteristics. Multivariate analysis was used to determine the optimum model of preparatory variables that influence particle size. The variables selection was performed using multiple regression analysis through two methods: Akaike's information criterion (AIC) and F-statistics/p-value selection methods. This optimal model increases understanding of particle size formation using the ionic gelation method to enable mass production of particles of desired size for drug delivery systems.

Chitosan particles have been extensively explored as a promising drug delivery system due to their muco-adhesive property, which is of great value for delivering particle-encapsulated drugs to intracellular sites. As described previously, the ionic gelation method is one of the most commonly used methods for preparing these particles. However, previous work only studied one preparatory variable at a time, and did not provide a systematic analysis of all the preparatory variables at once. The inventors have identified the most relevant methodological parameters in determining chitosan particle size to control particle formation for particular delivery systems.

The particles were characterized in terms of their morphology and particle size distributions. Two statistical selection methods were applied to these data to build an optimal model: Akaike's information criterion and F-statistics/p-values selections. These statistical analyses were used to identify preparatory variables that were statistically significant in determining the average diameter of the chitosan particles. The analysis of the preparatory variables lays the groundwork for a better understanding of chitosan particle size variation when synthesized by the ionic gelation method. This can potentially lead to better control of particle size formation to enable the mass production of chitosan particles using the ionic gelation method for specific drug delivery systems.

Materials and Methods

Chitosan powders (deacetylation of 75%) were obtained from Sigma Aldrich (USA). Sodium tripolyphosphate (TPP) powder was supplied by Sigma Chemical Company (USA). Doxycycline, phosphate buffered saline (PBS), and acetic acid were obtained from Fisher Scientific (USA). All other chemicals were of analytical grade and were obtained from a variety of vendors.

Preparation of Chitosan Nanoparticles

Figure 13:
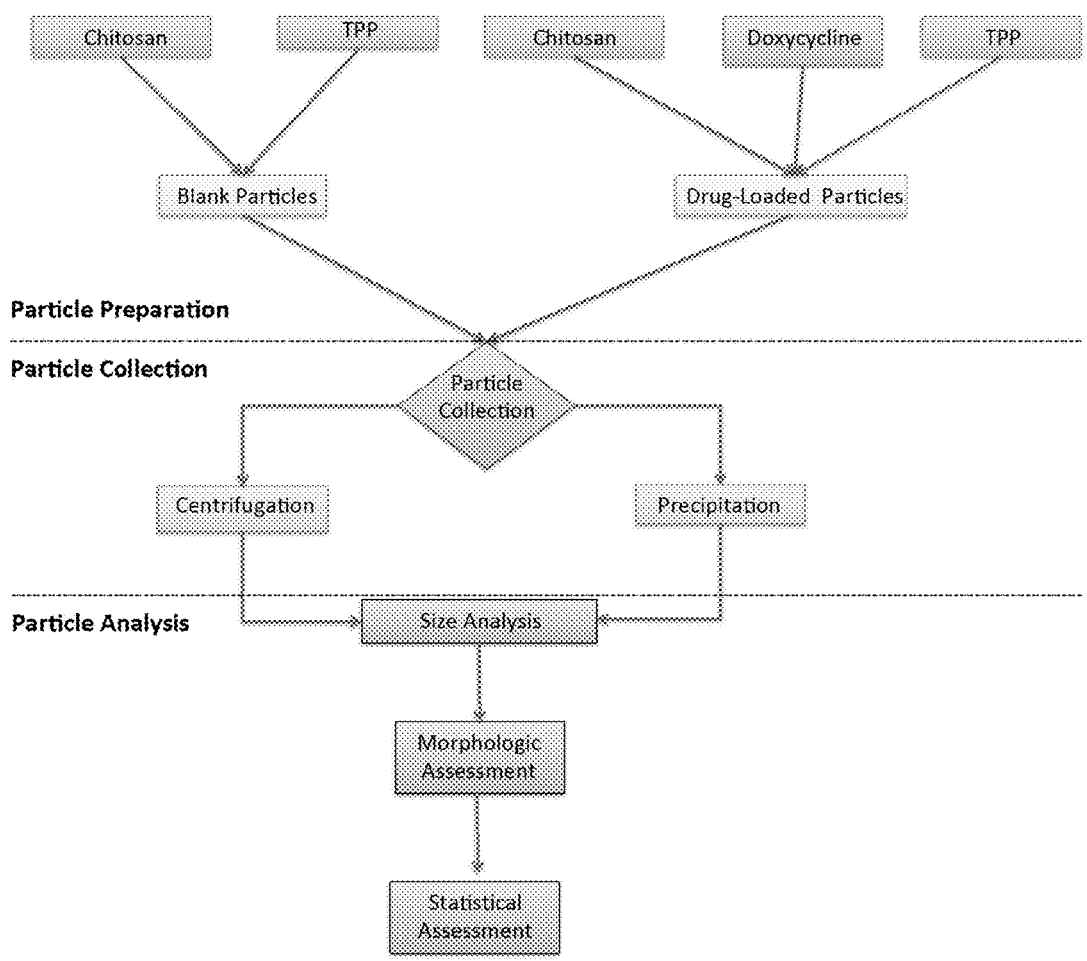
FIG. 13 is an image depicting the schematic representation of the variables involved in the overall process for preparing chitosan nanoparticles.

Chitosan particles were prepared using the ionic gelation method of Clavo et al. (Shanmuganathan S, Shanumugasundaram N, Adhirajan N, Ramyaa-Lakshmi T S, Babu M. Preparation and characterization of chitosan microsphere for doxycycline delivery. *Carbohydrate Polymers.* 2007:201-211). The basic procedure entailed mixing the polymer with a crosslinker to prepare blank (no-drug) particles. For drug-loaded particles, doxycycline was added to the mix as shown in FIG. 13. Sixty-four different formulations that consisted of different combinations of chemical constituents and procedural steps were used to create the chitosan particles (Table 3). In earlier experiments done by the inventors, the effect of using a wider range of acetic acid concentrations (0.25M, 0.50M, and 0.75M) to dissolve the chitosan powder was also evaluated.

Chitosan solution was prepared by dissolving the chitosan powder—10 kDa or 60 kDa (Table 3, variable $X_1$)—in acetic acid or water ($X_3$) for a final concentration (variable $X_2$) of 0.1% or 0.2% weight by volume (w/v). This solution was magnetically stirred at 400 rpm at room temperature and allowed to protonate for 1 hour or 24 hours (variable $X_4$). The cross-linker, sodium tripolyphosphate (TPP), was prepared by dissolving it in acetic acid or water ($X_6$) to achieve final TPP concentrations ranging from 0.21% to 0.84% w/v ($X_5$). The various combinations of chitosan and TPP concentrations produced three different chitosan:TPP ratios ($X_9$): 1:1, 1:2, 1:3, 1:4, 1:5, 1:8, 3:1, and 6:1.

Some particles were prepared as blanks that contained no drug, and other particles were prepared to encapsulate the model drug, doxycycline (Table 3, variable $X_7$). Doxycycline stock solution (200 mg/mL) was prepared by dissolving doxycycline powder in nanopure water. To initiate ionic gelation (particle formation), the chitosan, TPP, and drug solutions were combined (FIG. 13). Blank nanoparticles were formed by dropwise addition of TPP to a chitosan solution that was being magnetically stirred. Drug-loaded particles were formed by dropwise addition of 100 µL of doxycycline to the chitosan solution before dropwise addition of TPP, or by dropwise addition of doxycycline to a stirred TPP solution before dropwise addition of chitosan (variable $X_8$). The blank and drug-loaded solutions were allowed to synthesize particles for 1, 2, or 24 hours ($X_{10}$) under magnetic stirring at room temperature. The particles were then collected and were centrifuged at 10,000 rpm for 5 minutes or were allowed to precipitate at room temperature until supernatant is clear and pellet is obvious ($X_{11}$). The resulting pellet or precipitate was then washed and resuspended in either nanopure water or phosphate buffered saline, PBS ($X_{12}$).

Physical Characterization of Nanoparticles

Particle size distributions were determined with a Microtrac Particle Size Analyzer (measures particles sizes from 0.8 to 6500 nanometers), which measures dynamic light scattering by particles. All analyses were performed on samples diluted in 1 mL nano-pure water. Morphology of the chitosan nanoparticles was examined using a JEOL 1400 transmission electron microscope (TEM). TEM samples were prepared by placing a drop of resuspended nanoparticles (blank or drug-loaded) onto a formvar-coated copper grid that was allowed to dry before TEM analysis.

Variable Selection

To quantitatively assess and determine which of the twelve preparatory parameters (Table 3) had the greatest influence on particle size, a series of multivariate linear models were constructed. Multivariate linear regression modeling is an approach used to model the relationship between a dependent variable and several independent variables. (Pulsiripunya C, Youngchaiyud P, Pushpakom R, Maranetra N, Nana A, Charoenratanakul S. The efficacy of doxycycline as a pleural sclerosing agent in malignant pleural effusion: a prospective study. *Respisology.* 1996;

TABLE 3

List of variables and values used in the formulation of the chitosan nanoparticles

| Variable | Symbol | Values | | | | |
|---|---|---|---|---|---|---|
| Chitosan Type | $X_1$ | 10 kDa | | 60 kDa | | |
| Chitosan Concentration | $X_2$ | 0.1 w/v % | | 0.2 w/v % | | |
| Chitosan Dissolving Solution | $X_3$ | Water | | Acetic Acid (0.25M) | | |
| Citosan Protonation Time | $X_4$ | 1 hour | | 24 hours | | |
| TPP Concentration | $X_5$ | 0.21 w/v % | 0.42 w/v % | 0.60 w/v % | 0.75 w/v % | 0.84 w/v % |
| TPP Dissolving Solution | $X_6$ | Water | | Acetic Acid (0.25M) | | |
| Drug | $X_7$ | Doxycycline | | None | | |
| Order of Combination | $X_8$ | Chitosan + Doxy + TPP | | TPP + Doxy + Chitosan | | |
| Chitosan:TPP Ratio | $X_9$ | 1:2 | 1:4 | 1:6 | | |
| Synthesis Time | $X_{10}$ | 1 hour | 2 hours | 24 hours | | |
| Centrifugation | $X_{11}$ | Yes | | No | | |
| Wash/Reconstitution Solution | $X_{12}$ | Water | | PBS | | |

1(1):69-72). The models were then ranked using Akaike Information Criterion (AIC) and F-statistics/p-value methods. Both methods are independent from the distribution of the variables; in other words, both work well for normal and non-normal data distributions. The twelve preparatory variables investigated, $X_n$, are listed in Table 3; average particle diameter, Y, was the dependent variable. All statistical analyses were performed using MATLAB (version 2009b).

The AIC selection approach builds the simplest possible optimal model to explain observed variation in an experimental outcome, which in our case is the mean particle diameter Y. (Chien Y. *Novel Drug Delivery Systems*. Vol 50. New York Marcel Dekker; 1992; Weisberg S. *Applied Linear Regression*. 2nd ed. New York: John Wiley; 1985; NellUker C, Uhrzander F, Tyrcha J, Karlsson H. Mixture models for analysis of melting temperature dat. *BMC Bioinformatics*. 2008; 9:1-6; Anderson D R, Burnham K P, Thompson W L. Null Hypothesis Testing: Problems, Prevalence, and An Alternative. *Journal of Wildlife Management*. 2000; 64(4):912-923). The method performs stepwise selection of significant preparatory variables through forward addition based on the AIC value, which measures how much variation in outcome, Y, can be accounted for by each individual variable. AIC considers the number of observations (n); the number of explanatory variables (K) and the residual sum of squares (RSS) for each model and the AIC value is calculated based on equation 1.

$$AIC = n \log_e(RSS/n) + 2K \quad (1)$$

The F-statistics/p-value variable-selection method, like the AIC-based method, also builds an optimal model based on the empirical data set—identifying those variables that exert the greatest influence on particle diameter—but does so by selecting variables with significant p-value for the final model. This non-parametric, permutation-based method assesses each variable's statistical significance and its influence on the variation in the outcome, Y, before selecting it to the final model. Variables are sequentially added by selecting the variable that yields the largest partial F-statistic with significant p-value and corresponding adjusted $R^2$. To test the significance of each variable in the model, an F-statistics test was performed using a level of significance, alpha ($\alpha$), of 0.05.

Conditional tests were conducted for both selection methods to first examine the independent effect of each preparatory variable on mean particle diameter. For AIC-based selection, the conditional test is used to select the order of variable entry into the final model. Marginal tests, in contrast to the conditional tests, examine the effect of each variable on Y after taking into account the effects of preparatory variables previously selected during the stepwise variable-selection procedure.

Statistical Selection of Influential Preparatory Variables

The AIC-based variable-selection method identified four of the twelve variables as substantially contributing to variation of mean particle diameter (Y): chitosan-to-TPP ratio ($X_9$), wash/resuspension solution ($X_{12}$), synthesis time ($X_{10}$), and TPP concentration ($X_5$). Conditional testing was conducted first to assess the independent effect of each of the twelve preparatory variables and to select the first variable to enter in the final model (Table 4). A variable's AIC value is of great importance because it expresses the strength of the variable's influence on particle size variation: the smaller the AIC value, the more of the Y variation that is explained. Each variable has an AIC value, which is assigned a corresponding weight (Wts). The variable with the lowest AIC value was assigned a weight of zero and the remaining weights were scaled accordingly.

TABLE 4

Results of the conditional test using the AIC-based stepwise forward selection. Variables selected to be in the final model are shown in bold.

| Variables | AIC | Wts | $R^2$ | $R^2$ adj |
|---|---|---|---|---|
| Chitosan:TPP Ratio, $X_9$ | 952.4053 | 0 | 0.3105 | 0.2994 |
| Chitosan Type, $X_1$ | 963.4904 | 11.0851 | 0.1802 | 0.1669 |
| TPP Concentration, $X_5$ | 971.2121 | 18.8068 | 0.0750 | 0.0601 |
| Chitosan Concentration, $X_2$ | 972.0659 | 19.6606 | 0.0626 | 0.0475 |
| Wash/Resuspension Solution, $X_{12}$ | 972.3683 | 19.9630 | 0.0582 | 0.0430 |
| Chitosan Dissolving Solution, $X_3$ | 972.8854 | 20.4801 | 0.0505 | 0.0352 |
| TPP Dissolving solution, $X_6$ | 974.4036 | 21.9983 | 0.0277 | 0.0121 |
| Order, $X_8$ | 975.5816 | 23.1763 | 0.0097 | −0.0063 |
| Protonation Time, $X_4$ | 976.0933 | 23.6880 | 0.0017 | −0.0144 |
| Drug, $X_7$ | 976.1125 | 23.7072 | 0.0014 | −0.0147 |
| Synthesis Time, $X_{10}$ | 976.1614 | 23.7561 | 6.6606e$^{-04}$ | −0.0155 |
| Centrifugation, $X_{11}$ | 976.2040 | 23.7987 | 5.0692e$^{-07}$ | −0.0161 |

Table 5 shows the variables selected for the optimal model selected by the AIC method. The variables selected for inclusion in this final model may not have had the lowest AIC values in the conditional testing of each individual variable but together in the final model they resulted in the lowest cumulative AIC value. In this case, $R^2$ values correlate well with the AIC values within the final model, which can explain 58% of the total variation in particle diameter.

TABLE 5

List of variables selected for inclusion in the optimal model using the AIC-based selection method.

| Variables | Partial F | P | Partial $R^2$ | Partial $R^2$ adj |
|---|---|---|---|---|
| Chitosan:TPP Ratio, $X_9$ | 27.9262 | 1.0000e$^{-03}$ | 0.3105 | 0.2994 |
| Wash/Resuspension Solution, $X_{12}$ | 17.6342 | 1.0000e$^{-03}$ | 0.1546 | 0.1410 |
| Synthesis Time, $X_{10}$ | 10.7019 | 0.0030 | 0.0810 | 0.0661 |
| TPP Concentration, $X_5$ | 4.1789 | 0.0500 | 0.0300 | 0.0144 |

The F-statistics/p-value stepwise method selected the same four variables as being significant in contributing to variation in particle diameter for the optimal model (Table 6). As with the AIC-based method, conditional testing on each of the twelve variables was conducted first. The fact that both methods selected the same four variables for the optimal model (Tables 5 and 6) is a strong indication of the significance of these variables in determining mean particle diameter.

TABLE 6

List of variables selected for inclusion in the optimal model based on the F-statistics/p-value selection method

| Variables | AIC | Wts | $R^2$ | $R^2$ adj |
|---|---|---|---|---|
| Chitosan:TPP Ratio, $X_9$ | 952.4053 | 0.9958 | 0.3105 | 0.2994 |
| Wash/Resuspension Solution, $X_{12}$ | 938.3569 | 0.8535 | 0.4652 | 0.4476 |

TABLE 6-continued

List of variables selected for inclusion in the optimal model based on the F-statistics/p-value selection method

| Variables | AIC | Wts | $R^2$ | $R^2$ adj |
|---|---|---|---|---|
| Synthesis Time, $X_{10}$ | 930.1306 | 0.7613 | 0.5461 | 0.5234 |
| TPP Concentration, $X_5$ | 928.1074 | 0.2282 | 0.5761 | 0.5474 |

Finally, the four selected variables were entered into a multiple linear regression model for the purpose of calculating the overall F-statistics/p-value and an $R^2$ value to express the overall significance of the model. The resulting equation, equation two with coefficients for mean particle diameter (Y) was as follows:

$$Y = 6821 - 1520 X_9 - 1383 X_{12} + 2.2 X_{10} - 1715 X_5 \quad (2)$$

The ratio of chitosan to TPP, $X_9$, was identified as the single most important variable (p=0.001) in determining mean particle size: the higher the ratio, the smaller the mean particle diameter. This variable explains 31% of the variation in particle size (as indicated by the partial $R^2$ value of table 4-4). This finding—that the chitosan:TPP ratio plays a role in determining the size of the nanoparticles—is in agreement with the non-statistical work of Zhang et al, which concluded that particle sizes are dependent upon the chitosan-to-TPP ratios. (Zhang H, Wu S, Tao Y, Zang L, Su Z. Preparation and Characterization of Water-Soluble Chitosan Nanoparticles as Protein Delivery System. *Journal of Nanomaterials*. 2009; 2010:1-5).

The identity of the wash/resuspension solution, $X_{12}$, was also identified by both selection methods as being significant (p=0.001). The addition of this variable to the model increased the overall $R^2$ value from 31% to 47% (Table 6). In other words, the two variables in the model thus far explain 47% of the variations in mean particle diameter, Y. The negative coefficient of this categorical variable indicates that one solution increases the particle size while the other decreases it. In this case, using water resulted in larger particle diameters while PBS produced smaller particles.

The third significant variable selected for the final model was synthesis time, $X_{10}$ (p=0.0030). As synthesis time increases, particle size also increases. Allowing more time for ionic-gelation synthesis may result in particle-to-particle linking. The last variable of significance selected for the regression model was the TPP concentration, $X_5$ (p=0.05). According to the model, increasing the TPP concentration results in smaller particles. Clavo et al. also reported that an increase in TPP concentration produces smaller particles. (Bodmeier R, Chen H, Paeratakul O. A Novel Approach to the Delivery of Microparticles or Nanoparticles *Pharm Res*. 1989; 6:413-417).

Overall, the linear regression model (equation 2) was found to be significant (p=0.001), indicating that the mean particle diameter and the set of selected variables are significantly related. The optimal model containing these four variables accounts for 58% of the observed variation in mean particle diameter. Narrowing down the field of potentially influential preparatory variables from twelve candidates to four significant variables can lead to higher control of determining chitosan particle size.

Morphology and Particle Size Observations

The acidity of the solution used to initially dissolve the chitosan powder exerts a profound influence on particle formation. The use of nanopure water produced particles with no well-defined borders and severe clumping (FIG. 14a). With 0.25M acetic acid, the inventors saw nicely formed particles with more defined borders and with very little clumping (FIG. 14b). When the concentration of acid was increased to 0.50M, the particles were slightly formed but were not as well defined as the particles prepared in the 0.25M acid. Moreover, there were signs of chitosan degradation (FIG. 14c). At 0.75M, the inventors saw degradation of chitosan so no particles were formed (FIG. 14d).

In summary, using an acetic acid concentration higher than 0.25M seems to impede the proper formation of nanoparticles. Pure water is also unsuitable. Acetic acid with a concentration of 0.25M seems to provide a workable environment for the formation of well-defined spherical particles.

Centrifugation was not statistically selected as being significant in determining mean particle diameter, but quantitative observation using Nanotrac analysis indicated that centrifugation did affect particle size. FIG. 15 shows the particle size distribution of centrifuged and precipitated samples. Note that the centrifuged sample resulted in predominately microparticles whereas the precipitated sample resulted in mostly nano-sized particles.

TEM observations corroborated the conclusions drawn from equation 1 regarding the nature of the wash/resuspension solution. When particles were washed with nanopure water, centrifuged, and then resuspended in water, the resulting particle diameters were relatively large due to clumping of smaller particles (FIG. 16). In contrast, particles washed, centrifuged, and then resuspended in PBS were uniformly spherical and individually distinct, as shown in FIG. 17.

The inventors have shown that chitosan nanoparticles (drug-loaded or drug-free) prepared by the ionic gelation method can be controlled by specific adjustments of the variables involved. The impacts of twelve preparatory variables on particle size were studied using two statistics stepwise forward selection methods. The results of both statistics selection methods showed that the ratio of chitosan to TPP, wash/resuspension solution, synthesis time, and TPP concentration contribute to 58% of the variation in determining the particle size when prepared using the ionic gelation method. All four selected variables were found to be significant (p=0.001) in contributing to the particle size. Therefore, this statistical selection of variables can be used to better understand the impact of variables on the particle size, and to improve the preparation of particles using the ionic gelation method.

Synergistic Effects of Doxycycline-Loaded Chitosan Nanoparticles

The doxycycline-loaded nanoparticles (DCNPs) were prepared using a modified ionic gelation method with tripolyphosphate (TPP) as a cross-linker. The DCNPs were characterized based on size and size distribution, morphology, drug-release properties, antibacterial activity, and in vitro cytotoxicity. Results show that encapsulating doxycycline into chitosan nanoparticles could facilitate intracellular and/or extracellular delivery of the drug and thus improve the drug efficacy in the treatment of bacterial infections.

In recent years, drug encapsulation and delivery via small particles has garnered increasing interest. Encapsulation may help prevent adverse effects by protecting sensitive tissues from fast drug exposure while also improving drug efficacy by achieving slow, sustained release directly at the infection site. Having patients complete the entire treatment cycle would also increase the likelihood of complete pathogen elimination. These properties suggest that the encapsulation of doxycycline into biodegradable nanoparticles could be used to eventually improve treatment of PID via direct transcervical drug delivery.

A detailed investigation of chitosan nanoparticles as a potential carrier of doxycycline to improve drug delivery and treatment efficacy was performed. Two particle formulations were examined: formulation DCNP6 containing approximately 1.5 times the crosslinker concentration of the other formulation named DCNP4. As a first step toward assessing this potential, the inventors used an ionic gelation method to synthesize blank and doxycycline-loaded chitosan nanoparticles (DCNPs), which were characterized in terms of several properties relevant to clinical efficacy: particle size, shape, encapsulation efficiency, antibacterial activity, and in vitro cytotoxicity.

Materials and Methods

Doxycycline, phosphate buffered saline (PBS), Millipore WST-1 Cell Proliferation Assay, and acetic acid were obtained from Fisher Scientific (USA). Sodium tripolyphosphate (TPP), fetal bovine serum, medium 199, and MCDB 105 medium were supplied by Sigma Chemical Company (USA). Partially (75%) deacetylated chitosan (60 kDa) derived from shrimp shells was obtained in powder form from Sigma Aldrich (USA). All other chemicals were of analytical grade and were obtained from a variety of vendors. *Escherichia coli* (ATCC 25922) was purchased from American Type Culture Collection.

Chitosan Nanoparticle Preparation

The chitosan nanoparticles were prepared using the ionic gelation method of Clavo et al. (Ko J A, Park H J, Hwang S J, Park J B, Lee J S. Preparation and Characterization of Chitosan Microparticles intended for Controlled Drug Delivery. *International Journal of Pharmaceutics*. 2002: 165-174). Chitosan powder was dissolved, 0.2% weight by volume (w/v), in 0.25M acetic acid; this solution was magnetically stirred overnight at a speed of 400 rpm at room temperature. The acetic acid protonates the amine group of the chitosan molecule, for a more stable interaction with the crosslinking agent and the drug.[59,105] (Tokumitsu H, Ichikawa H, Fukumori Y. Chitosan-Gadopentetic Acid Complex Nanoparticles for Gadolinium Neutron-Capture Therapy Therapy of Cancer: Preparation by Novel Emulsion-Droplet Coalescence Technique and Characterization. *Pharmaceutical Research*. 1999; 16(12):1830-1835; Burnham K P, Anderson D R. Kullback-Leibler Information as a Basis for Strong Inference in Ecological Studies. *Wildlife Research*. 2001; 28:111-119). The crosslinker, sodium tripolyphosphate (TPP), was prepared by dissolving the powder in 0.25M acetic acid at two different concentrations: 0.42% w/v (referred here as formulation 8, F8) and 0.60% w/v (formulation 10, F10). In a separate set of experiments, the inventors examined 64 different combinations of solutions and procedural steps, and identified these two formulations as consistently producing particles within a predictable formulation-specific size range.

Blank nanoparticles were formed by combining the chitosan and TPP solutions for a total volume of 2 mL; the chitosan-to-TPP ratio was 23:1 for F8, and 16:1 for F10. To initiate ionic gelation (nanoparticle formation), TPP was added dropwise to the stirred chitosan solution, and the combined solution was then stirred for an additional hour. Blank nanoparticles prepared using F8 (0.42% w/v TPP) are here referred to as BKCNP4 while blanks prepared using F10 (0.60% w/v TPP) are referred to as BKCNP6. The solution with precipitated nanoparticles was centrifuged at 10,000 rpm for 5 minutes, and the resulting supernatant was saved for later analysis of its doxycycline content. The particles in the microcentrifuge tube were washed/resuspended by adding 2 mL nanopure water, and the tube was again centrifuged at 10,000 rpm for 5 minutes. The second supernatant was removed and discarded as preliminary tests had shown that the second supernatant contained no doxycycline residue. Finally, the particles were resuspended in 2 mL nanopure water before further analysis.

A doxycycline stock solution was prepared by dissolving doxycycline powder in nanopure water to achieve a final concentration of 200 mg doxycycline per mL solution. Drug-loaded chitosan nanoparticles were then prepared according to the procedure outlined above, except that 100 μL of the doxycycline stock solution was added dropwise to the stirred chitosan solution just before the TPP addition. In every batch of DCNP solution, the final doxycycline concentration was 20 mg/mL. Drug-loaded chitosan nanoparticles prepared using 0.42% w/v TPP are here referred to as DCNP4; those prepared with 0.60% w/v TPP are referred to as DCNP6. All analyses of blank particles, drug-loaded particles, and supernatant were initiated within 24 hours of particle preparation.

Nanoparticle Characterization

Particle size distributions for blank nanoparticles and DCNPs were determined with a Microtrac Particle Size Analyzer, which measures dynamic light scattering by particles in solution. The analyses were performed on samples of nanoparticles suspended in 1 mL of nanopure water. The shapes of the blank particles and DCNPs were examined using a JEOL 1400 transmission electron microscope (TEM) with a 0.38 nm assurance for point to point images and 0.2 nm for lattice images. Particles to be used for TEM examination were first dried under vacuum and stored in the dark at 4° C. TEM samples were then prepared by depositing a drop of nanoparticles onto a formvar-coated copper grid, which was allowed to dry by vacuum before TEM analysis.

Encapsulation Efficiency

Incorporation of doxycycline into the particles was characterized by measuring the doxycycline contained in the centrifugation supernatant. Since the total amount of drug in each formulation batch was known (2 mL solution with a doxycycline concentration of 20 mg/mL), any doxycycline not found in the supernatant could be assigned to the particles. Doxycycline in the supernatant was quantified using a Nano-drop spectrophotometer (ND-1000), which has an absorbance precision of 0.003 at 1 mm (0.01 cm) path length. According to the Beer-Lambert Equation, the doxycycline concentration, c, is given by $c = A/\epsilon L$, where A is light absorbance at 220 nm wavelength, $\epsilon$ is the molar absorptivity coefficient (121.39 $M^{-1}$ $cm^{-1}$), and L is the path length (0.01 cm). All measurements were performed in triplicate (n=3). The encapsulation efficiency (EE,%) was calculated using equation 3:

$$EE(\%) = \frac{\text{Drug Used @ Synthesis (mg/mL)} - \text{Free Drug in Supernatat (mg/mL)}}{\text{Drug Used @ Synthesis (mg/mL)}} \times 100 \qquad (3)$$

Assessment of Drug Release

To determine the rate at which doxycycline was released by the nanoparticles, the particles were resuspended in a drug-free solution that was analyzed for doxycycline content at predetermined time interval. To begin, dried fresh nanoparticles of known antibiotic content were first resuspended in 2 mL of nanopure water. A small aliquot of this particle-laden solution was then added to PBS-ethanol solution to produce a final volume of 2 mL with an initial concentration of 100-μg doxycycline per mL. This solution was incubated at 37° C. under gentle agitation. At each specified time point (0.5, 1, 2, 3, 4, 5, 6, 7, 8, 16, and 24 hours) thereafter, the sample was centrifuged and the supernatant was isolated and analyzed by Nano-drop spectrophotometry to determine the amount of doxycycline in solution. All measurements were performed in triplicate (n=3) for each formulation. The percentage of drug released at each time point was calculated according to equation 4:

$$\text{Drug Release (\%)} = \frac{\text{Drug in Solution (µg/mL)}}{\text{Initial Drug in Particles (µg/mL)}} \times 100 \quad (4)$$

Antimicrobial Activity Assessment

To determine the antibacterial activity of the doxycycline-loaded chitosan nanoparticles, minimum inhibitory concentrations (MICs) and minimum bactericidal concentrations (MBCs) were evaluated. The procedures for both assays were adopted from Lee et al. (Blanchet F G, Legendre P, Borcard D. Forward Selection of Explanatory Variables. *Ecology*. 2008; 89:2623-2632). MIC is the lowest concentration of DCNPs that inhibits bacterial growth. For the analyses, a visual turbidimetric method was used. Freshly prepared nanoparticles, blank and drug-loaded, were UV-sterilized for ten minutes. The particles were then resuspended in a volume of sterile water sufficient to achieve a final doxycycline concentration of 100 µg/mL. A 500 µL aliquot of this solution with sterilized particles was added to a tube containing Luria-Bertani (LB) broth for a total volume of 2 mL. A serial dilution, with a dilution factor of 0.3, was performed for the remaining six tubes. A parallel series of experiments was also run using unencapsulated doxycycline.

Under sterile conditions, the tubes containing particles were inoculated with $1.0 \times 10^5$ colony-forming units (CFUs)/mL of *Escherichia coli* cells in LB broth, then incubated at 37° C. under agitation for four hours. Following the incubation, the tubes were assessed visually for the appearance of turbidity (i.e., bacterial growth). Among the tubes that showed no visual turbidity—that is, complete inhibition of visible *E. coli* growth—the one with the lowest doxycycline concentration was identified as the MIC tube for that series. All MIC tubes were analyzed to assess the amount of bacteria present by measuring optical density of the suspension at 600 nm ($OD_{600}$) and then calculating the number of bacterial cells present.

The MBC is the minimum concentration of DCNPs that will kill 99% of the bacterial cells initially present. To determine this value, 100 µL aliquots of liquid culture (broth+nanoparticles+bacteria) from each series' MIC tube and the two tubes prior (i.e., containing slightly more doxycycline) were plated and incubated at 37° C. overnight. As a positive control, an additional plate was plated with broth plus *E. coli* (no particles or drug); as a negative control, another plate was plated with broth plus blank particles plus *E. coli* (no drug). All samples were plated in triplicate. Plates were observed for colony growth, and the plate with the fewest colony colonies was identified as the MBC plate.

Cytotoxicity Assessment

Cytotoxicity of the DCNPs was determined by treating normal human ovarian surface epithelial (OSE) cells with different concentrations of doxycycline-loaded nanoparticles, then monitoring cell viability over the next five days. The OSE cells were cultured for 4 to 7 days in flasks containing medium199/MCDB105 media supplemented with 10% fetal bovine serum. The cells were removed from the flasks and counted, and then 100 µL of medium containing cells was added to the wells of a 96-well plate to give final cell concentrations of $5 \times 10^2$, $1.0 \times 10^3$, or $2.0 \times 10^3$ cells/mL. After 24 hours incubation at 37° C., the cells were treated with blank nanoparticles, DCNP4 (1 and 2 µg/mL), DCNP6 (1 and 2 µg/mL), or unencapsulated doxycycline (1 and 2 µg/mL). The plate was then incubated at 37° C. Bright microscopy was used to examine the cell morphology after treatment just before the assessing for cytotoxicity. Cytotoxicity was assessed on days 1, 3, and 5 by WST-1 assay. WST-1 assay reagent (10 µL) was added to each well, followed by incubation for another 4 hours at 37° C. and then spectrophotometric assessment of cell viability. Mitochondrial dehydrogenases produced by viable cells reduce the WST-1 reagent to form formazan dye in an amount directly proportional to the number of metabolically active cells in the well. This dye was quantified using a Biotex Synergy multiplate reader to measure absorbance at 450 nm (reference wavelength was 630 nm). All treatments were assayed in triplicate (n=3) and calculated according to equation 5:

$$\text{Cell Viability (\%)} = \frac{OD_{450} \text{ of Treated Cells}}{OD_{450} \text{ of Treated Cells}} \times 100 \quad (5)$$

Statistical Analysis

A two-way analysis of variance (ANOVA) was employed to identify statistical differences among the various experimental groups and their corresponding control groups. Experimental groups with p-values of $p<0.05$ were considered to be statistically significant.

Characterization of Doxycycline-Loaded Nanoparticles

Blank and doxycycline-loaded chitosan nanoparticles were successfully prepared using an ionic gelation method. The blank particles, BKCNP4 and BKCNP6, were relatively large, with an average diameter of 4,900 nm and 4,450 nm, respectively (data not shown). Both groups of particles were spherical in shape with a narrow particle size distribution. The drug-loaded particles were smaller than their blank counterparts. The DCNP4 particles (FIG. 18*a*), with an average particle diameter of 44.50 nm, were two orders of magnitude smaller than their corresponding blanks and had a wider particle size distribution profile. DCNP4s were spherical in shape with smooth edges (FIG. 18*b*). Similarly, the DCNP6 particles (FIG. 18*c*), with an average diameter of 280 nm, were small compared to their blank counterparts—about 1/15 the size—but were significantly larger than the DCNP4s. In contrast to the DCNP4s, the DCNP6 particles exhibited a very narrow particle size distribution profile. The DCNP6 particles were spherical like the DCNP4s but had edges that were not as smooth (FIG. 18*d*).

Since the conditions that varied between the two formulations for preparing these particles was the concentration of the TPP crosslinker and the resulting ratio of chitosan to TPP, based on the previous data, it is now known that the concentration of the crosslinker plays a role in determining particle size. Also, inclusion of the doxycycline in the formulations produced particles significantly smaller than the blanks, which is an interesting finding that our group is currently investigating. Having a narrower particle size distribution profile—i.e., particles of more uniform size—is also important. The more similar the particles are in size, the more equally the drug will be distributed among the particles, which will normalize the rate of drug release.

Encapsulation Efficiency

Across all batches of DCNP4, the lowest encapsulation efficiency was 22%, the highest was 69%, and the average was 53%±19. For DCNP6, the lowest encapsulation efficiency was 41%, the highest was 68%, and the average was 56%±10. Even though DCNP6 was substantially larger in diameter, there was no significant difference in the amount of drug encapsulated for each type of DCNP.

Drug Release

Figure 19:
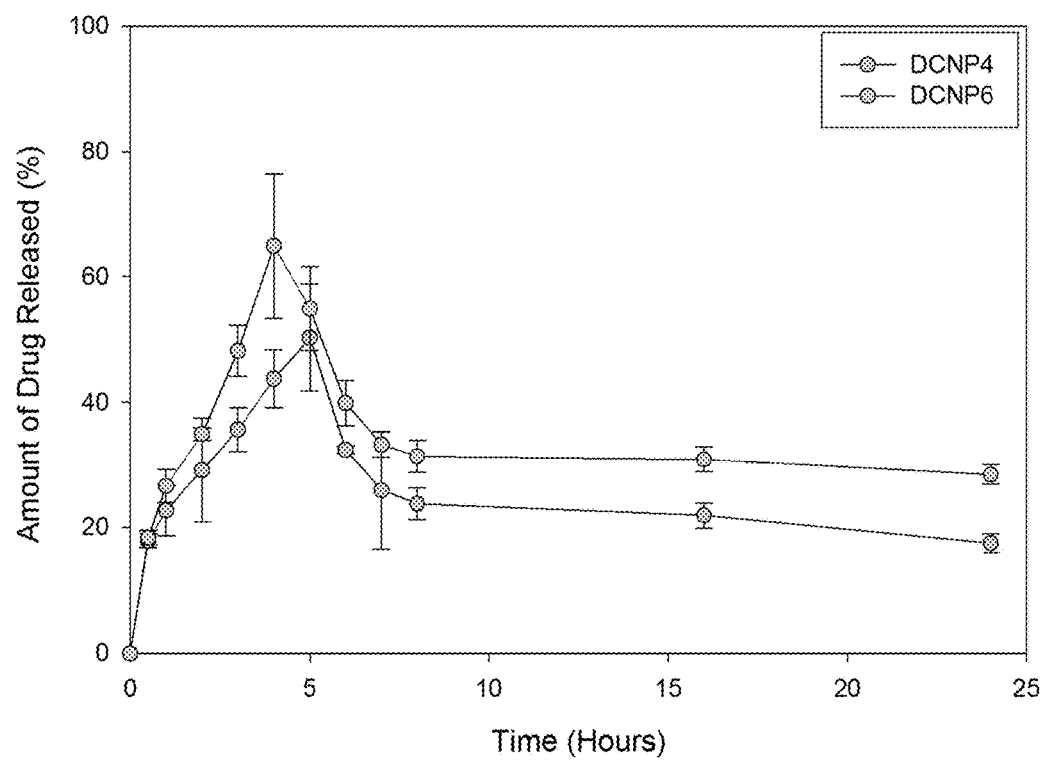
FIG. 19 is a graph depicting the amount of doxycycline release over a 24-hour period for DCNP4 and DCNP6. Both had an initial burst effect within the first four to five hours. Then, there was a decrease in the amount of drug being released followed by a slow sustained amount for the remaining hours. Data shown are the mean±standard deviation (n=3).

Doxycycline was released from the DCNPs in a burst-effect manner followed by a slow sustained release (FIG. 19). For DCNP4, the burst effect occurred within the first five hours; for DCNP6, within the first four hours. Within the first couple of hours after this initial burst, the amount of drug released decreased, then, it was followed by a sustained release for the remaining time. By the end of the 24-hour monitoring period, DCNP6 had released more total drug than the DCNP4. The difference between the amounts of drug released by the two different particle formulations can be attributed to the differences in particle size, with the larger particles (DCNP6) releasing more antibiotic than the smaller ones (DCNP4). A burst effect followed by slow sustained release, as demonstrated by both nanoparticle formulations, is ideal for treating microbial infections such as PID. For PID, delivering the particles in a local (i.e., transcervical) manner to the reproductive lumen would provide an increasing amount of doxycycline in the beginning, followed by a reduced amount afterwards. This would increase the likelihood of total pathogen elimination.

Antimicrobial Activity Assessment

Figure 20:
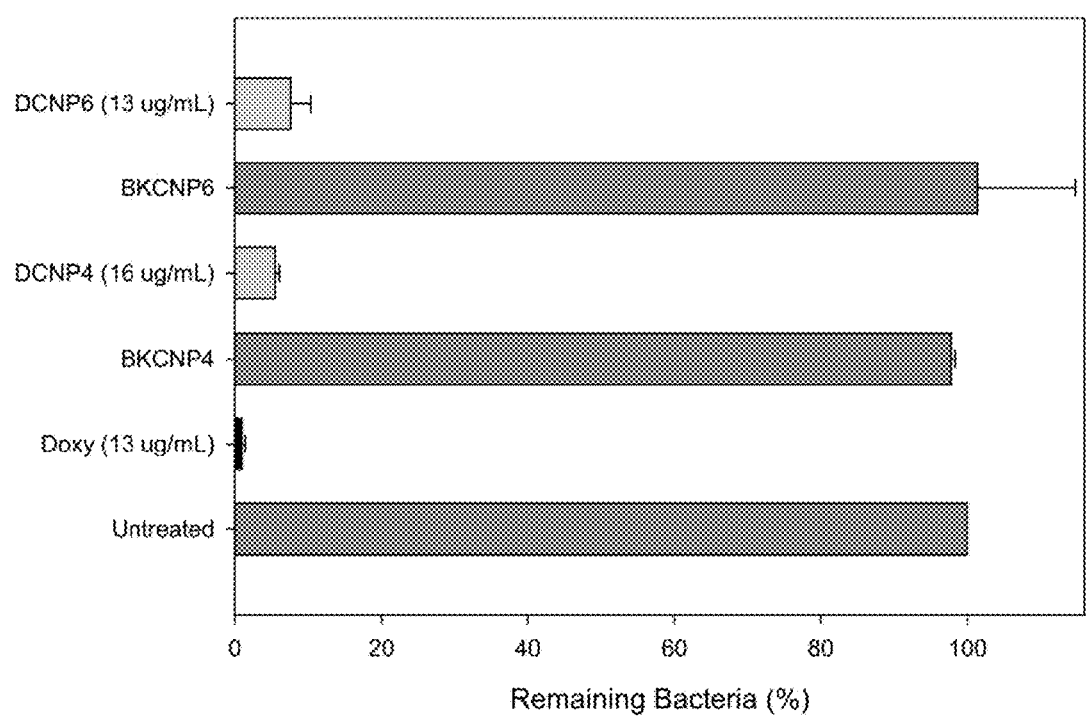
FIG. 20 is a graph depicting inhibitory effects of drug-loaded chitosan nanoparticles on bacterial growth, expressed in terms of percentage of remaining bacteria after four hours of treatment. MIC values are as follow: DCNP4=16 µg/mL, DCNP6=13 µg/mL, and Doxy=13 µg/mL. The untreated tube was used to define the "100% remaining" (no inhibition) case. Data shown are the mean±standard deviation (n=3).
Figure 30:
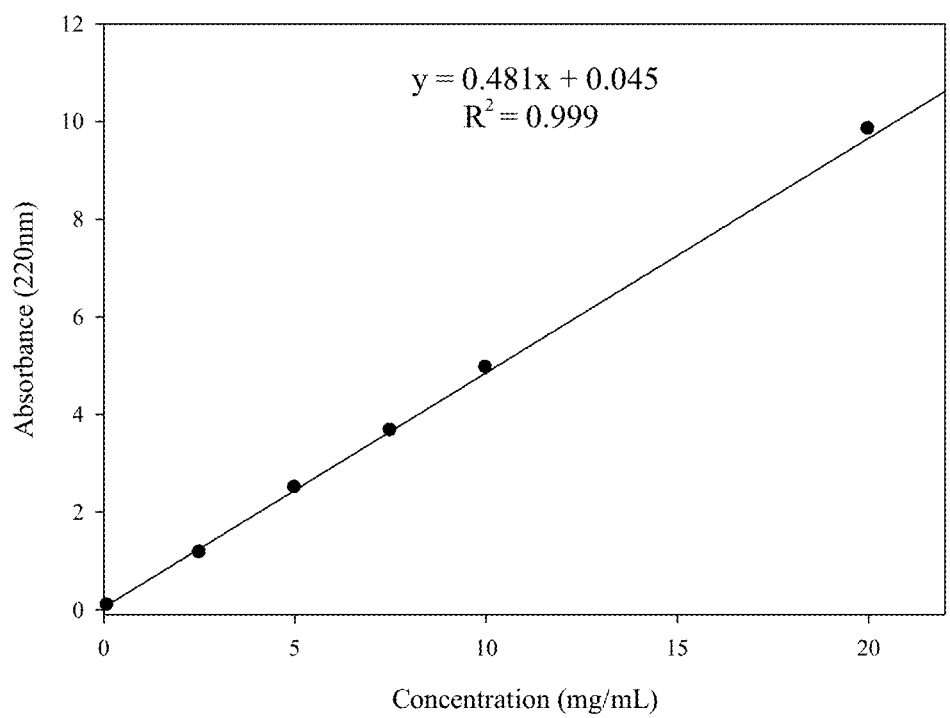
FIG. 30 is a graph depicting the doxycycline standard curve.
Figure 31:
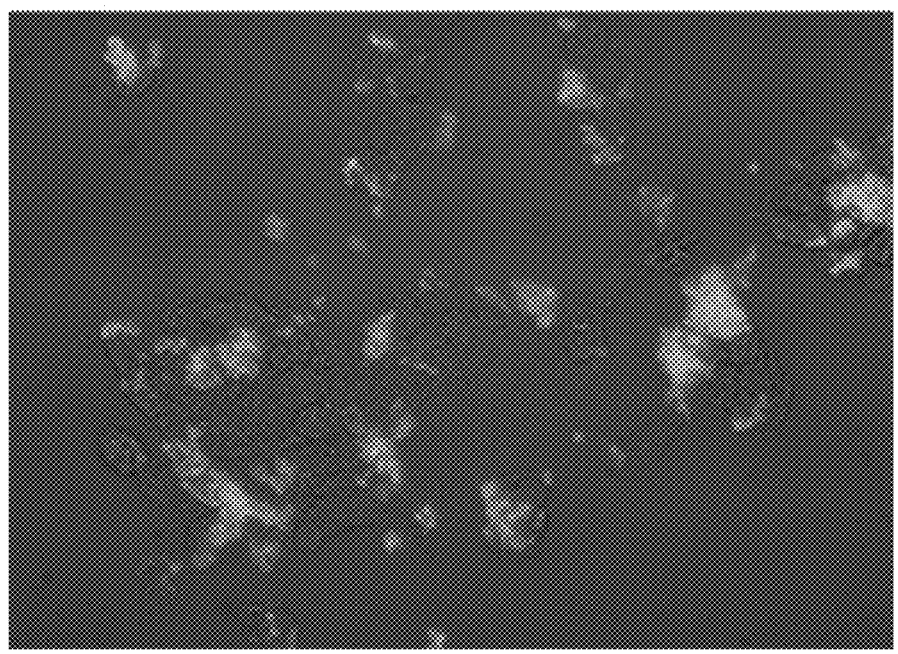
FIG. 31 is an image depicting Hek 293 transfected cells with pGFP. The image shows the expression of pGFP in Hek 293 cells after transfected with pGFP-loaded chitosan nanoparticles prepared using the ionic gelation method day 3.

After four hours incubation at 37° C., the drug-loaded nanoparticles' minimum inhibitory doxycycline concentration, MIC, was 16 μg/mL for DCNP4 and 13 μg/mL for DCNP6. FIG. 20 shows the MIC cases for DCNP4 (16 μg/mL) and DCNP6 (13 μg/mL) with unencapsulated doxycycline (Doxy—13 μg/mL) and blank particles serving as controls. For both types of DCNPs, more than 92% *E. coli* growth inhibition was observed. The minimum bactericidal concentration, MBC, was 48 μg/mL and 40 μg/mL for DCNP4 and DCNP6, respectively. Unencapsulated doxycycline treatments (Doxy), conducted at the same concentrations as the DCNP drug concentrations, resulted in the near-elimination of *E. coli*. These data suggest that the unencapsulated doxycycline had a higher antibacterial activity than the DCNPs within the four-hour period. However, because the DCNPs release the doxycycline in a slow and sustained manner, the inventors speculate that the nanoparticles' antibacterial activity would have been higher if the incubation period had been extended beyond four hours.

Cytotoxicity Assessment

For the case of initial human ovarian surface epithelial (OSE) cell densities of $5\times10^2$, no cytotoxicity (relative to the cells-only case) was induced by the 1 μg/mL or 2 μg/mL dosages of either DCNP formulation. In other words, cells treated with the DCNPs for five days showed high cell viability (FIG. 21). In fact, a significant increase in cell proliferation relative to the cells-only case was often observed when the OSE cells were treated with blank or doxycycline-loaded nanoparticles. In contrast, unencapsulated doxycycline at the same dosages induced severe cell toxicity: only 39% of the original population remained viable after the five-day treatment. Cells treated with both dosages of DCNP4 or with BKCNP4 had a higher viability than the untreated cells. For DCNP6, the viability of cells treated with 1 μg/mL was higher than for untreated cells, but cells treated with 2 μg/mL showed lower viability. Nevertheless, the DCNP6 case still showed greater cell viability than the unencapsulated drug treatments. Data from the wells with $1.0\times10^3$ and $2.0\times10^3$ initial cell densities are not presented because of cell overcrowding over the five-day period.

These cytotoxicity results show that encapsulation of doxycycline into the chitosan polymer reduces the toxicity that is normally induced by the unencapsulated drug. The differences between the DCNP4 and DCNP6 cytotoxicity results are possibly due to the differences in their size and the amount of drug released. The DCNP6s were observed to release more doxycycline than the DCNP4s. Further exploration and evaluation of the effects of chitosan particles on cell growth is necessary to explain the observed increase in proliferation.

Doxycycline-induced cytotoxicity was confirmed visually through observations of cell morphology following exposure to doxycycline. Cells treated with 1 μg/mL and 2 μg/mL dosages of doxycycline show the morphology of dead cells. The morphological effects of treating with DCNP4 (at 2 μg/mL) and unencapsulated doxycycline (also at 2 μg/mL) are illustrated in FIG. 22. Note that the cells treated with the DCNPs were of the same morphology as the untreated cells. This further demonstrates that encapsulation of doxycycline into chitosan nanoparticles minimizes the adverse effects of the drug. The disclosures of all publications cited above are expressly incorporated herein by reference, each in its entirety, to the same extent as if each were incorporated by reference individually.

Doxycycline-loaded chitosan nanoparticles were synthesized and characterized to analyze their properties for targeted drug delivery. Two types of nanoparticles were formulated with differing concentrations of crosslinker: DCNP4 and DCNP6. The DCNP6 formulation contained approximately 1.5 times more TPP crosslinker than DCNP4. Results showed that both types of drug-loaded chitosan nanoparticles were spherical, with encapsulation efficiencies of approximately 50%, and with a similar drug release profile. Both formulations also inhibited the growth of *Escherichia coli* after four hours of incubation. MBC (minimum bactericidal concentration) values were less than 50 μg/mL. The DCNPs induced significantly less apparent cytotoxicity than the unencapsulated doxycycline. These results demonstrate that the encapsulation of doxycycline into chitosan nanoparticles has the potential to minimize adverse drug side effects.

CONCLUSION

A new device and nanoparticle-based approach to improve the accuracy of diagnosis and treatment of pelvic inflammatory disease (PID) was presented herein. A new device was developed to procure sterile specimen samples from the endometrium by passing through highly contaminated vaginal and cervical areas. The analysis of uncontaminated endometrium tissue samples provides accurate diagnosis of PID, the specific organism causing it, and the particular drug to be administered. The developed device was designed to accommodate any size of cervices and collect up adequate specimen sample. The device was validated using an agar sampling test that demonstrated the capability of the presented SUSC device to significantly reduce contamination of the collected sample.

The presented device can also be used for directly delivering nanoencapsulated drugs at the site of infection. The inventors analyzed the encapsulation of doxycycline into chitosan nanoparticles using the ionic gelation method to better understand the size variation of the particles produced through this method. Twelve preparatory variables were analyzed as being relevant in determining chitosan particle sizes by the ionic gelation method. Statistical analysis was performed to select significant variables that were used to build an optimal model for determining the particle size. The statistical study showed that the mean particle diameter of chitosan particles (drug-free or drug-loaded) prepared by the ionic gelation method can be manipulated by varying four key formulation parameters. Based on two independent statistical methods, these parameters are: the chitosan-to-TPP ratio, wash/resuspension solution, synthesis time, and TPP concentration. These four variables contributed to 58% of the total variation in observed particle size. Mean particle diameter was found to be directly proportional to synthesis time and inversely proportional to the chitosan-to-TPP ratio and TPP concentration. In other words, increasing the chitosan-to-TPP ratio, and TPP concentration while lowering the synthesis time can lead to the formation of smaller particles. Using PBS as the wash/resuspension solution instead of water also decreases the particle size. In addition, it was observed that dissolving or protonating chitosan in acetic acid of concentration higher than 0.25M resulted in chitosan degradation. From the TEM studies, it was observed that centrifugation (rather than passive settling) of the particles followed by resuspension in nanopure water (rather than PBS) result in severe particle clumping (aggregate) and larger particle diameters.

Two particle formulations were examined in more detail: formulation DCNP6 containing approximately 1.5 times the crosslinker concentration of the other formulation named DCNP4. Both formulations produced spherically shaped drug-loaded nanoparticles. The spheres ranged in size from 30 to 220 nm diameter for DCNP4 and 200 to 320 nm diameter for DCNP6. Average encapsulation yield was 53% for DCNP4 and 56% for DCNP6. In terms of drug release, both formulations showed a burst effect within the first four to five hours, followed by a slow sustained release for the remainder of the 24-hour monitoring period. The in vitro antibacterial activity against *Escherichia coli* was high, with both formulations achieving more than 90% inhibition of four-hour bacterial growth. Cytotoxic effects of the DCNPs on normal human ovarian surface epithelial cells were significantly lower than those of unencapsulated doxycycline. After five days, cultures exposed to the unencapsulated antibiotic showed a 61% decrease in cell viability, while cultures exposed to the DCNPs exhibited less than a 10% decrease.

This work can lead to higher control of particle size and morphology (shape), which may in turn facilitate the use of the ionic gelation method for mass production of chitosan particles for drug delivery systems.

The inventors demonstrated that doxycycline-loaded chitosan nanoparticles have the potential for treating *E. coli*, a common co-pathogen in pelvic inflammatory disease, in a slow sustained manner without inducing any apparent cellular toxicity to the non-bacterial cells. These laboratory results suggest that doxycycline-loaded chitosan nanoparticles show promise for use in transcervical drug delivery and improved efficacy in the treatment of bacterial uterine infections. These results also demonstrate that the encapsulation of doxycycline into chitosan nanoparticles can minimize the adverse side effects of the drug while also beneficially releasing the drug in a slow and sustained manner.

These findings are not only beneficial for the diagnostic of PID but also for localized delivery of nanoencapsulated drugs to the uterus. Uncontaminated samples will allow a better understanding of the natural microbial ecology of the uterus under a variety of spontaneous and manipulated hormonal conditions. It is highly likely that microfilms of dormant pathogens exist in the endometrial cavity as they do in the inner ear, bladder and prostate, and this has enormous implications for fertility and complications of pregnancy. The SUSC device can also be used for addressing other gynecological disorders/problems such as removal of obstructions in the fallopian tubes, and targeted sperm delivery.

Clinical testing of the device in patients undergoing a hysterectomy is planned. With regard to the cellular growth induced by chitosan nanoparticles, future work includes studying whether the blank and drug-loaded particles used in this study induce cell proliferation in other cell types. Contingent upon the result of those preliminary studies, chitosan may be studied for its potential role in wound healing.

The inventors also evaluate the effects of the DCNPs on intracellular infectious organisms such as *Neisseria gonorrhoeae* and *Chlamydia trachomatis*, which contribute to two of the most common sexual transfected diseases. In order to treat infections that are caused by intracellular organisms, the drug needs to be delivered into the cells/tissues. The nanoparticle delivery system presented herein is ideal for treating these types of infections.

Based on the results from the effects of the doxycycline-loaded chitosan nanoparticles against *E. coli* in planktonic conditions, the inventors analyze the effect of the doxycycline-loaded chitosan nanoparticles in a biofilm system, preferably a biofilm model that is similar to that of the uterus biofilm. Results from inhibitory tests done in a biofilm system improve the clinical value for future application of these doxycycline-loaded chitosan nanoparticles in drug delivery.

After studying the doxycycline-loaded chitosan in a biofilm model, these particles are evaluated in vivo. The chitosan nanoparticles do not induce any form of cytotoxicity as shown in the in vitro studies. The particles should be delivered in a transcervical manner with a miniature version of the SUSC device. An ideal animal model would be one that has an infection in the uterus similar to PID on humans.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of treating endometrial infections comprising:
    encapsulating a drug in a chitosan nanoparticle wherein the chitosan nanoparticle is formed using an ionic gelation method comprising:
        preparing a chitosan solution comprising:
            dissolving chitosan powder in acetic acid having a concentration of 0.25M;
            stirring the solution; and
            incubating the solution to promote protonation;
        preparing a crosslinker solution comprising dissolving a cross-linker in 0.25M acetic acid;
        preparing a drug solution comprising dissolving the drug in nanopure water; and
        combining the chitosan solution, the crosslinker solution and the drug solution to form the chitosan nanoparticle encapsulating the drug;
    loading the encapsulated drug into a device wherein the device is comprised of:

a cannula having a first end and a second end wherein an orifice is formed in the first end of the cannula;

a sterile cover having first and second ends wherein the sterile cover is positioned over the first end of the cannula;

a hard ring containing a lock having at least one slot disposed therein and positioned on the second end of the cover wherein the ring is harder than the cover; and at least one flange positioned at the second end of the cannula wherein in use the at least one flange engages with the at least one slot in the lock on the cover to secure the cover over the cannula to encase an entire length of the cannula;

inserting the device into a uterus through a vagina;

inserting a sampler into the cannula wherein the sampler has a diameter between 2 mm to 10 mm;

advancing the sampler through the cover and out of the orifice in the cannula into the uterus wherein when the sampler is advanced through the cover the cover retracts to the lock engaged with the at least one flange located at the second end of the cannula;

dispensing the nanoparticle-encapsulated drug by advancing a plunger through the sampler; and removing the device from the uterus and the vagina.

2. The method of claim 1, wherein the drug is doxycycline.

3. The method of claim 1, wherein tripolyphosphate is used as the crosslinker in the formation of the chitosan nanoparticle.

4. The method of claim 1, wherein the lock has a circular cross-section having a singular orifice through a center portion of the lock with the at least one slot extending outward from the singular orifice of the lock.

* * * * *